United States Patent
Holm

(10) Patent No.: US 10,538,744 B2
(45) Date of Patent: Jan. 21, 2020

(54) USE OF ADENOVIRUS AND NUCLEIC ACIDS CODING THEREFOR

(71) Applicant: Per Sonne Holm, Furstenfeldbruck (DE)

(72) Inventor: Per Sonne Holm, Furstenfeldbruck (DE)

(*) Notice: Subject to any disclaimer, the term of this patent is extended or adjusted under 35 U.S.C. 154(b) by 0 days.

(21) Appl. No.: 15/452,470

(22) Filed: Mar. 7, 2017

(65) Prior Publication Data

US 2018/0002674 A1   Jan. 4, 2018

Related U.S. Application Data

(60) Division of application No. 12/769,435, filed on Apr. 28, 2010, now Pat. No. 10,155,930, which is a continuation of application No. 10/515,238, filed as application No. PCT/EP03/05583 on May 27, 2003, now abandoned.

(30) Foreign Application Priority Data

| May 27, 2002 | (DE) | ................................. 102 23 534 |
| Jun. 7, 2002 | (DE) | ................................. 102 25 400 |
| Oct. 15, 2002 | (DE) | ................................. 102 48 039 |
| May 19, 2003 | (DE) | ................................. 103 22 530 |

(51) Int. Cl.
| C12N 7/00 | (2006.01) |
| C07K 14/005 | (2006.01) |
| C12N 15/86 | (2006.01) |
| A61K 35/761 | (2015.01) |
| A61K 35/763 | (2015.01) |
| A61K 48/00 | (2006.01) |
| A61K 38/00 | (2006.01) |

(52) U.S. Cl.
CPC .............. *C12N 7/00* (2013.01); *A61K 35/761* (2013.01); *A61K 35/763* (2013.01); *C07K 14/005* (2013.01); *C12N 15/86* (2013.01); *A61K 38/00* (2013.01); *A61K 48/00* (2013.01); *C12N 2710/10322* (2013.01); *C12N 2710/10332* (2013.01); *C12N 2710/10343* (2013.01); *C12N 2830/00* (2013.01); *C12N 2840/203* (2013.01)

(58) Field of Classification Search
CPC ...... A61K 35/761; A61K 38/00; C12N 15/86; C12N 2710/10332; C12N 2710/10343; C12N 2710/10032; C12N 2710/10341; C12N 2710/10043; C12N 2710/10321; C07K 14/4702; C07K 14/005; C07K 14/47

See application file for complete search history.

(56) References Cited

U.S. PATENT DOCUMENTS

| 4,947,842 | A | 8/1990 | Marchosky et al. |
| 5,801,029 | A | 9/1998 | McCormick |
| 5,824,544 | A | 10/1998 | Armentano et al. |
| 5,856,181 | A | 1/1999 | McCormick |
| 5,871,726 | A | 2/1999 | Henderson et al. |
| 5,972,706 | A | 10/1999 | McCormick |
| 5,994,132 | A | 11/1999 | Chamberlain et al. |
| 5,998,205 | A | 12/1999 | Hallenbeck et al. |
| 6,022,863 | A | 2/2000 | Peyman |
| 6,110,744 | A | 8/2000 | Fang et al. |
| 6,140,126 | A | 10/2000 | Cowsert et al. |
| 6,428,968 | B1 | 8/2002 | Molnar-Kimber et al. |
| 6,635,476 | B1 | 10/2003 | Murphy |
| 6,649,158 | B1 | 11/2003 | LaFace |
| 6,683,059 | B1 | 1/2004 | Hung et al. |
| 6,713,055 | B2 | 3/2004 | Schiff |
| 6,730,662 | B1 | 5/2004 | Branton et al. |
| 6,955,808 | B2 | 10/2005 | Curiel |
| 7,001,596 | B1 | 2/2006 | Johnson et al. |
| 7,195,896 | B2 | 3/2007 | Kovesdi et al. |
| 8,158,753 | B2 | 4/2012 | Skerra et al. |
| 8,536,307 | B2 | 9/2013 | Skerra et al. |
| 2002/0086411 | A1 | 7/2002 | Holm |
| 2002/0091083 | A1 | 7/2002 | Higashi et al. |
| 2003/0044383 | A1 | 3/2003 | Henderson et al. |
| 2003/0095989 | A1 | 5/2003 | Irving et al. |
| 2003/0099619 | A1 | 5/2003 | Wickham et al. |
| 2004/0067586 | A1 | 4/2004 | Holm |
| 2004/0081637 | A1 | 4/2004 | Curiel |
| 2004/0265277 | A1 | 12/2004 | Holm |
| 2005/0031591 | A1 | 2/2005 | Hamada |
| 2005/0163753 | A1 | 7/2005 | Vogels et al. |
| 2005/0260162 | A1 | 11/2005 | Fueyo et al. |

(Continued)

FOREIGN PATENT DOCUMENTS

| CA | 2487811 | 12/2003 |
| DE | 19742706 | 4/1999 |

(Continued)

OTHER PUBLICATIONS

Juan Fueyo et al. Oncology, Published by Oncogene vol. 19, pp. 2-12 (Jan. 6, 2000).*
A. Eliseeva et al. Biochemistry (Moscow), Dec. 2011, vol. 76, Issue 13, pp. 1402-143311.*
Satoshi et al. Gene 1998, vol. 206, No. 1, published on Jan. 5, 1998, pp. 93-97.*
Sauthoff et al. Molecular Therapy 2004, vol. 10, No. 4, pp. 749-756.*
Heise et al. Nature Medicine 2000, vol. 6, No. 10, pp. 1134-1139.*
United States Patent Office Action for U.S. Appl. No. 14/850,373 dated Oct. 20, 2017 (8 pages).
United States Patent Office Action for U.S. Appl. No. 12/769,435 dated Nov. 15, 2017 (7 pages).
U.S. Pat. No. 7,572,633 2007/0116670, Aug. 11, 2009, Holm.
U.S. Pat. No. 8,263,067 2004/0067586, Sep. 11, 2012, Holm.
U.S. Pat. No. 8,586,354 2010/0297731, Nov. 19, 2013, Holm.
U.S. Pat. No. 8,921,100 2010/0015700, Dec. 30, 2014, Holm.
U.S. Pat. No. 8,951,772 2006/0057113, Mar. 16, 2006, Holm.

(Continued)

Primary Examiner — Bao Q Li
(74) Attorney, Agent, or Firm — Casimir Jones, S.C.; Peter J. Schlueter

(57) ABSTRACT

This invention relates to the use of an adenovirus to treat cancer, for example. The adenovirus may be replication deficient in cells that lack Y box binding protein. The adenovirus may encode an oncogene or an oncogene product, which may transactivate at least one viral gene.

7 Claims, 19 Drawing Sheets

Specification includes a Sequence Listing.

(56) References Cited

U.S. PATENT DOCUMENTS

| | | | |
|---|---|---|---|
| 2006/0099178 A1 | 5/2006 | Holm | |
| 2006/0270016 A1 | 11/2006 | Holm | |
| 2006/0270041 A1 | 11/2006 | Howe et al. | |
| 2007/0110719 A1 | 5/2007 | Holm | |
| 2007/0202524 A1 | 8/2007 | Murphy | |
| 2007/0292396 A1 | 12/2007 | Fueyo et al. | |
| 2009/0232800 A1 | 9/2009 | Holm | |
| 2010/0311145 A1 | 12/2010 | Holm | |
| 2010/0330037 A1 | 12/2010 | Holm | |
| 2011/0033424 A1 | 2/2011 | Holm | |
| 2011/0275093 A1 | 11/2011 | Holm | |
| 2012/0039877 A1 | 2/2012 | Holm | |

FOREIGN PATENT DOCUMENTS

| | | |
|---|---|---|
| DE | 10150945 | 4/2003 |
| DE | 10150984 | 4/2003 |
| EP | 0533838 | 12/1997 |
| EP | 0931830 | 3/2001 |
| JP | 11-506311 | 6/1999 |
| JP | 2005-523730 | 8/2005 |
| JP | 2006-512284 | 4/2006 |
| JP | 2006-518589 | 8/2006 |
| JP | 2007-511211 | 5/2007 |
| JP | 2007-511212 | 5/2007 |
| JP | 2008-526188 | 7/2008 |
| WO | WO 91/19813 | 12/1991 |
| WO | WO 94/18992 | 9/1994 |
| WO | WO 95/34671 | 12/1995 |
| WO | WO 97/16547 | 5/1997 |
| WO | WO 98/01563 | 1/1998 |
| WO | WO 98/08856 | 3/1998 |
| WO | WO 98/29555 | 7/1998 |
| WO | WO 98/46779 | 10/1998 |
| WO | WO 99/06576 | 2/1999 |
| WO | WO 99/16873 | 4/1999 |
| WO | WO 99/18799 | 4/1999 |
| WO | WO 00/22136 | 4/2000 |
| WO | WO 00/39317 | 7/2000 |
| WO | WO 00/56909 | 9/2000 |
| WO | WO 00/78327 | 12/2000 |
| WO | WO 01/02556 | 1/2001 |
| WO | WO 01/70951 | 9/2001 |
| WO | WO 02/053711 | 7/2002 |
| WO | WO 03/033692 | 4/2003 |
| WO | WO 03/099859 | 12/2003 |
| WO | WO 2004/001032 | 12/2003 |
| WO | WO 2004/035616 | 4/2004 |
| WO | WO 2004/083404 | 9/2004 |
| WO | WO 2005/051430 | 6/2005 |
| WO | WO 2005/052143 | 6/2005 |
| WO | WO 2006/070023 | 7/2006 |
| WO | WO 2006/070024 | 7/2006 |

OTHER PUBLICATIONS

Ahmad T. et al., "Review of the Use of Topotecan in Ovarian Carcinoma," Expert Opin. Pharmacother., 2004, 5, 2333-2340.
Ahonen et al., "Antitumor activity and bystander effect of adenovirally delivered tissue inhibitor of metalloproteinases-3," Mol. Therapy (2002) 5(6):705-715.
Alemany et al., "Replicative adenoviruses for cancer therapy," Nature Biotech. (2000) 18:723-727.
Amin, A. et al., "(-nitrocamptothecin as second line chemotherapy for men with progressive, metastatic, hormone refractory prostate cancer: results of the CALGB 99901," Urol. Oncol. (2004) 22(5):398-403.
Anderson et al., "Human gene therapy," Nature (1998) 392:25-30.
Arai et al., "Gene transfer of Fas ligand induces tumor regression vivo," Proc. Natl. Acad. Sci. (1997) 94(25):13862-13867.
Atadja et al., "Selective growth inhibition of tumor cells by a novel histone deacetylase inhibitor, NVP-LAQ824," Cancer Res. (2004) 64(2):689-695.
Avemann et al.I, "Camptothecin, a specific inhibitor of type I DNA topoisomerase induces DNA breakage at replication forks," Mol. Cell. Biol. (1988) 8(8):3026-3034.
Azzariti, A. et al., "The schedule-dependent enhanced cytotoxic activity of 7-ethyl-10-hydroxy-camptothecin (SN-38) in combination with Gefitinib (Iressa ZD1839)," Biochem. Pharmacol. (2004) 68(1):135-144.
Balague, C. et al., "Human papillomavirus E6E7-mediated adenovirus cell killing: selectivity of mutant adenovirus replication in organotypic cultures of human keratinocytes," J. Virol. (2001) 75(16):7602-111005.
Bargou, R.C. et al., "Nuclear localization and increased levels of transcription factor YB-1 in primary human breast cancers are associated with intrinsic MDR1 gene expression," Nature Med. (1997) 3(4):447-450.
Barnett, B.G. et al., "Targeted adenoviral vectors," Biochimica Biophysica Acta (2002) 1575:1-14.
Bauman et al., "Targeting the epidermal growth factor receptor in radiotherapy: radiobiological mechanisms, preclinical and clinical results," Radiother. Oncol., 2004, 72, 257-266.
Bauzon M. et al., "Multigene expression from a replicating adenovirus using native viral promoters," Molecular Therapy 7, 2003, 526-534.
Ben-Israel and Kleiberger, "Adenovirus and cell cycle control," Front. Biosci., 7: 1369-1395 (2002).
Berk, A.J., "Adenovirus promoters EIA tranactivation," Ann. Rev. Genet. (1986) 20:45-79.
Bhat, G. et al., "In vivo identification of multiple promoter domains of adenovirus EHA-late promoter," EMBO Journal (1987) 6(7):2045-2052.
Bieler, A. et al., "Novel three-pronged strategy to enhance cancer cell killing in glioblastoma cell linse: histone deacetylase inhibitor, chemotherapy, and oncolytic adenovirus dl520," Human Gene Ther. (2006) 17:55-70.
Binaschi, M. et al., "Relationship between lethal effects and topoisomerase II-mediated double-stranded DNA breaks produced by anthracyclines with different sequence specificity," Mol. Pharmacol. (1997) 51(6):1053-1059.
Bischof, M. et al., "Triple combination of irradiation, chemotherapy (pemetrexed), and VEGFR inhibition (SU5416) in human endothelial and tumor cells," Int. J. Radiat. Oncol. Biol. Phys. (2004) 60(4):1220-1232.
Bonapace et al., "Np95 is regulated by E1A during mitotic reactivation of terminally differentiated cells and is essential for S phase entry," J. Biol. Chem. (2002) 157(6):909-914.
Boulanger, P.A. et al., "Expression and interactions of human adenovirus oncoproteins," Biochem. J. (1991) 275:281-99.
Boulikas, T., "Nuclear Localization Signals (NLS)," Crit. Rev. Eukaryot. Gene Expr., 3(3): 193-227 (1993).
Braithwaite et al., "Induction of cell death by adenoviruses," Apoptosis (2001) 6(5):359-370.
Brandt, K., "Cancer gene therapy with tissue inhibitors of metalloproteinases (TIMPs)," Curr. Gene Therapy (2002) 2(2):255-271.
Braunstein, I. et al., "Human telomerase reverse transcriptase promoter regulation in normal and malignant human ovarian epithelial cells," Cancer Res. (2001) 61(14):5529-5536.
Bridge et al., "Interaction of adenoviral E4 and E1b products in late gene expression," Virology (1990) 174(2):345-353.
Brummelkamp, T.R. et al., "A system for stable expression of short interfering RNAs in mammalian cells," Science (2002) 296:550-53.
Camphausen, K. et al., "Enhancement of xenograft tumor radiosensitivity by the histone deacetylase inhibitor MS-275 and correlation with histone hyperacetylation," Clin. Cancer Res. (2004) 10(18):6066-6071.
Cantore, M. et al., "Combined irinotecan and oxaliplatin in patients with advanced pre-treated pancreatic cancer," Oncology (2004) 67(2):93-97.
Cao, G. et al., "Comparison of carcinoembryonic antigen promoter regions isolated from human colorectal carcinoma and normal adjacent mucosa to induce strong tumor-selective gene expression," Int. J. Cancer (1998) 78(2):242-247.
Chen, C.-Y. et al., "Nucleolin and YB-1 are required for JNK-mediated interleukin-2 mRNA stabilization during T-cell activation," Genes & Development (2000) 14:1236-48.

(56) References Cited

OTHER PUBLICATIONS

Chung, I. et al., "Use of L-plastin pomoter to develop an adenoviral system that confers transgene expression in ovarian cancer cells but not in normal mesothelial cells," Cancer Gene Ther. (1999) 6(2):99-106.
Cin, "Genomic changes in endometrial polyps associated with tamoxifen show no evidence for its action as an external carcinogen," Cancer Res. (1998) 58(11):2278-2281.
Clamp et al., "A Phase IIA Study of the Topoisomerase I Inhibitor, Exatecan Mesylate (DX-8951f), Administered at Two Different Dose Schedules in Patients With Platinum- and Taxane-Resistant/Refractory Ovarian Cancer," Gynecol. Oncol., 2004, 95, 114-119.
Colby, W.W. et al., "Adenovirus type 5 virions can be assembled in vivo in the absence of detectable polypeptide IX," J. Virol. (1981) 39(3):977-980.
Cooney et al., "A Phase IB Clinical and Pharmacokinetic Study of the Angiogenesis Inhibitor SU5416 and Paclitaxel in Recurrent or Metastatic Carcinoma of the Head and Neck," Cancer Chemother. Pharmacol 2004, 55(3):295-300.
Coulson, J.M. et al., "Tumour-specific arginine vasopressin promoter activation in small-cell lung cancer," Br. J. Cancer (1999) 80(12):1935-1944.
DeFilipe et al., "Skipping the co-expression problem: the new 2A 'CHYSEL' technology," Genet. Vaccines Ther. (2004) 2(1):13.
Deonarain, M., "Ligand targeted receptor-mediated vectors for gene delivery," Expert Opin. Ther. Pat. (1998) 8:53-69.
Descamps, V. et al., "Strategies for cancer gene therapy using adenoviral vectors," J. Mol. Med. (1996) 74:183-89.
Didier et al., "Characterization of the cDNA encoding a protein binding to the major histocompatibility complex class II Y box," proc. Natl. Acad. Sci. USA (1988) 85:7322-7326.
Dmitriev IP et al., "Engineering of adenovirus vectors containing heterologous peptide sequences in the C terminus of capsid protein IX," Journal of Virology, 2002, 76, 6893-6899.
Dobbelstein, M. et al., "Nuclear export of the E1B 55-kDa and E4 34-kDa adenoviral oncoproteins mediated by a rev-like signal sequence," Embo J. (1997) 16(14):4276-4284.
Doronin, K. et al., "Tumor-specific, replication-competent adenovirus vectors overexpressing the adenovirus death protein," J. Virol. (2000) 74(13):6147-55.
Dyson, "The regulation of E2F by pRB-family proteins," N. Genes & Development (1998) 12(15):2245-2262.
Eck et al., Goodman & Gilman's The Pharmacological Basis of Therapeutics, McGraw-Hill, New York (1996) 77-101.
Efthymiadis, A. et al., "The HIV-1 tat nuclear localization sequence confers novel nuclear import properties," J. Biol. Chem. (1998) 273(3):1623-28.
Elbashir et al., "Duplexes of 21-nucleotide RNAs mediate RNA interference in cultured mammalian cells," Nature, 411: 494-498 (2001).
En-Nia et al., "Transcription Factor YB-1 Mediates DNA Polymerase α Gene Expression," The Journal of Biological Chemistry, 2004, 280, 7702-7711.
Evdokimova V. et al., "Akt-mediated YB-1 phosphorylation activates translation of silent mRNA species," Molecular and Cellular Biology, 2006, 26, 277-292.
Fang et al., "Diminishing adenovirus gene expression and viral replication by promoter replacement," J. Virol. (1997) 71(6):4798-4803.
Ferrara, N., "Role of Vascular Endothelial Growth Factor in Physiologic and Pathologic Angiogenesis: Therapeutic Implications," Semin. Oncol., 29 (6 Suppl 16): 10-14 (2002).
Freytag et al., "A novel three-pronged approach to kill cancer cells selectively: concomitant, viral, double-suicide gene, and radiotherapy," Hum. Gene Ther. (1998) 9:1323-33.
Fribley, A. et al., "Proteasome inhibitor PS-341 induces apoptosis through induction of endoplasmic reticulum stress-reactive oxygen species in head and neck squamous cell carcinoma cells," Mol. Cell Biol. (2004) 24(22):9695-9704.
Friedberg, E.C., Nuclear targeting sequences, TIBS (1992) 17(9):347.
Fueyo, J. et al., "A mutant oncolytic adenovirus targeting the Rb pathway produces antiglioma effect in vivo," Oncogene (2000) 19:2-12.
Gadi et al., "A long-acting suicide gene toxin, 6-methylpurine, inhibits slow growing tumors after a single administration," J. Pharmacol. and Exp. Therapeutics (2003) 304(3):1280-1284.
Gallimore, P.H. et al., "Adenovirus E1A: remodeling the host cell, a life or death experience," Oncogene (2001) 20:7824-7835.
Ganly, I et al., "Replication and cytolysis of an E1 B-attenuated adenovirus in drug-resistant ovarian tumor cells is associated with reduced apoptosis," Gene Therapy (2001) 8:369-375.
Ghosh-Coudhury, G. et al., "Protein IX, a minor component of the human adenovirus capsid, is essnetial for the packaging of full length genomes," EMBO J. (1987) 6(6):1733-1739.
Gilbert et al., "Phase I clinical and pharmacokinetic study of irinotecan in adults with recurrent malignant glioma," Clin. Cancer Res. (2003) 9(8):2940-2949.
Glenn et al., "Adenovirus 5 early region 1A host range mutants hr3, hr4, and hr5 contain point mutations which generate single amino acid substitutions," J. Virol. (1985) 56:66-74.
Goding, C.R. et al., "Multiple transcription factors interact with the adenovirus-2 EII-late promoter: evidence for a novel CCAAT recognition factor," Nucl. Acids Res. (1987) 15(19):7761-7780.
Goldsmith, M.E. et al., "The histone deacetylase inhibitor FK228 preferentially enhances adenovirus transgene expression in malignant cells," Clin. Cancer Res. (2003) 9(14):5394-5401.
Gomez-Manzano, C. et al., "Delta-24 increases the expression and activity of topoisomerase I and enhances the antiglioma effect of irinotecan," Clin. Cancer Res. (2006) 12(2):556-562.
Gomez-Navarro et al., "Gene therapy for cancer," Eur. J. Cancer (1999) 35:867-885.
Goodrum, F.D. et al., "Roles for the E4orf6, orf3, and E1B 55-kilodalton proteins in cell cycle-independent adenovirus replication," J. Virol. (1999) 73(9):7474-88.
Gorecki, D., "Prospects and problems of gene therapy: an update," Exp. Opin. Emerging Drugs (2001) 6(2):187-198.
Gottesman et al., "Biochemistry of multidrug resistance mediated by the multidrug transporter," Annu. Rev. Biochem. (1993) 62:385-427.
Green et al., "Adenovirus vectors: systemic delivery and tumor targeting," Cancer Gene Therapy (2002) 9;1036-1042.
Grunhaus, A. Horwitz, M.S., (1992) Adenoviruses as cloning vectors. Rice C (ed) Seminars in virology. Saunders Scientific, London, pp. 237-252.
Guo et al., "Protein tolerance to random amino acid change," Proc. Natl. Acad. Sci. USA (2004) 101(25):9205-9210.
Hajitou et al., "The antitumoral effect of endostatin and angiostatin is associated with adown-regulation of vascular endothelial growth factor expression in tumor cells," FASEB J. (2002) 16(13):1802-1804.
Hale et al., "The adenovirus oncoprotein Eta stimulates binding of transcription factor ETF to transcriptionally activate the p53 gene," J. Biol. Chem. (1999) 274:23777-23786.
Haley, K.P. et al., "Transformation properties of type 5 adenovirus mutants that differentially express the E1A gene products," Proc. Natl. Acad. Sci. USA (1984) 81:5734-5738.
Hallenbeck, P.L. et al., "A novel tumor-specific replication-restricted adenoviral vector for gene therapy of hepatocellular carcinoma," Human Gene Therapy (1999) 10(10):1721-1733.
Hasan, S. et al., "Transcription coactivator p300 binds PCNA and may have a role in DNA repair synthesis," Nature (2001) 410:387-391.
Hehir, K.M. et al., "Molecular characterization of replication-competent variants of adenovirus vectors and genome modifications to prevent their occurrence," J. Virol. (1996) 70(12):8459-8467.
Heise et al., "ONYX-015, an E1B gene-aqttenuated adenovirus, causes tumor-specific cytolysis and antitumoral efficacy that can be augmented by standard chemotherapeutic agents," Nature Med. (1997) 3(6):639-645.
Heise, C. "An adenovirus E1A mutant that demonstrates potent and selective systematic anti-tumoral efficacy," Nature Med. (2000) 6(10):1134-1139.

(56) References Cited

OTHER PUBLICATIONS

Helt, A-M. et al., "Mechanisms by which DNA tumor oncoproteins target the Rb family of pocket proteins," Carcinogenesis (2003) 24(2):159-69.
Holm, P.S. et al., "Multidrug-resistant cancer cells facilitate E1-independent adenoviral replication: impact for cancer gene therapy," Cancer Res. (2004) 64(1):322-328.
Holm, P.S. et al., "YB-1 relocates to the nucleus in adenovirus-infected cells and facilitates viral replication by inducing E2 gene expression through the E2 late promoter," J. Biol. Chem. (2002) 277(12):10427-34.
Horwitz, M.S. et al., Adenovirus immunoregulatory genes and their cellular target, Virol. (2001) 279:1-8.
Howe, J.A. et al., "Evaluation of E1-mutant adenoviruses as conditionally repliacting agents for cancer therapy," Mol. Ther. (2000) 2:485-495.
Hu, M-C. et al., "Adenovirus E1B 19K protein is required for efficient DNA replication in U937 cells," Virology (1997) 227(2):295-304.
Hu, Z. et al., "Transcriptional activation of the MDR1 gene by UV irradiation, role of NF-Y and Sp1," J. Biol. Chem. (2000) 275(4):2979-2985.
Huang et al., "Telomerase-dependent oncolytic adenovirus for cancer treatment," Gene Therapy (2003) 10:1241-1247.
Ise, T. et al., "Transcription factor Y-box bindings protein 1 binds preferentially to cisplatin-modified DNA and interacts with proliferating cell nuclear antigen," Cancer Res. (1999) 342-6.
Izumi, H. et al., "Y box-binding protein-1 binds preferentially to single-stranded nucleic acids and exhibits 3'-5' exonuclease activity," Nucl. Acid. Res. (2001) 29(5):1200-07.
Jaboin et al., "MS-27-275, an inhibitor of histone deacetylase, has marked in vitro and in vivo antitumor activity against pediatric solid tumors," Cancer Res. (2002) 62(21):6108-6115.
Jans, D.A. et al., "Nuclear targeting signal recognition: a key control point in nuclear transport?" Bioessays (2000) 22(6):532-44.
Jelsma et al., "Use of deletion and point mutants spanning the coding region of the adenovirus 5 E1A gene to define a domain that is essential for transcriptional activation," Virol. (1988) 163:494-502.
Ji, L. et al., "Induction of apoptosis and inhibition of tumorigenicity and tumor growth by adenovirus vector-mediated fragile histidine triad (FHIT) gene overexpression," Cancer Res. (1999) 59:3333-39.
Jones et al., Cell, "Isolation of adenovirus type 5 host range deletion mutants defective for transformation of rat embryo cells," 1979, vol. 17, Issue 3, 683-689.
Jurchott, K. et al., "YB-1 as a cell cycle-regulated transcription factor facilitating cyclin A and cyclin B1 gene expression," J. Biol. Chem. (2003) 278(30):270988-96.
Kamiya et al., "The expression of P73, P21 and MDM2 proteins in gliomas," J. Neurooncology (2002) 59(2):143-149.
Kaye et al., "A single amino acid substitution results in a retinoblastoma protein defective in phosphorylation and oncoprotein binding," Proc. Natl. Acad. Sci. USA (1990) 87:6922-6926.
Keen, J.C. et al., "A novel histone deacetylase inhibitor, scriptaid, enhances expression of functional estrogen receptor alpha (ER) in ER negative human breast cancer cells in combination with 5-aza 2prime-deoxycytidine," Breast Cancer Res. Treat. (2003) 81(3):177-186.
Khuri, F.R. et al., "A controlled trial of intramtumoral ONYX-015, a selectively-replicating adenovirus, in combination with cisplatin and 5-fluorouracil in patients with recurrent head and neck cancer," Nature Med. (2000) 6:879-85.
Kim, J.H. et al., "Susceptibility and radiosensitization of human glioblastoma cells to trichostatin A, a histone deacetylase inhibitor," Int. J. Radiat. Oncol. Biol. Phys. (2004) 59(4):1174-1180.
Kim, S.H. et al., "Apicidin is a histone deacetylase inhibitor with anti-invasive and anti-angiogenic potentials," Biochem. Biophys. Res. Comm. (2004) 315: 964-970.
Kindler, H.L. et al., "9-aminocamptothecin (9-AC) given as a 120-hour continuous infusion in patients with advanced adenocarcinomas of the stomach and gastroesophageal junction: a phase II trial of the University of Chicago phase II consortium," Invest. New Drugs (2004) 22(3):323-327.
Kirn et al., "The emerging fields of suicide gene therapy and virotherapy," Trends Mol. Med., 8(4) (Suppl.) (2002).
Kirn, D. et al., "A Phase II Trial of Intratumoral Injection with an E1B-Deleted Adenovirus, Onyx-015, in Patients with Recurrent, Refractory Head and Neck Cancer," Annual Meeting of the American Society of Clinical Oncology, 1998, 391a.
Kirn, D. et al., "Adenovirus E1A mutants that selectively replicate in and cause enhanced destruction of cancer cells in vitro and in nude mouse-human tumor xenografts," Cancer Gene Therapy (1998) 5(6):S26.
Kitazono, M. et al., "Enhanced adenovirus transgene expression in malignant cells treated with the histone deacetylase inhibitor FR901228," Cancer Res. (2001) 61(17):6328-6330.
Kodama et al., "The features and short comings for gene delivery of current non-viral carriers," Curr. Med. Chem. (2006) 13:2155-2161.
Koike, K. et al., "Nuclear translocation of the Y-box binding protein by ultraviolet irradiation," FEBS Lett. (1997) 17:390-94.
Koyama et al., "Combined suicide gene therapy for human colon cancer cells using adenovirus-mediated transfer of *Escherichia coli* cytosine deaminase gene and *Escherichia coli* uracil phosphoribosyltransferase gene with 5-fluorocytosine," Cancer Gene Ther. (2000) 7(7):1015-1022.
Kozarsky et al., "Gene Therapy: adenovirus vectors," Curr. Opinions in Genetics and Development (1993) 499-503.
Ladomery, M. et al., "A role for Y-box proteins in cell proliferation," BioEssays, ICSU Press (1995) 17(1):9-11.
Lasham, A. et al., "Regulation of the human fas promoter by YB-1, Pura and AP-1 transcription factors," Gene (2000) 252:1-13.
Le, Q.T. et al., "Phase I study of tirapazamine plus cisplatin/etoposide and concurrent thoracic radiotherapy in limited-stage small cell lung cancer (S0004): a Southwest Oncology Group Study," Clin. Cancer Res. (2004) 10(16):5418-5424.
Leitner et al., "Oncolytic Adenoviral Mutants with E1B19K Gene Deletions Enhanced Gemcitabine-induced Apoptosis in Pancreatic Carcinoma Cells and Anti-Tumor Efficacy In vivo," Clin Cancer Res., 2009, 15(5):1730-1740.
Leppard, K.N., "Regulated RNA processing and RNA transport during adenovirus infection," Seminars in Virology (1998) 8:301-07.
Lesk et al., "Prediction of protein function from protein sequence and structure," p. 27-28, downloaded Sep. 16, 2007.
Levenson, V.V., (Chernokhvostov), "Pleiotropic resistance to DNA-interactive drugs is associated with increased expression of genes," Cancer Res. (2000) 60:5027-30.
Li et al., "A hepatocellular carcinoma-specific adenovirus varient, CV890, eliminates distant human liver tumors in combination with doxorubicin," Cancer Res. (2001) 61:6428-6436.
Lindemann RK et al., "Histone-deacetylase inhibitors for the treatment of cancer," Cell Cycle, 2004, 3, 779-788.
Liu et al., "An E1B-19 kDa gene deletion mutant adenovirus demonstrates tumor necrosis factor-enhanced cancer selectivity and enhanced oncolytic potency," Molecular Therapy, 2004, 9, 786-803.
Lockett et al., "Relative efficiency of tumor cell killing in vitro by two enzyme-prodrug systems delivered by identical adenovirus vectors," Clin. Canc. Res. (1997) 3(11):2075-2080.
Lowenstein et al., "Progress and challenges in viral vector-mediated gene transfer to the brain," Curr. Opin. in Mol. Thera. (2002) 4(4):359-371.
Lyons, R.H., "Pentapeptide nuclear localization signal in adenovirus E1a," Mol. Cell Biol. (1987) 7(7):2451-2456.
Magnusson, M.K. et al., "Genetic retargeting of adenovirus: novel strategy employing 'deknobbing' of the fiber," J. Virology (2001) 75(16):7280-7289.
Majumdar, A.S. et al., "Efficacy of herpes sumplex virus thymidine kinase in combination with cytokine gene therapy in an experimental metastatic breast cancer model," Cancer Gene Ther. (2000) 7(7):1086-99.

(56) References Cited

OTHER PUBLICATIONS

Majumdar, A.S. et al., "The telomerase reverse transcriptase promoter drives efficacious tumor suicide gene therapy while preventing hepatotoxicity encountered with constitutive promoters," Gene Ther. (2001) 8:568-78.
Makino, Y. et al., "Structural and functional analysis of the human Y-box binding protein (YB-1) gene promoter," Nucl. Acid. Res. (1996) 24(10):1873-78.
Mantwill et al., "Inhibition of the multidrug-resistant phenotype by targeting YB-1 with a conditionally oncolytic adenovirus: implications for combinatorial treatment regimen with chemotherapeutic agents," Cancer Res. (2006) 66(14):7195-7202.
Manzano et al., "Delta-24 Increases the Expression and Activity of Topoisomerase I and Enhances the Antiglioma Effect of Irinotecan," Clin Cancer Res, 2006, 12(2):556-562.
Matsui, T. et al., "Adenovirus 2 peptide IX gene is expressed only on replicated DNA molecules," Mol. Cell Biol. (1986) 6(12):4149-4154.
Matsumoto, K., and Wolffe, A.P., "Gene regulation by Y-box proteins: coupling control of transcription and translation," Trends Cell Biol., 8: 318-323 (1998).
McClue, S.J., "In vitro and in vivo antitumor properties of the cyclin dependent kinase inhibitor CYC202 (R-roscovitine)," Int. J. Cancer (2002) 102(5):463-468.
McCormick, F., "Cancer gene therapy: fringe or cutting edge?" National Res. Center (2001) 1:130-141.
McNeish et al., "Gene therapy progress and prospects: cancer gene therapy using tumour suppressor genes," Gene Therapy (2004) 1-7.
Mertens, P.R. et al., "Glomerular mesangial cell-specific transactivation of matrix metalloproteinase 2 transcription is mediated by YB-1," J. Biol. Chem. (1997) 272(36):22905-12.
Mizuguchi and Hayakawa, "Targeted adenovirus vectors," Human Gene Therapy, 2004, 15, 1034-1044.
Mizuguchi et al., "Adenovirus vectors containing chimeric type 5 and type 35 fiber proteins exhibit altered and expanded tropism and increase the size limit of foreign genes," Gene (2002) 285:69-77.
Mymryk, J.S. et al., "Induction of gene expression by exon 2 of the major E1A proteins of adenovirus type 5," J. Virol. (1993) 67(12):6922-8.
Mymryk, J.S. et al., "Multiple pathways for activation of E2A expression in human KB cells by the 243R E1A protein of adenovirus type 5," Virus Res. (1994) 33(1):89-97.
Nemunaitis, J.J. et al., "Phase I study of oral CI-994 in combination with gemcitabine in treatment of patients with advanced cancer," Cancer J. (2003) 9:58-66.
Nevins, J.R., "E2F: A Link Between the Rb Tumor Supressor Protein and Viral Oncoproteins," Science, 258: 424-429 (1992).
Nevins, J.R., "Mechanism of activation of early viral transcription by the adenovirus E1A gene product," Cell (1981) 26(2):213-220.
Nicholson KM and Anderson NG, "The protein kinase B/Akt signalling pathway in human malignancy," Cell. Signal, 2002, 14, 381-395.
Nicklin, S.A. et al., "Ablating adenovirus type 5 fiber-CAR binding and HI loop insertion of the SIGYPLP peptide generate an endothelial cell-selective adenovirus," Mol. Ther. (2001) 4(6):534-42.
Niculescu-Duvaz et al., "Recent developments in gene-directed enzyme prodrug therapy (GDEPT) for cancer," Curr. Opin. Mol. Therapy, 1999, 1, 480-486.
Nimmanapalli, R. et al., "Histone deacetylase inhibitor LAQ824 both lowers expression and promotes proteasomal degradation of Bcr-Abl and induces apoptosis of imatinib mesylate-sensitive or -refractory chronic myelogenous leukemia-blast crisis cells," Cancer Res. (2003) 63(16):5126-5135.
Noteborn and Pietersen, "Apoptosis," Adc. Exp. Med. Biol., 2000, 465, 153-161.
Oda, Y. et al., "Nuclear expression fo YB-1 protein correlates with P-glycoprotein expression in human osteosarcoma," Clin. Can. Res. (1998) 2273-77.

Ohga, T. et al., "Direct involvement of the Y-box binding protein YB-1 in gentoxic stress-induced activation of the human multidrug resistance 1 gene," J. Biol. Chem. (1998) 5997-6000.
Ohga, T. et al., "Role of the human Y box-binding protein YB-1 in cellular sensitivity to the DNA-damaging agents cisplatin, Mitomycin C, and ultraviolet light," Cancer Res. (1996) 56:4224-28.
Okamoto et al., "Direct interaction of p53 with the Y-box binding protein," YB-1: a mechanism for regulation of human gene expression, Oncogene (2000) 19:6194-292.
Opalka et al., "Apoptotic Genes in Cancer Therapy," Cell Tissues Organs, 172: 126-132 (2002).
Ornelles, D.A. et al., "Localization of the adenovirus early region 1B 55-kilodalton protein during lytic infection: association with nuclear viral inclusions reques the early region 4 34-kilodalton protein," J. Virol. (1991) 424-39.
Pelletier et al., "Internal initiation of translation of eukaryotic mRNA directed by a sequence derived from poliovirus RNA," Nature 334, 1988, 320-325.
Piganeau, N. et al., "An allosteric ribozyme regulated by doxycycline," Angew. Chem. Int. Ed. (2000) 39(23):4369-4373.
Plumb, J.A. et al., "Pharmacodynamic response and inhibition of growth of human tumor xenografts by the novel histone deacetylase inhibitor PXD101," Mol. Cancer Ther. (2003) 2(8):721-728.
Querido, E. et al., "identification of three functions of the adenovirus E4orf6 protein that mediate p53 degradation by the E4orf6-E1B55K complex," J. Virol. (2001) 75(2):699-709.
Rajendra et al., "Differential effects of the breast cancer resistance protein on the cellular accumulation and cytotoxicity of 9-aminocamptothecin and 9-nitrocamptothecin," Cancer Res. (2003) 63(12):3228-3233.
Recchia, F. et al., "Multicentre phase II study of bifractionated CPT-11 with bimonthly leucovorin and 5-fluorouracil in patients with metastatic colorectal cancer pretreated with Folfox," Br. J. Cancer (2004) 91(8):1442-1446.
Rittner et al., "Conditional repression of the E2 transcription unit in E1-E3 deleted adenovirus vectors is correlated with a strong reduction in viral DNA replication and late gene expression in vitro," J. Virol. (1997) 71(4):3307-3311.
Rodriguez, R. et al., "Prostate attenuated replication competent adenovirus (ARCA) CN706: a selective cytotoxic for prostate-specific antigen-positive prostate cancer cells," Cancer Res. (1997) 57:2559-63.
Rogers et al., "Killing Epstein-Barr virus-positive B lymphocytes by gene therapy: comparing the efficacy of cytosine deaminase and herpes simplex virus thymidine kinase," Human Gene Ther. (1996) 7:2235-2245.
Rudinger, Peptide Hormones, Parsons, University Park Press, Baltimore (1976) 1-7.
Russell, W.C., "Update on adenovirus and its vectors," J. Virol. (2000) 81:2573-2604.
Safak et al., "Physical and functional interaction between the Y-box bdingin protein YB-1 and human polyomavirus JC virus large T antigen," J. Virol. (1999) 10146-10157.
Sandor, V. et al., "Phase I trial of the histone deacetylase inhibitor, depsipeptide (FR90122 NSC 630176) in patients with refractory neoplasms," Clin. Cancer Res. (2002) 8(3):718-728.
Sato, N. et al., "FR901228, a novel histone deacetylase inhibitor, incudes cell cycle arrest and subsequent apoptosis in refractory human pancreatic cancer cells," Int. J. Oncol. (2004) 24(3):679-685.
Shen, Y. et al., "Analyses of single-amino substitution mutants of adenovirus type 5 e1B-55K protein," J. Virol. (2001) 75(9):4297-4307.
Shenk, T.: Adenoviridae: The virus and their replication. Fields Virology, 3rd edition, edit. Fields, B.N. Knipe, D.M., Howley, P.M. et al., Lippincott-Raven Publishers, Philadelphia, chapter 67 (1996).
Shibahara et al., "Nuclear expression of the Y-box bindnig protein, NB-1, as a novel marker of disease progression in non-small cell lung cancer," Clin. Cancer Res. (2001) 7:3151-3155.
Shibao, K. et al., "Enhanced coexpression of YB-1 and DNA topoisomerase II agr genes in human colorectal carcinomas," Int. J. Cancer (1999) 83(6):732-737.

(56) References Cited

OTHER PUBLICATIONS

Skolnick et al.., "From genes to protein structure and function: novel applications of computational approaches in the genomic era," Trends in Biotech. (2000) 18:34-39.
Soff et al., "Expression of plasminogen activator inhibitor type 1 by human prostate carcinoma cells inhibits primary tumor growth, tumor-associated angiogenesis, and metastasis to lung and liver in an athymic mouse model," J. Clin. Invest. (1995) 96(6):2593-2600.
Steegenga, W.T. et al., "The large E1B protein together with the E4orf6 protein target p53 for active degradation in adenovirus infected cells," Oncogene (1998) 16:349-357.
Steenenga, W.T. et al., "Distinct regulation of p53 and p73 activity by adenovirus E1A, E1B, and E4orf6 proteins," Mol. Cell. Biol. (1999) 19(5):3885-3894.
Stein, U. et al., "Hyperthermia-induced nuclear transloation of transcription factor YB-1 leads to enhanced expression of multidrug resistance-related ABC transporters," Biol. Chem. (2001) 295(3):28562-28569.
Stiewe, T. et al., "Inactivation of reintoblastoma (RB) tumor suppressor by oncogenic isoforms of the p53 family member p73," J. Biol. Chem. (2003) 14230-36.
Su, Z-Z. et al., Melanoma differentiation associated gene-7, mda-7/IL-24, selectively induces growth suppression, apoptosis and radiosensitization in malignant gliomas in a p53-independent manner, Oncogene (2003) 22:1164-1180.
Sumantran et al., "Overexpression of Bcl-xS sensitizes MCF-7 cells to chemotherapy-induced apoptosis," Cancer Res. (1995) 55(12):2507-2512.
Sundararajan, R. et al., "E1B 19K blocks Bax oligomerization and tumor necrosis factor alpha-mediated apoptosis," J. virology (2001) 75(16):7506-7516.
Sutherland BW et al., "Akt phosphorylates the Y-box binding protein 1 at Ser102 located in the cold shock domain and affects the anchorage-independent growth of breast cancer cells," Oncogene, 2005, 24, 4281-4292.
Swaminathan, S. et al., "Regulation of adenovirus E2 transcription unit," Lucie Cancel Center, Northwestern University Medical School (1995) 177-194.
Swaminathan, S. et al., "Transactivation of adenovirus E2-early promoter by E1A and E4 6/7 in the context of viral chromosome," J. Mol. Biol. (1996) 258:736-46.
Swamynathan, S.K. et al., "Role of single-stranded DNA regions and Y-box proteins in transcriptional regulation of viral and cellular genes," FASEB J. (1998) 12(7):515-522.
Telling et al., "Absence of an essential regulatory influence of thea denovirus EBB 19-kilodalton protein on viral growth and early gene expression in human diploid W138, HeLa and A549 cells," J. Virology (1994) 68(1):541-547.
Thomas, C.E. et al., "Progress and problems with the use of viral vectors for gene therapy," Nature Reviews Genetics (2003) 4(5):346-358.
Tiainen et al., "Expression of E1A in terminally differentiated muscle cells reactivates the cell cycle and suppresses tissue-specific genes by separable mechanisms," Mol. Cell Biol. (1996) 16(10):5302-5312.
Ting et al., "YB-1 DNA-binding protein represses interferon activation of class II major histocompatibility complex genes," J. Exp. Med. (1994) 179:1605-1611.
Tollefson et al., Virology, 1996, vol. 220, Issue 1, pp. 152-162.
Tollefson, A.E. et al., "The adenovirus death protein (E3-11.6K) is required at very late stages of infection for efficient cell lysis and release of adenovirus from infected cells," J. Virol. (1996) 70:2296-2306.
Toth, K. et al., "Radiation increases the activity of oncolytic adenovirus cancer gene therapy vectors that overexpress the ADP (E3-11.6K) protein," Cancer Gene Ther. (2003) 10:193-200.
Tralhao et al., "In vivo selection and distant killing of cancer cells using adenovirus-mediated decorin gene transfer," FASEB J. (2003) 17(3):464-466.

Tsukada et al., "An E2F-responsive replication-selective adenovirus targeted to the defective cell cycle in cancer cells: potent antitumoral efficacy but no toxicity to normal cell," Cancer Res. (2002) 62(12):3438-3447.
Tuffariello, J. et al., "The adenovirus E3 14.7-kilodalton protein which inhibits cytolusis by tumor necrosis factor increases the virulence of vaccinia virus in a murine pneumonia model," J. Virol. (1994) 68(1):453-62.
Van Der Poel, "Smart Drugs in Prostate Cancer," European Urology, 2004, 1-17.
Van Hattum et al., "Induction of breast cancer resistance protein by the camptothecin derivative DX-8951f is associated with minor reduction of antitumour activity," British Journal of Cancer, 2002, 87, 665-672.
Verma et al., "Gene therapy—promise, problems and prospects," Nature (1997) 389:239-242.
Vigushin et al., "Trichostatin A is a histone deacetylase inhibitor with potent antitumor activity against breast cancer in vivo," Clin. Cancer Res. (2001) 7(4):971-976.
Vijayakrishna K. Gadi et al., "A Long-Acting Suicide Gene Toxin, 6-Methylpurine, Inhibits Slow Growing Tumors after a Single Administration," J. Pharmacol. Exp. Ther., 304: 1280-1284 (2003).
Vile et al., "Cancer gene therapy: hard lessons and new courses," Gene Therapy (2000) 7:2-8.
Vorburger, S.A. et al., "Adenoviral gene therapy," The Oncologist (2002) 7:46-59.
Weigel, S. et al., "The nuclear export signal within the E4orf6 protein of adenovirus type 5 supports virus replication and cytoplasmic accumulation of viral mRNA," J. Virol. (2000) 74(2):764-72.
Whittaker, G.R. et al., "Nuclear import and export of viruses and virus genomes," Virology (1998) 246(1);1-23.
Whyte et al., "Association between an oncogene and an anti-oncogene: the adenovirus E1A proteins bind to the retinoblastoma gene product," Nature, 334: 124-129 (1988).
Whyte, P. et al., "Cellular targets for transformation by the adenovirus E1A proteins," Cell (1989) 56(1):67-75.
Wijnholds, J., "Drug resistance caused by multidrug resistance-associated proteins," Novartis Found. Symp., 243: 69-82 (2002).
Wilhelm, S.M. et al., "BAY 43/9006 exhibits broad spectrum oral antitumor activity and targets the RAF/MEK/ERK pathway and receptor tyrosine kinases involved in tumor progression and angiogenesis," Cancer Res. (2004) 64(19):7099-7109.
Wittman, S. et al., "Flavopiridol down-regulates antiapoptotic proteins and sensitizes human breast cancer cells to epothilone B-induced apoptosis," Cancer Res. (2003) 63: 93-99.
Wong, H.K. et al., "Complementary functions of E1a conserved region 1 cooperate with conserved region 3 to activate adenovirus serotype 5 early promoters," J. Virol. (1994) 68(8):4910-20.
Wybranietz, W.A. et al., "Enhanced suicide gene effect by adenoviral transduction of a VP22-cytosine deaminase (CD) fusion gene," Gene Therapy (2001) 8(21):1654-1664.
Xiao-Song, H. et al., "Construction of adenoviral and retroviral vectors coexpressing the genes encoding the hepatitis B surface antigen and B7-1 protein," Gene (1996) 175:121-125.
Yamaguchi, T. et al., "Enhancement of thymidine kinase-mediated killing of malignant glioma by BimS, a Bh3-only cell death activator," Gene Ther. (2003) 10:375-85.
Yin D. et al., "Signaling pathways involved in induction of GADD45 gene expression and apoptosis by troglitazone in human MCF-7 breast carcinoma cells," Oncogene, 2004, 23(26):4614-23.
Yoneda, Y., "How proteins are transported from cytoplasm to the nucleus," J. Biochem. (1997) 121(5):811-817.
You et al., "ONYX-015 works synergistically with chemotherapy in lung cancer cell lines and primary cultures freshly made from lung cancer patients," Cancer Res. (2000) 60;1009-1013.
Yun et al., "p53 negatively regulates cdc2 transcription via the CCAAT-binding NF-Y transcription factor," J. Biol. Chem. (1999) 274(42):29677-29682.
Zambetti, G.P. et al., "A comparison of the biological activities of wild-type and mutant p53," FASEB J. (1993) 7(10):855-865.

(56) References Cited

OTHER PUBLICATIONS

Zhang et al., "Monogene and polygene therapy for the treatment of experimental prostate cancers by use of apoptotic genes bax and bad driven by the prostate-specific promoter ARR2PB," Hum. Gene Ther. (2002) 13(17):2051-2064.
Zhang, H. et al., "Therapeutic monoclonal antibodies for the ErbB family of receptor tyrosine kinases," Cancer Biol. Ther. (2003) 2(4):Supp. 1:S122-6.
Zhang, J. et al., "Identification of human uroplakin II promoter and its use in the construction of CD8840, a urothelium-specific adenovirus variant that eliminates established bladder tumors in combination with Docetaxel," Cancer Res. (2002) 62:3743-50.
Zhang, R. et al., "Gene therpay of a rat follicular thyroid carcinoma model with adenoviral vectors transducing murine interleukin-12," Endocrinology (2003) 144(4):1393-98.
Zhang, X. et al., "Adenoviral-mediated retinoblastoma 94 produces rapid telomere erosion, chromosomal crisis, and caspase-dependent apoptosis in bladder cancer in immortalized human urothelial cells but not in normal urothlial cells," Cancer Res. (2003) 63:760-65.
International Search Report for Application No. PCT/EP03/11427 dated Apr. 15, 2004 (10 pages).
International Preliminary Examination Report for Application No. PCT/EP03/11427 dated Mar. 11, 2005 (translation).
International Search Report for Application No. PCT/EP01/15212 dated Sep. 3, 2002 (20 pages).
International Preliminary Examination Report for Application No. PCT/EP2001/015212 dated Apr. 17, 2003 (translation).
International Search Report for Application No. PCT/EP03/05583 dated Oct. 6, 2003 (14 pages).
International Preliminary Examination Report for Application No. PCT/EP2003/005583 dated Sep. 2, 2004 (translation).
International Search Report for Application No. PCT/EP02/11527 dated Apr. 23, 2003 (10 pages).
International Preliminary Examination Report for Application No. PCT/EP02/11527 dated Oct. 23, 2003 (translation).
International Search Report for Application No. PCT/EP2004/012930 dated May 18, 2005 (4 pages).
International Preliminary Report on Patentability for Application No. PCT/EP2004/012930 dated May 14, 2006 (10 pages) translation.
International Search Report for Application No. PCT/EP2004/12931 dated Jul. 29, 2005 (7 pages).
International Preliminary Report on Patentability for Application No. PCT/EP2004/012931 dated May 14, 2006 (11 pages) translation.
International Search Report for Application No. PCT/DE00/01978 dated Mar. 2, 2001 (7 pages).
International Preliminary Examination Report for Application No. PCT/DE00/01978 dated Aug. 3, 2001 (9 pages) translation.
International Search Report for Application No. PCT/EP2006/000010 dated Oct. 2, 2006.
International Preliminary Report on Patentability for Application No. PCT/EP2006/000010 dated Apr. 10, 2007 (9 pages) translation.
United States Patent Office Notice of Allowance for U.S. Appl. No. 10/451,210 dated May 11, 2012 (5 pages).
United States Patent Office Action for U.S. Appl. No. 10/451,210 dated Sep. 7, 2011 (11 pages).
United States Patent Office Action for U.S. Appl. No. 10/451,210 dated May 25, 2010 (10 pages).
United States Patent Office Action for U.S. Appl. No. 10/451,210 dated Apr. 2, 2009 (11 pages).
United States Patent Office Action for U.S. Appl. No. 10/451,210 dated Jan. 9, 2008 (10 pages).
United States Patent Office Action for U.S. Appl. No. 10/451,210 dated Jan. 23, 2007 (13 pages).
United States Patent Office Action for U.S. Appl. No. 12/368,121 dated Jun. 1, 2012 (9 pages).
United States Patent Office Action for U.S. Appl. No. 12/368,121 dated Sep. 15, 2011 (15 pages).
United States Patent Office Notice of Allowance for U.S. Appl. No. 10/492,802 dated Apr. 6, 2009 (6 pages).
United States Patent Office Action for U.S. Appl. No. 10/492,802 dated Jun. 18, 2008 (7 pages).
United States Patent Office Action for U.S. Appl. No. 10/492,802 dated Sep. 18, 2007 (18 pages).
United States Patent Office Notice of Allowance for U.S. Appl. No. 12/498,208 dated Aug. 22, 2014 (8 pages).
United States Patent Office Action for U.S. Appl. No. 12/498,208 dated Jan. 2, 2014 (14 pages).
United States Patent Office Action for U.S. Appl. No. 12/498,208 dated Nov. 20, 2012 (9 pages).
United States Patent Office Action for U.S. Appl. No. 12/498,208 dated Nov. 2, 2011 (10 pages).
United States Patent Office Action for U.S. Appl. No. 12/498,208 dated Mar. 1, 2011 (12 pages).
United States Patent Office Action for U.S. Appl. No. 10/515,238 dated Oct. 28, 2009 (17 pages).
United States Patent Office Action for U.S. Appl. No. 12/769,435 dated Jul. 2, 2015 (6 pages).
United States Patent Office Action for U.S. Appl. No. 12/769,435 dated May 20, 2014 (10 pages).
United States Patent Office Action for U.S. Appl. No. 12/769,435 dated Sep. 9, 2013 (10 pages).
United States Patent Office Action for U.S. Appl. No. 12/769,435 dated Oct. 18, 2012 (9 pages).
United States Patent Office Action for U.S. Appl. No. 12/769,435 dated Mar. 13, 2012 (9 pages).
United States Patent Office Notice of Allowance for U.S. Appl. No. 10/531,366 dated Oct. 7, 2014.
United States Patent Office Action for U.S. Appl. No. 10/531,366 dated Mar. 27, 2014.
United States Patent Office Action for U.S. Appl. No. 10/531,366 dated Jun. 21, 2013.
United States Patent Office Action for U.S. Appl. No. 10/531,366 dated Mar. 3, 2011.
United States Patent Office Action for U.S. Appl. No. 10/531,366 dated Apr. 28, 2010.
United States Patent Office Action for U.S. Appl. No. 10/531,366 dated Jul. 21, 2009.
United States Patent Office Notice of Allowance for U.S. Appl. No. 10/531,366 dated Jan. 16, 2009.
United States Patent Office Action for U.S. Appl. No. 10/531,366 dated Feb. 14, 2008.
United States Patent Office Action for U.S. Appl. No. 10/579,507 dated Aug. 4, 2009 (16 pages).
United States Patent Office Action for U.S. Appl. No. 10/579,507 dated Oct. 28, 2008 (13 pages).
United States Patent Office Action for U.S. Appl. No. 12/699,347 dated Jan. 21, 2011 (14 pages).
United States Patent Office Action for U.S. Appl. No. 10/579,543 dated Jul. 20, 2009 (14 pages).
United States Patent Office Action for U.S. Appl. No. 10/579,543 dated Oct. 2, 2008 (11 pages).
United States Patent Office Notice of Allowance for U.S. Appl. No. 12/690,729 dated Jun. 25, 2013 (8 pages).
United States Patent Office Action for U.S. Appl. No. 12/690,729 dated Mar. 16, 2012 (5 pages).
United States Patent Office Action for U.S. Appl. No. 12/690,729 dated Jun. 28, 2011 (7 pages).
United States Patent Office Action for U.S. Appl. No. 10/834,641 dated Jan. 12, 2012 (11 pages).
United States Patent Office Action for U.S. Appl. No. 10/834,641 dated May 11, 2011 (10 pages).
United States Patent Office Action for U.S. Appl. No. 10/834,641 dated Sep. 20, 2010 (19 pages).
United States Patent Office Action for U.S. Appl. No. 10/834,641 dated Jan. 20, 2010 (13 pages).
United States Patent Office Action for U.S. Appl. No. 10/834,641 dated Jul. 13, 2009 (12 pages).
United States Patent Office Action for U.S. Appl. No. 10/834,641 dated Oct. 9, 2008 (11 pages).

(56) References Cited

OTHER PUBLICATIONS

United States Patent Office Action for U.S. Appl. No. 10/834,641 dated Aug. 30, 2007 (9 pages).
United States Patent Office Action for U.S. Appl. No. 10/834,641 dated Dec. 22, 2006 (8 pages).
United States Patent Office Action for U.S. Appl. No. 10/834,641 dated Apr. 11, 2006 (22 pages).
United States Patent Office Action for U.S. Appl. No. 10/834,641 dated Aug. 8, 2005 (19 pages).
United States Patent Office Action for U.S. Appl. No. 13/186,248 dated Jan. 3, 2014.
United States Patent Office Action for U.S. Appl. No. 13/186,248 dated Mar. 7, 2013.
United States Patent Office Action for U.S. Appl. No. 13/186,248 dated Mar. 13, 2015 (10 pages).
United States Patent Office Action for U.S. Appl. No. 11/813,089 dated Jan. 21, 2011 (25 pages).
United States Patent Office Action for U.S. Appl. No. 13/186,290 dated Apr. 1, 2014 (10 pages).
United States Patent Office Action for U.S. Appl. No. 13/186,290 dated Dec. 20, 2012 (15 pages).
United States Patent Office Action for U.S. Appl. No. 13/186,290 dated Apr. 5, 2012 (28 pages).
United States Patent Office Action for U.S. Appl. No. 13/186,290 dated Feb. 26, 2016 (9 pages).
United States Patent Office Action for U.S. Appl. No. 12/769,435 dated Mar. 23, 2016 (6 pages).
United States Patent Office Notice of Allowance for U.S. Appl. No. 12/769,435 dated Dec. 6, 2016 (9 pages).
United States Patent Office Office Action for U.S. Appl. No. 14/850,373 dated Jan. 6, 2017 (12 pages).
United States Patent Office Action for U.S. Appl. No. 12/769,435 dated Apr. 20, 2017 (7 pages).

\* cited by examiner

| | CR1 | | CR2 | CR3 | | |
|---|---|---|---|---|---|---|
| N | | | | | | C |
| 1 | 40 | 80 | 120 | 139 | 188 | 289 | dl520

| | CR1 | | CR2 | | |
|---|---|---|---|---|---|
| N | | | | | C |
| 1 | 40 | 80 | 120 | 139 | 186 | 289 | dl1119/1131

| | | |
|---|---|---|
| N | | |
| 1 | 3 | |

| CR3 | |
|---|---|
| | C |
| 139 | 218 |

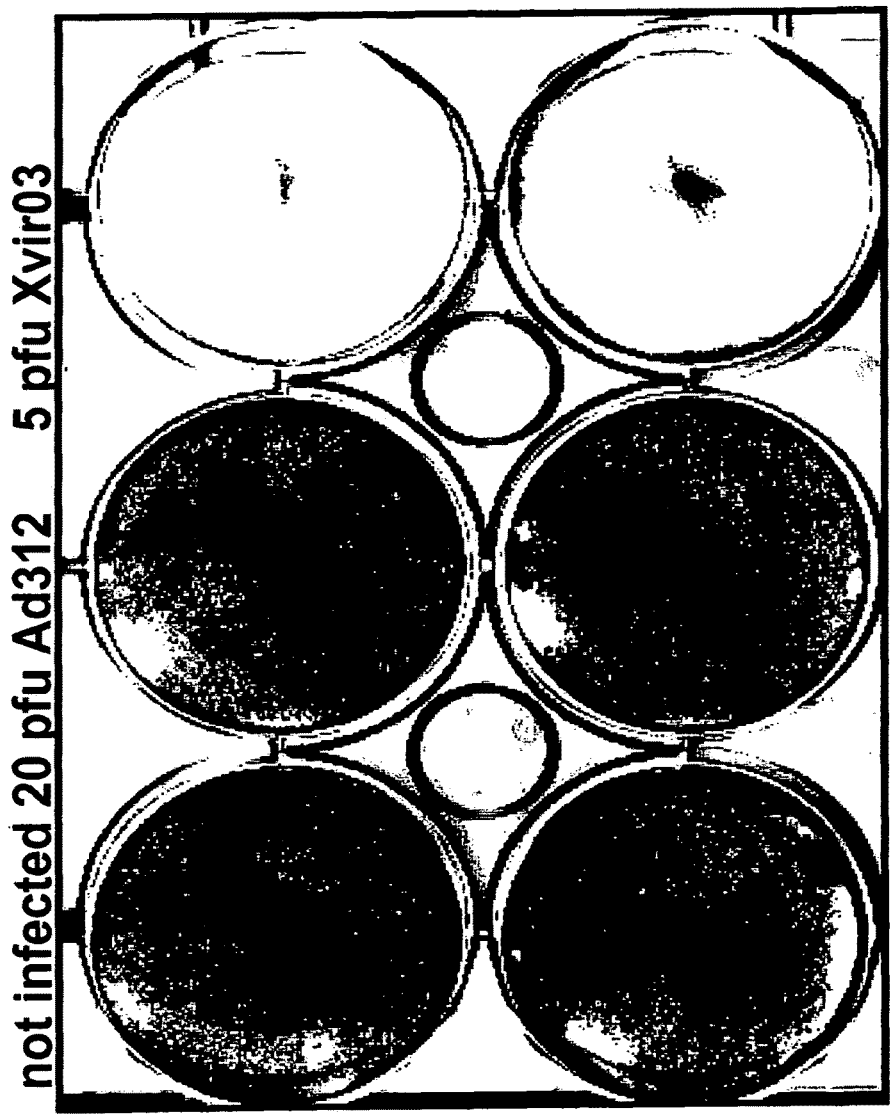

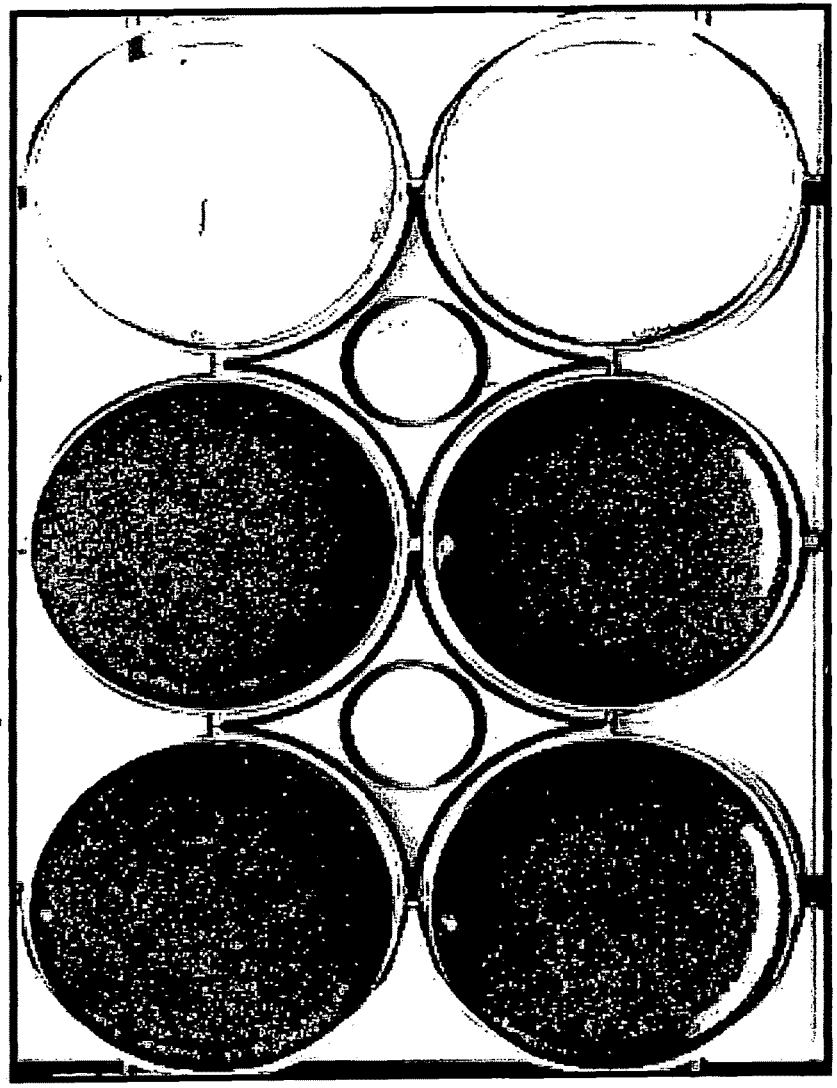

USE OF ADENOVIRUS AND NUCLEIC ACIDS CODING THEREFOR

CROSS-REFERENCE TO RELATED APPLICATION(S)

This is a divisional of U.S. patent application Ser. No. 12/769,435, filed on Apr. 28, 2010, which is a continuation of U.S. patent application Ser. No. 10/515,238, filed on Aug. 4, 2005, which is a U.S. national stage entry of International Patent Application No. PCT/EP2003/005583, filed on May 27, 2003, which claims priority to German Patent Application No. 10322530.7, filed on May 19, 2003, German Patent Application No. 10248039.7, filed on Oct. 15, 2002, German Patent Application No. 10225400.1, filed on Jun. 7, 2002, and German Patent Application No. 10223534.1, filed on May 27, 2002, the entire contents of all of which are fully incorporated herein by reference.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on May 23, 2017, is named "H10010_US_C-II-030265-1006-US02-SEQ-LIST-05-23-17.txt" and is 1,295 bytes in size.

The present invention relates to the use of adenoviruses as well as to nucleic acids coding therefor and recombinant viral oncoprotein.

A number of therapeutic concepts are currently used in the treatment of tumors. Apart from using surgery, chemotherapy and radiotherapy are predominant. All these techniques are, however, associated with considerable side effects. The use of replication selective oncolytic viruses provides for a new platform for the treatment of tumors. In connection therewith a selective intratumor replication of a viral agent is initiated which results in virus replication, lysis of the infected tumor cell and spreading of the virus to adjacent tumor cells. As the replication capabilities of the virus is limited to tumor cells, normal tissue is spared from replication and thus from lysis by the virus.

For the time being, several viral systems are subject to clinic trials aiming at tumor lysis. One example for such an adenovirus is dl1520 (Onyx-015) which has been successfully used in clinical phases I and II (Khuri, F. et al. Nature Medicine 6, 879-885, 2000). Onyx-015 is an adenovirus having a completely deleted E1B55kDa gene. The complete deletion of the E1B55kDa protein of the adenovirus is based on the discovery that replication and thus lysis of cells is possible with an adenoviral vector having a p53 deficiency (Kim, D. et al., Proc. Am. Soc. Clin. Oncol. 17, 391a, 1998), whereby normal cells are not harmed. More particularly, the E1B55kDa gene product is involved in the inhibition of p53, the transport of viral mRNA and the switching off the protein synthesis of the host cell. The inhibition of p53 occurs via formation of a complex consisting of p53 and the adenoviral coded E1B55kDa protein and/or a complex consisting of E1B55kDa and E4orf6. p53, coded by TP53, is the starting point for a complex regulatory mechanism (Zambetti, G. P. et al., FASEB J. 7, 855-865, 1993), which results, among others, in an efficient inhibition of the replication in the cell of viruses like adenovirus. The gene TP 53 is deleted or mutated in about 50% of all human tumors which results in the absence of—desired—apoptosis due to chemotherapy or radiation therapy resulting in an usually unsuccessful tumor treatment A further concept of tumorlytic adenoviruses is based on the discovery that if the E1A protein is present in a specific deleted form or comprises one or several mutations, which do not affect the binding of Rb/E2F and/or p107E2F and/or p130/E2F, such adenovirus will not induce the entry of the infected cells into the S phase and will be capable of replicating in tumor cells which do not have a functional Rb protein. Additionally, the E1A protein can be deleted at the N-terminus and comprise one or several mutations in the region of amino acid positions 1 to 76 of the E1A proteins, respectively, in order to inhibit the binding of E1A to p300 and thus to provide for a selective replication in tumor cells. These approaches are described in an exemplary manner in European patent EP 0 931 830. Examples for such viruses are AdΔ24, dl922-947, E1Ad/01/07 and CB016 (Howe, J. A. et al., Molecular Therapy 2, 485-495, 2000; Fueyo, J. et al., Oncogene 19, 2-12, 2000; Heise, C. et al., Nature Medicine 6, 11341139, 2001; Balague, C. et al., J. Virol. 75, 7602-7611, 2001). These adenoviral systems for oncolysis known in the prior art thus comprise distinct deletions in the E1A protein, whereby such deletions had been made under the assumption that a functional Rb protein and complexes consisting of inactive Rb protein and E2F, respectively, would block an efficient in vivo replication and in order to provide an adenoviral replication in vivo in Rb-negative/mutated cells only. These adenoviral systems according to the prior art are based on E1A in order to control in vivo replication using the early E2 promoter (engl E2 early promoter) and free E2F (Dyson, N. Genes & Development, 12, 2245-2262, 1998).

A further form of tumorlytic adenoviral systems is based on the use of selective promoters for specifically expressing the viral oncogene E1A which provides for a selective replication in tumor cells (Rodriguez, R. et al., Cancer Res. 57, 2559-2563, 1997).

As described above, the selection of a cellular background which is appropriate for the respective concept underlying the mode of action is important for the various concepts of adenoviral tumorlytic viruses. In other words, the various adenoviral systems currently known may only be used if distinct molecular biological prerequisites are realized. This limits the use of such systems to distinct patient groups.

A particular problem in the treatment of tumor diseases arises once the patients develop a so-called multidrug resistance (engl. multidrug resistance (MDR)) which represents a particularly well studied form of resistance of tumors against cytostatics (Gottesman and Pastan. Annu Rev. Biochem. 62, 385-427, 1993). It is based on the overexpression of the membrane-bound transport protein P-glycoprotein which belongs to the so-called ABC transporters (Stein. U. et al., JBC 276, 28562-69, 2001, J. Wijnholds, Novartis Found Symp., 243, 69-79, 2002). Bargou, R. C. et al and Oda, Y. et al (Bargou, R. C. et al., Nature Medicine 3, 447-450, 1997; Clin. Cancer Res. 4, 2273-2277, 1998) were able to show that nuclear localisation of the human transcription factor YB-1 is directly involved in the activation of the expression of the P-glycoprotein. Further studies confirmed that YB-1 is transported into the nucleus by various stress conditions such as UV irradiation, administration of cytostatics (Koike. K. et al., FEBS Lett 17, 390-394, 1997) and hyperthermia (Stein, U. et al., JBC 276, 28562-69, 2001). Further studies confirmed that the nuclear localisation of YB-1 has an impact on one further ABC transporter. This ABC transporter is referred to as MRP (engl multidrug resistance-related protein) and is involved in the formation of the so-called atypical non-P-glycoprotein dependent multidrug resistance (Stein, U. et al., JBC 276, 28562-69, 2001).

The problem underlying the present invention is to provide a technical teaching and in particular a means which allows to treat an organism, more particularly a human organism and a group of patients, respectively, specifically with tumorlytically active agents. It is a further problem underlying the present invention to provide a means which is suitable to cause tumorlysis in patients having tumor diseases which are resistant to cytostatics, particularly those which have a multidrug resistance.

According to the present invention the problem is solved in a first aspect by the use of a virus, preferably an adenovirus, for the manufacture of a medicament, whereby the virus is replication deficient in cells which do not have YB-1 in the nucleus, and the virus codes for an oncogene or oncogene product, preferably an oncogene protein, which transactivates at least one viral gene in YB-1 nucleus positive cells, preferably an adenoviral gene, whereby the gene is selected from the group comprising E1B55kDa, E4orf6, E4orf3 and E3ADP.

In a second aspect, the problem is solved by the use of a virus, preferably an adenovirus, for the replication in cells which have YB-1 in the nucleus, whereby the virus is replication deficient in cells which do not have YB-1 in the nucleus and the virus codes for an oncogene or oncogene product, in particular oncogene protein, which transactivates at least one viral gene, preferably an adenoviral gene, whereby the gene is selected from the group comprising E1B55kDa, E4orf6. E4orf3 and E3ADP.

In an embodiment of the two uses according to the invention, the virus, preferably the adenovirus, replicates in cells which have YB-1 in the nucleus.

In a further embodiment of the two uses according to the invention the viral oncogene protein is E1A and/or the oncogene is the gene coding for E1A and/or the oncogene protein is E1A.

In a preferred embodiment the viral oncogene protein E1A is capable of binding to a functional Rb tumor suppressor gene product.

In an alternative embodiment the viral oncogene protein E1A is not capable of binding to a functional Rb tumor suppressor gene product.

In a further embodiment of the two uses according to the invention the viral oncogene protein E1A is not inducing nuclear localisation of YB-1.

In a still further embodiment of the two uses according to the invention the medicament is for patients the cells of whom are either Rb-positive or Rb-negative.

In a preferred embodiment the cells are those cells which are involved in the formation of the condition which is to be influenced by the medicament.

In a further embodiment of the two uses according to the invention the cells are Rb-negative and are YB-1 positive in the nucleus, preferably are YB-1 positive in the nucleus independent from the cell cycle.

In a still further embodiment of the two uses according to the invention the medicament is for the treatment of tumors.

In a still further embodiment of the two uses according to the invention the cells, particularly the cells forming the tumor or parts thereof, are resistant to drugs, in particular have a multidrug resistance, preferably a resistance against anti-tumor agents and more preferably against cytostatics.

In a preferred embodiment of the two uses according to the invention the cells are expressing, preferably overexpressing the membrane-bound transport protein P-glycoprotein and/or MRP.

In a further embodiment of the two uses according to the invention the cells are p53-positive or p53-negative.

In an embodiment of the two uses according to the invention the oncogene protein has, compared to the wild-type oncogene protein E1A, one or several mutations or deletions, whereby the deletion is preferably selected from the group comprising deletions of the CR3 region and deletions of the N-terminus and deletions of the C-terminus. In connection therewith it is preferred that the E1A oncogene protein can bind to Rb.

In a further embodiment of the two uses according to the invention the oncogene protein has, compared to the wild-type oncogene protein, one or several mutations or deletions, whereby the deletion is preferably in the CR1 region and/or the CR2 region. It is within the invention that the oncogene protein E1A is incapable of binding to Rb.

In an embodiment of the two uses according to the invention the viral oncogene protein, in particular E1A, is under the control of a tissue-specific and/or tumor-specific promoter.

In a further embodiment of the two uses according to the invention, the virus, in particular the adenovirus, codes for YB-1.

In a still further embodiment of the two uses according to the invention, YB-1 is under the control of a tissue-specific and/or tumor-specific promoter.

In a preferred embodiment of the two uses according to the invention, the virus, in particular the adenovirus, codes at least for one protein which is selected from the group comprising E4orf6, E4orf3, E1B55kDa and adenoviral E3ADP protein.

In an alternative embodiment of the two uses according to the invention, the cells have YB-1 in the nucleus, in particular the cells forming the tumor or part thereof have YB-1 in the nucleus.

In a further embodiment of the two uses according to the invention, the tumor has YB-1 in the nucleus upon inducing the transport of YB-1 into the nucleus.

In a preferred embodiment of the two uses according to the invention, the transport of YB-1 into the nucleus is triggered through at least one measure selected from the group comprising radiation, administration of cytostatics and hyperthermia.

In a particularly preferred embodiment of the two uses according to the invention, the measure is applied to a cell, an organ or an organism.

In a preferred embodiment of the two uses according to the invention, the virus, in particular the adenovirus, is selected from the group comprising AdΔ24, d1922-947, E1Ad/01/07, d11119/1131, CB 016, d1520 and viruses which are lacking an expressed viral E1A oncogene which is capable of binding a functional Rb tumor suppressor gene product.

In a third aspect the problem is solved by the use of a virus, preferably an adenovirus, for the manufacture of a medicament, whereby the virus, preferably the adenovirus, is designed such that the replication is controlled through or by means of YB-1 through the activation of the E2-late promoter, preferably predominantly through the activation of the E2-late promoter. In an embodiment YB-1 is either a transgenic YB-1 or a cellular, in particular cellular deregulated YB-1. A transgenic YB-1 is preferably meant to be a YB-1 which is expressed in a cell by a vector, preferably a or the adenovirus. The E2-late promoter is preferably the adenoviral E2-late promoter as present in the wildtype adenovirus, or an E2-late promoter as described herein in connection with the expression of transgenes.

In a fourth aspect the problem is solved by the use of a virus and particular an adenovirus, for the replication in cells which have YB-1 in the nucleus, whereby the virus, in particular the adenovirus, is designed such that the replication is controlled by YB-1 through the activation of the E2-late promoter, preferably predominantly through the activation of the E2-late promoter. In an embodiment YB-1 is either a transgenic YB-1 or a cellular, in particular cellular deregulated YB-1. A transgenic YB-1 as used herein is preferably a YB-1 which is expressed in a cell by a vector, preferably a or the adenovirus. The E2-late promoter is preferably the adenoviral E2-late promoter as present in the wildtype adenovirus, or an E2-late promoter as described herein in connection with the use of the expression of transgenes.

In a preferred embodiment of the third and/or fourth aspect of the present invention the adenovirus is designed such as disclosed herein, particularly such as it is designed in order to be used in accordance with the present invention.

In a fifth aspect the problem is solved by a viral oncogene protein, in particular an isolated viral oncogene protein which has the following characteristics:
 a) transactivation of at least one viral gene in YB-1 nucleus-positive cells, which is selected from the group comprising E1B55kDa, E3ADP and E4orf6 and E4orf3; and
 b) lacking induction of YB-1 in the nucleus, in particular in the nucleus of the cell in which the viral oncogene protein is present.

In an embodiment the viral oncoprotein is E1A.

In a further embodiment the viral oncogene protein has, compared to the wildtype oncogene protein, one or several mutations or deletions, whereby the deletion is preferably selected from the group comprising deletion of the CR3 region, deletion of the N-terminus and deletion of the C-terminus.

In an embodiment the induction of YB-1 through the viral oncogene protein is absent when E4orf6 and/or E1B55kDa are not present in the nucleus exhibiting cell.

In connection therewith it is intended that the viral oncogene protein is capable of binding to Rb.

In an alternative embodiment the viral oncogene protein comprises one or several mutations or deletions, whereby the deletion is preferably in the CR1 region and/or the CR2 region of the E1A oncogene protein. In connection therewith it is intended that the viral oncogene protein is not able to bind to Rb.

In a sixth aspect the invention is related to the use of a viral replication system, preferably an adenoviral replication system, comprising a nucleic acid which codes for a virus, in particular an adenovirus as used in accordance with the present invention, and comprising one nucleic acid of a helper virus, whereby the nucleic acid of the helper virus comprises a nucleic acid which codes for YB-1.

In an embodiment the viral nucleic acid, in particular the adenoviral nucleic acid, and/or the nucleic acid of the helper virus are present as a vector which can replicate.

In a seventh aspect the invention is related to the use of a nucleic acid coding for a virus, in particular an adenovirus, as it is used in accordance with the invention, for the manufacture of a medicament, in particular for the manufacture of a medicament for the treatment of tumors.

In an embodiment the cells, in particular the cells forming the tumor or parts thereof, are resistant, in particular have a multidrug resistance, against drugs, preferably anti-tumor agents, and more preferably cytostatics.

In an eighth aspect the invention is related to the use of a nucleic acid which codes for a virus, in particular an adenovirus, as is used in accordance with the present invention, for the replication in cells which have YB-1 in the nucleus, whereby the virus is replication deficient in cells which do not have YB-1 in the nucleus, and the virus codes for an oncogene or oncogene product which transactivates at least one viral gene, preferably an adenoviral gene, in YB-1 nucleus-positive cells, whereby the gene is selected from the group comprising E1B55kDa, E4orf6, E4orf3 and E3ADP.

In a ninth aspect the problem is solved by the use of a nucleic acid which codes for a virus, preferably an adenovirus, as is used in accordance with the invention, for the manufacture of a medicament, whereby the virus is designed such that the replication is controlled by YB-1 through the activation of the E2-late promoters, preferably predominantly through the activation of the E2-late promoter. In an embodiment the YB-1 is either a transgenic YB-1 or a cellular, in particular cellular deregulated YB-1. A transgenic YB-1 as used herein is preferably a YB-1 which is expressed in a cell by a vector, preferably a or the adenovirus. The E2-late promoter is preferably the adenoviral E2-late promoter as is present in the wildtype adenovirus, or an E2-late promoter as described herein in connection with the use of the expression of transgenes.

In a tenth aspect the problem is solved by the use of a nucleic acid which codes for a virus, in particular an adenovirus, as used in accordance with the invention for replication in cells, whereby the virus is designed such that the replication is controlled by YB-1 through the activation of the E2-late promoter, preferably predominantly through the activation of the E2-late promoter. In an embodiment the YB-1 is either a transgenic YB-1 or a cellular, in particular cellular deregulated YB-1. As used herein, transgenic YB-1 is preferably a YB-1 which is expressed by a vector in a cell, preferably by a or the adenovirus. The E2-late promoter is preferably the adenoviral E2-late promoter as present in wildtype adenovirus, or an E2-late promoter as used in connection with the expression of transgenes described herein.

In an eleventh aspect the problem is solved by the use of a vector comprising one of the previously described nucleic acids, for the use in accordance with the first or second aspect of the present invention.

In a twelfth aspect the invention is related to the use of an agent interacting with YB-1 for the characterisation of cells, cells of a tumor tissue or patients, in order to determine whether these shall be contacted and/or treated with a virus, in particular an adenovirus, which is used in accordance with the invention.

In an embodiment the agent is selected from the group comprising antibodies, anticalines, aptamers, aptazymes and spiegelmers.

In a thirteenth aspect the problem is solved by the use of the viral oncogene protein according to the present invention or a nucleic acid coding therefor, for the manufacture of a virus, in particular an adenovirus, which is used in accordance with the first and second aspect of the present invention.

In an embodiment the virus comprises a nucleic acid coding for a transgene

In a further embodiment the virus comprises the translation product and/or the transcription product of a transgene.

In a preferred embodiment the nucleic acid of the adenoviral replication system and/or the nucleic acid of the helper virus comprises a transgene or a nucleic acid coding for a transgene.

In a still further embodiment the nucleic acid comprises a transgene or a nucleic acid coding for a transgene.

In an alternative embodiment the transgene is selected from the group comprising prodrug genes, cytokines, apoptosis-inducing genes, tumor suppressor genes, genes for metalloproteinases inhibitors and genes for angiogenesis inhibitors.

In an embodiment the transgene is selected from the group comprising nucleic acids for siRNA, for aptamers, for antisense molecules and for ribozymes, whereby the siRNA, the aptamers, the antisense molecules and/or the ribozymes are targeted against a target molecule.

In a further embodiment the target molecule is selected from the group comprising resistance relevant factors, anti-apoptosis factors, oncogenes, angiogenesis factors, DNA synthesis enzymes, DNA repair enzymes, growth factors and their receptors, transcription factors, metalloproteinases, in particular matrix metalloproteinases, and plasminogen activator of the urokinase type. In an embodiment the resistance-relevant factors are preferably selected from the group comprising P-glycoprotein. MRP and GST, and also comprise nucleic acids coding therefor. In an embodiment the anti-apoptosis factors are selected from the group comprising BCL2, and also comprise the nucleic acids coding therefor. In an embodiment the oncogenes are selected from the group comprising Ras, in particular mutated Ras, Rb and Myc, and also comprise nucleic acids coding therefor. In an embodiment the angiogenesis factors are selected from the group comprising VEGF and HMG proteins and also comprise the nucleic acids coding therefor. In an embodiment the DNA synthesis enzymes are selected from the group comprising telomerase and also comprise nucleic acids coding therefor. In an embodiment the DNA repair enzymes are selected from the group which comprises Ku-80, and also comprise nucleic acids coding therefor. In an embodiment the growth factors are selected from the group comprising PDGF, EGF and M-CSF, and comprise also nucleic acids coding therefor. In an embodiment the receptors are in particular receptors for growth factors, whereby the growth factors are preferably selected from the group comprising PDGF, EGF and M-CSF, and also comprise the nucleic acids coding therefor. In an embodiment the transcription factors are selected from the group comprising YB-1, and also comprise the nucleic acid coding therefor. In an embodiment the metalloproteinases are preferably matrix metalloproteinases. In a preferred embodiment the matrix metalloproteinases are selected from the group comprising MMP-1 and MMP-2, and also comprise the nucleic acids coding therefor. In an embodiment the plasminogen activators of the urokinase type are selected from the group comprising uPa-R, and also comprise the nucleic acids coding therefor.

In a still further embodiment the medicament comprises additionally at least one pharmaceutically active compound.

In a preferred embodiment the pharmaceutically active compound is selected from the group comprising cytokines, metalloproteinase inhibitors, angiogenesis inhibitors, cytostatics and cell cycle inhibitors.

The present invention is based on the surprising finding that the DNA replication of E1A-modified adenoviruses in YB-1 nucleus-positive tumor cells is based on the activation of the E2-late promoter. E1A-modified adenoviruses as used herein, are adenoviruses which (a) do not replicate in YB-1 nucleus-negative cells or show a reduced, preferably a strongly reduced replication in YB-1 nucleus-negative cells compared to the respective wildtype, (b) transactivate at least one viral gene, whereby the gene is in particular selected from the group comprising E1B55kDa, E4orf6, E4orf3 and E3ADP, and/or (c) do not translocate cellular YB-1 through the adenovirus into the nucleus. Optionally the adenoviruses used in accordance with the present invention have the further characteristic that the binding of the adenoviral encoded E1A protein interferes with the binding of E2F to Rb and is able to dissolve the respective complex consisting of E2F and Rb, respectively. Adenoviruses which have at least one or several of the aforementioned features a) to c), preferably all of features a) to c), are replication deficient in cells which do not have YB-1 in the nucleus.

In an embodiment a strongly reduced replication as used herein particularly means a replication which, compared to the wildtype, is reduced by a factor of 2, preferably by a factor of 5, more preferably by a factor of 10 and most preferably by a factor of 100. In a preferred embodiment such comparison of the replication is performed using identical or similar cell lines, identical or similar virus titers for infection (multiplicity of infection, MO, or plaque forming unit, pfu) and/or identical or similar general experimental conditions. Replication as used herein particularly means formation of particles. In a further embodiment the measure for replication can be the extent of viral nucleic acid synthesis. Methods for the determination of the extent of the viral nucleic acid synthesis as well as methods for determining particle formation are known to the ones skilled in the art.

The findings, methods, uses or nucleic acids, proteins, replication systems and the like described herein are not necessarily limited to adenoviruses. In principle, such systems exist also in other viruses which are herewith also comprised.

A replication which is comparable to wildtype replication, can be realized upon an infection rate of 1 to 10 pfu/cell compared to 10 to 100 pfu cell according to the prior art when using the viruses according to the present invention or when using the viruses described herein in accordance with the present invention.

Cellular YB-1 as used herein shall mean any YB-1 which is coded by a cell and preferably is also expressed by a cell, whereby this YB-1 is present in the cell, preferably prior to the infection of the respective cell with an adenovirus, preferably an adenovirus and/or a helpervirus as described herein. It is, however, also within the present invention that cellular YB-1 is a YB-1 which is introduced into the cell or produced by such cell upon application of exogenous measures such as, e. g., infection with a virus, in particular with an adenovirus.

Without wishing to be bound by this in the following, the present inventor assumes that the E2-early promoter, i. e. the early E2 promoter is not switched on through the human cellular E2F transcription factor in connection with the replication of the viruses used herein in accordance with the present invention. The switching on of the replication is independent of the Rb status of the cells, i. e. which means that the tumor cells which are infected using the viruses disclosed herein and which are preferably lysed subsequently thereafter, may comprise both functional as well as inactive Rb proteins. Additionally, adenoviral replication does neither need any functional p53 protein nor is it affected by its presence, when using the adenoviruses disclosed herein or under the conditions disclosed herein. Insofar, the technical teaching departs from the principle underlying the use of the oncolytic or tumorlytic adenoviruses of the AdΔ24, d1922-947, E1Ad/01/07, CB016 type or of those adenoviruses which are, for example, described in European patent EP 0 931 830, and into which one or several deletions have been introduced into the E1A protein under the assumption that intact functional Rb proteins are an obstacle to an efficient replication in vivo thus providing an adenoviral replication in vivo only in Rb-negative and Rb-mutated cells, respectively. These adenoviral systems according to the prior art are based on E1A in order to control in vive replication of adenoviruses by means of the early E2 promoter (E2 early promoter) and "free E2F". Nevertheless, these viruses according to the prior art may be used in accordance with the present invention, i. e. for replication in cells which contain YB-1 in the nucleus independent from the cell cycle.

The viruses described in said European patent EP 0 931 830 and in particular adenoviruses may be used in accordance with the present invention. More particularly, the viruses described in said patent are replication deficient and lack an expressed viral oncoprotein which is capable of binding a functional Rb tumor suppressor gene product. The adenovirus can particularly be an adenovirus which is lacking expressed viral E1A oncoprotein which is capable of binding a functional tumor suppressor gene product, in particular Rb. The viral E1A oncoprotein can comprise an inactivating mutation, for example in the CR1 domain at amino acid positions 30 to 85 in Ad 5, nucleotide positions 697 to 790 and/or the CR2 domain at amino acid positions 120 to 139 in Ad 5, nucleotide positions 920 to 967 which are involved in the binding of p105 Rb protein, p130 and p107 protein. It can also be intended that the adenovirus is of type 2 d1 312 or the adenovirus is of type 5 NT d1 1010.

Replication ultimately occurs in cells which comprise YB-1 in the nucleus, preferably independent from the cell cycle, which are thus YB-1 nucleus-positive, when using adenoviruses in accordance with the invention for the manufacture of a medicament, in particular for the manufacture of a medicament for the treatment of tumor diseases, and when using adenoviruses in accordance with the invention for replication in cells which have YB-1 in the nucleus. It is particularly noteworthy that the adenoviruses as such do not replicate in cells which do not have YB-1 in the nucleus but have YB-1 essentially in the cytoplasm only, or replicate at a significantly reduced level. Insofar it is necessary that YB-1 is present in the nucleus for a successful replication of these viruses. This can, for example, as will be outlined in the following in more detail, be realized by applying measures to the cells which result in the expression of YB-1 in the nucleus or in the presence of YB-1 in the nucleus. A respective measure can, for example, be the coding and expression, respectively, of YB-1 through adenoviruses used in accordance with the present invention which in addition to the adenoviral genes also comprise a genetic information coding for YB-1 and in particular for the expression of YB-1. Other measures which result in transport, induction or expression of YB-1 in the nucleus of the cell, are stress conditions such as administration of cytostatics, irradiation, hyperthermia and the like, to the cell and to an organism containing such cell.

The adenoviruses which are used in connection with the present invention, in particular for tumor lysis, are further characterized such that they do not replicate in cells which do not have YB-1 in the nucleus, in other words which are YB-1 nucleus-negative.

A further feature of the adenoviruses which are to be used in accordance with the invention, is that they code for a viral oncoprotein which is also referred to herein as oncogene protein, whereby the oncogene protein is preferably E1A, whereby the oncogene protein, is capable of activating at least one viral gene which can have an impact on the replication of the virus and/or cell lysis of the cells infected by the virus. It is preferred that the influence on replication is such that the virus replicates better in the presence of the oncogene protein compared to a situation where the oncogene protein of the respective virus is lacking. This process is referred to herein also as transactivating and in particular E1A transactivating, when the transactivation is mediated through E1A. The term "transactivate" or "transactivation" describes preferably the process that the respective viral oncoprotein has an impact on the expression and/or the transcription of one or several other genes different from the viral oncoprotein coding gene itself, i. e. is preferably controlling its expression and/or translation, and in particular activates this/these. Such viral genes are preferably E1B55kDa, E4orf6, E4orf3 and E3ADP as well as any combination of the aforementioned genes and gene products, respectively.

A further, although preferably optional, feature of the adenoviruses to be used in accordance with the invention, is the binding to and of tumor suppressor Rb. In principle it is within the present invention that the adenoviruses used in accordance with the present invention bind to Rb or do not bind to Rb. The use of both alternative embodiments of the adenoviruses is possible independently from the Rb status of the cell to be treated.

In order to confer the capability to not bind to Rb, the following deletions of the E1A oncoprotein are, for example, possible: Deletion in the CR1 region (amino acid positions 30-85 in Ad5) and deletion of the CR2 region (amino acid positions 120-139 in AD5). In doing so, the CR3 region is maintained and can have its transactivating function on the other early viral genes.

In contrast thereto, the following deletions to the E1A oncoprotein are in principle possible in order to impart E1A the capability to bind to Rb: deletion of the CR3 region (amino acid positions 140-185); deletion of the N-terminus (amino acid positions 1-29); deletion of amino acid positions 85-119, and deletion of the C-terminus (amino acid positions 186-289). The regions recited herein do not interfere with the binding of E2F to Rb. The transactivating function remains, however, is reduced compared to wildtype Ad5.

Such viruses which are known in the prior art are generally regarded as replication deficient. It is, however, the merit of the present inventor that he has recognised that they are capable of replication in a suitable background nevertheless, in particular a cellular background. Such a suitable cellular background is caused or provided by the presence of YB-1 in the nucleus, preferably a cell cycle independent presence of YB-1 in the nucleus. The term cells or cellular systems, as used herein, comprises fragments of cells or fractions of cell lysates as well as cells which are present in vitro, in vivo or in situ. Insofar, the term cellular systems or cells also comprises cells which are present in a cell culture, tissue culture, organ culture or in any other tissue or organ in vivo and in situ, respectively, isolated, in groups or as part of tissues, organs or organisms or are also present as such in a preferably living organism. The organism is preferably a vertebrate organism and more preferably a mammal. It is particularly preferred that the organism is a human organism.

Additionally, it is within the present invention that based on the technical teaching provided herein, new viruses are generated which have the replication characteristic of the adenoviruses described herein as well as the one of adenoviruses of the prior art in cells which are YB-1 nucleus-positive. In other words, preferably starting from the adenoviruses already known further viruses can be designed which have the features defined herein needed for their use in accordance with the present invention.

In connection with the present invention the modified E1A oncoprotein of the various adenoviruses which are to be used in accordance with the invention, is capable of transactivating the early viral genes such as, for example, E1B55kDa, E4orf3, E4orf6, E3ADP, in YB-1 nucleus-positive cells. In connection therewith, there are preferably otherwise no further changes to the viral genome and the respective adenovirus can otherwise correspond to an adenovirus of the wildtype or any derivative thereof.

The viruses disclosed herein which code for a transactivating oncogene protein in the sense of the present invention or which comprise such oncogene protein, comprise, for example, the adenoviruses AdΔ24, dl922-947. E1Ad01/07, CB106 and/or the adenoviruses described in European patent EP 0 931 380, which are each capable of transactivating the early genes, such as E1B. E2, E3 and/or E4, and are comparable to adenoviruses of the wildtype, in particular wildtype Ad5. A particular region of the E1A protein is responsible for transactivation in these cases. Within various adenovirus serotypes there are three highly conserved regions in the E1A protein. The CR1 region from amino acid positions 41-80, the CR2 region from amino acid positions 120-139 and the CR3 region from of amino acid positions 140-188. The transactivating function is primarily based on the presence of the CR3 region in the E1A protein. The amino acid sequence of CR3 is unaltered in the aforementioned adenoviruses. This results in a transactivation of the early genes E1B. E2, E3 and E4 independent from the presence of YB-1 in the nucleus or in the cytoplasma.

In the recombinant adenovirus dl520, however, the CR3 region has been deleted. Thus dl 1520 expresses a so-called E1A12S protein which does not comprise the amino acid sequence of the CR3 region. As a consequence, dl520 can exert a very weak transactivating function only, in particular on the E2 region, and thus does not replicate in YB-1 nucleus-negative cells. In YB-1 nucleus-positive cells YB-1 is transactivating the E2 region and thus allows an efficient replication of dl520. This is the basis for the use of systems like dl520 and of systems on the basis of dl520 for the purposes disclosed herein, respectively. A further important difference between both the previously described groups of adenoviruses, i. e. delta 24 (herein also referred to as AdΔ24) and dl520 resides in the fact that with dl520 the early genes E1B. E3 and E4 are more strongly transactivated in YB-1 nucleus-positive cells compared to YB-1 nucleus-negative cells. In contrast, there are no or only minor differences with delta 24. The transactivation effect of dl520 and more particularly of the E1A12S protein, however, is significantly reduced compared to wildtype adenovirus. This transactivation is, however, sufficient in order to allow for an efficient replication in YB-1 nucleus-positive cells, as shown in example 10. The design of the E1A protein and of the nucleic acid coding therefor described herein and in particular in this context such that the E1A protein has one or several deletions and/or mutations compared to the wildtype oncogene protein E1A, whereby the deletion is preferably one selected from the group comprising deletions of the CR3 region and deletions of the N-terminus and deletions of the C-terminus, including and particularly preferred those embodiments of the E1A protein as described in connection with dl520 or AdΔ24, dl922-947. E1Ad01/07, CB106 and/or the adenoviruses described in European patent EP 0 931 830, are embodiments of viruses, in particular adenoviruses, the replication of which is controlled by YB-1 through the activation of the E2-late promoter, preferably predominantly through the activation of the E2-late promoter. Further embodiments of the E1A protein which allow this form of replication of adenoviruses, can be generated by the ones skilled in the art based on the disclosure provided herein.

In further adenoviruses which are to be newly constructed, which are also referred to herein as derivatives and which may be used in accordance with the present invention, typically have an E1 deletion, an E1/E3 deletion and/or an E4 deletion, i. e. the corresponding adenoviruses are not able to generate functionally active E1 and/or E3 and/or E4 expression products and respective products, respectively, or, in other words, these adenoviruses are only capable to generate functional inactive E1, E3 and/or E4 expression products, hereby a functionally inactive E1, E3 and/or E4 expression product as such which is either not present as an expression product at all, whether at the transcription level and/or the translation level, or it is present in a form in which it at least is lacking one of the functions it has in wildtype adenoviruses. The function(s) of the expression product of the wildtype adenovirus is/are known to the ones skilled in the art and, for example, described in Russell, W. C., Journal of Virology, 81, 2573-2604, 2000. Russell (supra) describes also principles for the construction of adenoviruses and adenoviral vectors which are incorporated herein by reference. It is also within the present invention that the modified E1A oncoprotein. E1B55kDa, E4orf6 and/or E3ADP (adenoviral death protein (ADP)) (Tollefson, A. et al., J. Virology, 70, 2296-2306, 1996) is expressed in such a vector either individually or in any combination. In connection therewith, the individually named genes as well as the transgenes disclosed herein, can be cloned into the E1 and/or E3 and/or E4 region and be expressed independently by virtue of a suitable promoter or under the control of a suitable promoter. Basically, the regions E1, E3 and E4 are similarly suitable as cloning sites within the adenoviral nucleic acid. Suitable promoters are, among others, those as disclosed herein in connection with the control and expression, respectively, of E1A, in particular of the modified E1A.

Finally, in one embodiment the adenoviruses which are to be used in accordance with the present invention, are deficient with regard to E1B, in particular with regard to E1B 19 kDa. As used herein, the term deficient generally means a condition in which E1B does not have all of the characteristics inherent to the wildtype but at least one of these characteristics is absent.

The adenoviruses which are used in accordance with the invention disclosed herein, are, basically, known in the prior art in some embodiments. The adenoviruses used in accordance with the present invention are preferably recombinant adenoviruses, particularly also when a change, compared to the wildtype, has been made in accordance with the technical teaching provided herein. It is within the skills of those of the art to delete or mutate those adenoviral nucleic acid sequences which are not essential for the present invention. Such deletions may, for example, be related to a part of the nucleic acid coding for E3 and E4 as also described herein. A deletion of E4 is particularly preferred if such deletion does not extend to the protein E4orf6, or, in other words, the adenovirus to be used in accordance with the present invention codes for E4orf6. In preferred embodiments these adenoviral nucleic acids may still be packed into the viral capsid and may thus form infectious particles. The same is true for the use of the nucleic acids in accordance with the present invention. It should be noted that in general the adenoviral systems may be deficient with regard to single or several expression products. In connection therewith it is to be taken into consideration that this may be either based on the fact that the nucleic acid coding for such expression product is completely mutated or deleted or mutated or deleted to the extent that essentially no expression product is produced anymore or based on the lack of promoters or transcription factors which control the expression, or which are active in a manner different from wildtype, either at the nucleic acid level (lack of a promoter; cis-acting element) or at the translation system and the transcription system, respectively (trans-acting elements). Particularly the latter aspect may be dependent on the cellular background.

Apart from using adenoviruses in accordance with the present invention, which are already known, also novel adenoviruses can be used to the same extent as has already been disclosed for the other adenoviruses described herein. The novel adenoviruses according to the invention result from the technical teaching provided herein. Particularly preferred representatives are, for example, the viruses Xvir03 and Xvir03/01 depicted in FIG. 16 and FIG. 17, the design principle of which is also further illustrated in examples 11 and 12.

In the case of vector Xvir03 a CMV promoter is cloned into the E1 region which codes the nucleic acids for E1B55kDa and E4orf6, which are separated by a IRES sequence. Due to the introduction of these two genes and the gene products produced therefrom, respectively, a replication efficiency is created which factually corresponds to the one of wildtype viruses, whereby the selectivity of the replication is maintained for cells, particularly tumor cells, insofar as a replication happens in particular in YB-1 nucleus-positive cells and more particularly in cells in which YB-1 is deregulated. Cells in which YB-1 is deregulated, are preferably those which show an increased expression of YB-1, preferably compartment-independent, compared to normal or non-tumor cells.

A further development of virus Xvir03 is virus Xvir03/01 into which, in a preferred embodiment, therapeutic genes or transgenes are cloned under the control of a specific promoter, in particular a tumor-specific or tissue-specific promoter. It is also within the scope of such a virus that also the E4 region is functionally inactive, preferably is deleted. The transgenes described herein may also be cloned into the E4 region, whereby this may occur in addition or alternative to the cloning of a transgene into the E3 region.

Such therapeutic genes may be prodrug genes, genes for cytokines, apoptosis-inducing genes, tumor suppressor genes, genes for metalloproteinase inhibitors and/or angiogenesis inhibitors. Additionally, siRNA, aptamers, antisense and ribozymes may be expressed which are directed against cancer-relevant target molecules. Preferably, the single or the multiple target molecules is/are selected from the group comprising resistance relevant factors, anti-apoptosis factors, oncogenes, angiogenesis factors. DNA synthesis enzymes, DNA repair enzymes, growth factors and their receptors, transcription factors, metalloproteinases, in particular matrix metalloproteinases and plasminogen activator of the urokinase type. Preferred embodiments thereof have already been disclosed herein.

Possible prodrug genes, which may be used in preferred embodiments, are, for example, cytosine deaminase, thymidine kinase, carboxypeptidase, uracil phosphoribosyl transferase; purine nucleoside phosphorylase (PNP); Kim et al. Trends in Molecular Medicine. Volume 8, No. 4 (Suppl), 2002, Wybranietz W. A. et al., Gene Therapy, 8, 1.654-1664, 2001; Niculescu-Duvaz et al., Curr Opin. Mol. Therapy, 1, 480.486, 1999; Koyama et al., Cancer Gene Therapy, 7, 1015-1022, 2000; Rogers et al., Human Gene Therapy, 7, 2235-2245, 1996; Lockett et al., Clinical Cancer Res, 3, 2075-2080, 1997; Vijayakrishna et al., J. Pharmacol. And Exp. Therapeutics, 304, 1280-1284, 2003.

Possible cytokines which may be used in preferred embodiments, are, for example. GM1-CSF, TNF-alpha, Il-12, Il-2, Il-6, CSF, interferon-gamma; Gene Therapy, Advances in Pharmacology, Volume 40, Editor: J. Thomas August, Academic Press. Zhang und Degroot, Endocrinology, 144, 1393-1398, 2003; Descamps et al., J. Mol. Med., 74, 183-189, 1996, Majumdar et al., Cancer Gene Therapy, 7, 1086-1099, 2000.

Possible apoptosis inducing genes as may be used in preferred embodiments, are, for example, decorin: Tralhao et al., FASEB 3, 17, 464-466, 2003, retinoblastoma 94: Zhang et al., Cancer Res., 63, 760-765, 2003, Bax and Bad; Zhang et al., Hum Gene Ther, 20, 2051-2064, 2002; apoptin: Noteborn and Pietersen, Adv. Exp. Med. Biol., 465, 153-161, 2000); ADP: Toth et al., Cancer Gene Therapy, 10, 193-200, 2003; bcl-xs: Sumantran et al., Cancer Res, 55, 2507-2512, 1995; E4orf4; Braithwaite and Russell, Apoptosis, 6, 359-370, 2001; FasL, Apo-I and Trail: Boehringer Manheim, Guide to Apoptotic Pathways, Arai et al., PNAC, 94, 13862-13867, 1997; Bims; Yamaguchi et al., Gene Therapy, 10, 375-385, 2003; GNR163: Oncology News, 17 Jun. 2000.

Possible tumor suppressor genes as may be used in preferred embodiments, are, for example, E1A, p53, p16, p27, p27, MDA-7, Opalka et al., Cell Tissues Organs, 172, 126-132, 2002, Ji et al., Cancer Res., 59, 3333-3339, 1999, Su et al., Oncogene, 22, 1164-1180, 2003.

Possible angiogenesis inhibitors as may be used in preferred embodiments are, for example, endostatin, angiostatin: Hajitou et al., FASEB J., 16, 1802-1804, 2002, and antibodies against VEGF (Ferrara, N., Semin Oncol 2002 December; 29 (6 Suppl 16): 10-4.

Possible metalloproteinase inhibitors as may be used in preferred embodiments are, for example, Timp-3, Ahonen et al., Mol Therapy, 5, 705-715, 2002; PAI-I; Soff et al., J. Clin. Invest., 96, 2593-2600, 1995; Timp-1, Brandt K. Curr. Gene Therapy, 2, 255-271, 2002.

siRNA (short interfering RNA) consists of two, preferably two separate RNA strands, which hybridise with each other due to base complementarity, i. e. are essentially base paired and preferably have a length of up to 50 nucleotides, preferably between 18 and 30 nucleotides, more preferably less than 25 nucleotides and most preferably 21, 22 or 23 nucleotides, whereby these figures refer to the single strand of the siRNA, in particular to the length of the stretch of the single strand which hybridises with one, and more particularly with the second single strand and is base paired therewith, respectively. siRNA specifically induces or mediates the degradation of mRNA. The specificity required thereto for is provided by the sequence of the siRNA and thus its binding site. The target sequence to be degraded is essentially complementary to the first or to the second one of the siRNA forming strands. Although the exact mode of action is still unclear, it is assumed that siRNA represents a biological strategy for cells to inhibit certain alleles during development and to protect itself from viruses. siRNA mediated RNA interference is used for the specific suppression or even complete knock-out of the expression of a protein by introducing a gene specific double-stranded RNA. For higher organisms an siRNA having a length from 19 to 23 nucleotides, is thus particularly preferred as it does not result in activation of an in specific defense reaction, the so-called interleukin response. Immediate transfection of double-stranded RNA consisting of 21 nucleotides having symmetric 2-nt long overhangs at the 3' end was able to mediate RNA interference in mammal cells and was highly efficient compared to other technologies such as ribozymes and antisense molecules (Elbashir, S. Harborth I. Lendeckel W. Yalvcin, A. Weber K Tuschl T: Duplexes of 21-nucleotide RNAs mediate RNA interference in cultured mammalian cells. Nature 2001, 411: 494-498). Only very few siRNA molecules were necessary so as to inhibit the expression of the target gene. In order to avoid the limitations of exogenously administered siRNA which particularly resides in the transient nature of the interference phenomenon and the specific delivery of the siRNA molecules, the prior art uses vectors which allow for an endogenous siRNA expression. For example, oligonucleotides having a length of 64 nucleotides are provided which contain the 19 nucleotide long target sequence, both in sense as well as in antisense orientation, separated through a, for example, 9 nucleotide long spacer sequence which was introduced into the vector. The resulting transcript folded into a hairpin structure having a stem structure of, for example, 19 base pairs. The loop is rapidly degraded in the cell so that a functional siRNA is generated (Brummelkamp et al., Science, 296, 550-553, 2002).

The activity of pRb and E2F. respectively, is regulated through phosphorylation. The hypophosphorylated form of pRb is predominantly present in the G1 and M phase. In contrast, the hyperphosphorylated form of pRb is present in the S and G2 phase. E2F is released from the complex consisting of E2F and hypophosphorylated pRb by phosphorylation of pRb. The release of E2F from the complex consisting of E2F and hypophosphorylated pRb results in the transcription of E2F dependent genes. The E1A protein does not only bind to the hypophosphonlated form of pRb, whereby the binding of E1A to pRb happens mostly through the CR2 region of the E1A protein. Additionally, it also binds to the CR1 region, although with lower affinity (Ben-Israel and Kleiberger, Frontiers in Bioscience, 7, 1369-1395, 2002; Helt and Galloway, Carcinogenesis, 24, 159-169, 2003).

The nucleic acid coding for YB-1 which, in an embodiment of the adenoviruses to be used in accordance with the present invention, is part of the adenoviruses, may also comprise a nucleic acid sequence mediating the transport of YB-1 into the nucleus. The nucleic acids, adenoviruses and adenoviral systems in accordance with the invention as well as the adenoviruses known in the prior art such as, for example, Onyx-015, AdΔ24, d1922-947. E1Ad01/07, CB016, d1 520 and the adenoviruses described in patent EP 0 931 830, can be used as such or in combination with these nucleic acids in accordance with the invention in connection therewith as adenoviruses and adenoviral systems and thus as the corresponding nucleic acids. Suitable nucleic acid sequences which mediate nucleus transport, are known to the ones skilled in the art and, for example, described in (Whittaker. G. R. et al., Virology, 246, 1-23, 1998; Friedberg, E. C., TIBS 17, 347, 1992; Sans, D. A. et al., Bioessays 2000 June; 22(6): 532-44; Yoneda, Y., J. Biochem. (Tokyo) 1997 May; 121(5)-811-7; Boulikas, T., Cnt. Rev. Eukaryot. Gene Expr. 1993; 3(3): 193-227; Lyons R H, Mol. Cell Biol., 7, 2451-2456, 1987). In connection with the nucleus transport mediating nucleic acid sequences, different principles can be used. One such principle may, for example, be that YB-1 is formed as a fusion protein together with a signal peptide and is introduced into the nucleus and that the replication of the adenoviruses according to the present invention thus occurs.

A further principle which may be realised in the design of the adenoviruses used in accordance with the invention, is that YB-1 can be provided with a transporter sequence which, preferably starting from synthesis in the cytoplasma, introduces YB-1 into the cell nucleus or which translocates YB-1 into the cell nucleus, and promotes viral replication there. An example for a particularly effective nucleic acid sequence mediating nucleus transport is the TAT sequence of HIV which is, among other suitable nucleic acid sequences of that type described in Efthymiadis, A., Briggs, L J, Jans, D A., JBC 273, 1623-1628, 1998. It is within the present invention that the adenoviruses which are used in accordance with the present invention, comprise nucleic acid sequences which code for peptides coding for nuclear transportation.

It is within the present invention that YB-1 is present in its full length, particularly in a form which corresponds to the wildtype of YB-1. It is within the present invention that YB-1 is used or present as a derivative, such as, e. g. in shortened or truncated form. A YB-1 derivative as used or present within the present invention, is a YB-1 which is capable of binding to the E2-late promoter and thus activates gene expression of the adenoviral E2 region. Such derivatives particularly comprise the YB-1 derivatives disclosed herein. Further derivatives may be generated by deletion of single or several amino acids at the N-terminus, at the C-terminus or within the amino acid sequence.

With regard to the previously mentioned various further expressed genes and gene products coded by the adenoviruses, it is also possible that these are coded in any combination and expressed in any combination, respectively.

The terms adenovirus and adenoviral system shall have essentially the same meaning within the present invention. Adenovirus shall particularly refer to the complete viral particle comprising the capsid and the nucleic acid. The term adenoviral system particularly focuses on the fact that the nucleic acid shall be changed compared to the wildtype. Preferably such changes comprise changes in the structure of the genome of the adenovirus as may arise from deleting and/or adding and/or mutating promoters, regulatory sequences and/or coding sequences such as open reading frames. Additionally, the term adenoviral system is preferably used in connection with a vector, which is, for example, used in gene therapy.

The previously provided comments, including any use as well as design of the adenoviruses and adenoviral systems, respectively, apply also to the coding nucleic acids and vice versa.

In connection with the present invention it is possible that the adenoviruses to be used in accordance with the present invention and the nucleic acids coding therefor, respectively, may be any respective adenoviral nucleic acid which results in a replication event as such or in combination with further nucleic acid sequences. It is possible, as explained herein, that by means of helper virus the sequences and/or gene products required for replication are provided. To the extent it is referred to coding nucleic acid sequences and to the extent that such nucleic acid sequences are known, it is within the invention that not only the identical sequences used but also sequences derived therefrom. The term derived sequences shall in particular refer herein to sequences which still result in a gene product, either a nucleic acid or a polypeptide, that exhibits a function which corresponds to one or the function of a non-derived sequence. This can be determined by simple routine tests known to the one skilled in the art. An example for such derived nucleic acid sequences are those nucleic acid sequences which code for the same gene product, in particular for the same amino acid sequence, however, have a deviating sequence of bases due to the degeneracy of the genetic code.

In a preferred embodiment, with regard to the adenoviruses according to the present invention and the adenoviral replication system according to the present invention and the use of them according to the present invention, respectively, the adenoviral nucleic acid is deficient for the expression of the oncogene protein, particularly of the E1A protein, which means that it is either not coding for the 12S E1A protein or for the 13S E1A protein, or it is neither coding for the 12S E1A protein nor the 13S E1A protein, or is modified, as defined herein, and that the adenoviral replication system further comprises a nucleic acid of a helper virus, whereby the nucleic acid of the helper virus comprises a nucleic acid sequence which codes for the oncogene protein, in particular for the E1A protein, which has the following characteristics and imparts the following characteristics to the adenovirus, respectively, namely that it preferably is not replicating in YB-1 nucleus-negative cells but in cells which are independent from the cell cycle YB-1 nucleus-positive, transactivating at least one viral gene, in particular E1B55kDa, E4orf6, E4orf3 and/or E3ADP, in YB-1 nucleus-positive cells, and/or does not translocate cellular YB-1 into the nucleus. It is within the present invention that the transgenes described herein are coded individually or together by the helper virus and/or expressed therefrom.

In an embodiment of such an adenoviral replication system according to the present invention the adenoviral nucleic acid and/or the nucleic acid of the helper virus are furthermore present as vectors which are capable of replicating.

It is within the present invention that the coding nucleic acid(s) coding for the adenoviruses which are used according to the present invention, is/are present in a vector, preferably in an expression vector and this expression vector is used in accordance with the present invention.

In a further aspect the present invention is also related to a vector group comprising at least two vectors, whereby the vector group comprises altogether an adenoviral replication system as described herein, and the vector group is used in accordance with the present invention. It is intended that each of the components of the adenoviral replication system is arranged on an individual vector, preferably an expression vector.

Finally, the present invention is related in a further aspect to the use of a cell for the same purposes as described herein for the adenoviruses, whereby the cell comprises one or several nucleic acids which code for the adenoviruses described herein to be used in accordance with the invention and/or a respective adenoviral replication system and/or a respective vector and/or a vector group according to the present invention.

The previously described constructs of adenoviruses and in particular their nucleic acids and the nucleic acids coding therefor, may also be introduced into a cell in parts, particularly into a tumor cell, whereupon due to the presence of the various individual components they may act together such as if the individual components originated from a single nucleic acid and a single or several adenoviruses, respectively.

The nucleic acids coding for adenoviruses, adenoviral systems or parts thereof, which are used in accordance with the invention, may be present as vectors. Preferably, they are present as viral vectors. In case of nucleic acids comprising adenoviral nucleic acids the virus particle is preferably the vector. However, it is also within the invention that said nucleic acids are present in a plasmid vector. In any case the vector comprises elements which provide for the propagation of the inserted nucleic acid, i. e. replication and optionally expression of the inserted nucleic acid, and control of them, respectively. Suitable vectors, in particular expression vectors, and corresponding elements are known to the ones skilled in the art and, for example, described in Grunhaus. A., Honvitz. M. S., 1994, Adenoviruses as cloning vectors. In Rice, C., edit., Seminars in Virology, London: Saunders Scientific Publications.

The aspect of the invention that is related to the vector group, accounts for the previously described embodiment, that the various elements of the nucleic acid are not necessarily contained on one vector only. Accordingly, a vector group comprises at least two vectors. Otherwise, what has been said in relation to the vectors is also applicable to the vectors and the vector group, respectively.

The adenoviruses which are used in accordance with the invention are characterised by various nucleic acids and gene products, respectively, disclosed herein, and may otherwise comprise all those elements known to the one skilled in the art, as is also the case for adenoviruses of the wildtype (Shenk, T.: Adenoviridae: The virus and their replication. Fields Virology, $3^{rd}$ edition, edit. Fields, B. N., Knipe, D. M., Howley, P. M. et al., Lippincott-Raven Publishers, Philadelphia, 1996, chapter 67).

The replication of adenoviruses is a very complex procedure and usually makes use of the human transcription factor E2F. During viral infection, first, the "early genes" E1, E2. E3 and E4 are expressed. The group of the "late genes" is responsible for the synthesis of the viral structural proteins. For the activation of both the early as well as the late genes, the E1 region consisting of the two transcriptional units E1A and E1B, which code for different E1A and E1B proteins, are critical as the transcription of the E2, E3 and E4 is induced by them (Nevins, J. R., Cell 26, 213-220, 1981). Additionally, the E1A proteins can induce DNA synthesis in resting cells and thus initiate the entry into the S phase (c. f. Boulanger and Blair, 1991). Additionally, they interact with the tumor suppressors of the Rb class (Whyte, P. et al., Nature 334, 124-127, 1988). In doing so, the cellular transcription factor E2F is released. The E2F factors may subsequently bind to corresponding promoter regions of both cellular as well as viral genes (in particular to the adenoviral E2 early promoter) and thus initiate transcription and replication (Nevins, I. R., Science 258, 424-429, 1992).

The gene products of the E2 region are especially needed for the initiation and performance, respectively, of the replication, as they code for three essential proteins. The transcription of the E2 proteins is controlled by two promoters, the "E2-early E2F-dependent" promoter which is also referred to herein as E2-early promoter or early E2 promoter, and the "E2-late" promoter (Swaminathan and Thimmapaya, The Molecular Repertoire of Adenoviruses III: Current Topics in Microbiology and Immunology, Vol 199, 177-194, Springer Verlag 1995). Additionally, the products of the E4 region together with the E1A and E1B55kDa-protein play an important role for the activity of E2F and the stability of p53, respectively. For example, the promoter is even more activated by a direct interaction of the E4orf6/7 protein coded by the E4 region, with the heterodimer consisting of E2F and DP 1 (Swaminathan and Thimmapaya, JBC 258, 736-746, 1996). Furthermore, p53 is inactivated by the complex consisting of E1B55kDa and E4orf6 (Steegenga, W. T. et al., Oncogene 16, 349-357, 1998), in order to successfully complete a lytic infectious cycle. Additionally, the E1B55kDa protein exhibits a further important function insofar as it promotes by interacting with the E4orf6 protein the export of viral RNA from the nucleus, whereas the proprietary RNAs of the cell are retained in the nucleus (Bridge and Ketner, Virology 174, 345-353, 1990). A further important discovery is that the protein complex consisting of E1B55kDa/E4orf6 is localised in the so-called "viral inclusion bodies". It is assumed that these structures are the sites of replication and transcription (Omelles and Shenk, J. Virology 65, 424-429, 1991).

A further region which is important for replication and in particular for the release of adenoviruses, is the E3 region. The E3 region comprises more particularly the genetic information for a variety of comparatively small proteins which are not essential for the adenoviral infectious cycle in vitro, i. e. are not essential in cell culture. However, they play an important role for the survival of the virus during an acute and/or latent infection in vivo, as they have, among others, immune regulatory and apoptotic function(s) (Marshall S. Horwitz, Virolgie, 279, 1-8, 2001; Russell. supra). It could be shown that a protein having a size of about 11.6 kDa induces cell death. The protein was, due to its function, referred to as ADP—for the english term adenovirus death protein—(Tollefson. J. Virology, 70, 2296-2306, 1996). The protein is predominantly formed in the late phase of the infectious cycle. Furthermore, overexpression of the protein results in a better lysis of the infected cells (Doronin et al., J. Virology, 74, 6147-6155, 2000).

Furthermore, it is known to the present inventor that E1A deleted viruses, i. e. in particular viruses which do not have a 12S E1A protein and which also do not express a 13S E1A protein, can very efficiently replicate at higher MOIs (Nevins J. R., Cell 26, 213-220, 1981), which, however, cannot be realised in any clinic application. This phenomenon is referred to as "E1A-like activity" in literature. It is was also known that from the 5 proteins coded by E1A, two proteins, namely the 12S and 13S protein, control and induce, respectively, expression of the other adenoviral genes (Nevins. J. R., Cell 26, 213-220, 1981; Boulanger, P. and Blair. E.; Biochem. J. 275, 281-299, 1991). In connection therewith it was shown that the transactivating function is predominantly provided by the CR3 region of the 13S protein (Wong H K und Ziff E B., J Virol., 68, 4910-20, 1994). Adenoviruses which have specific deletions in the CR1 and/or CR2 region and/or CR3 region of the 13S protein, are mostly replication-deficient, however, are still transactivating in some cell lines the viral genes and promoters, respectively, in particular the E2 region (Wong H K, Ziff E B., J Virol. 68, 4910-20, 1994; Mymryk, J. S. and Bayley, S. T., Virus Research 33, 89-97, 1994).

After infection of a cell, typically a tumor cell, using a wildtype adenovirus, YB-1 is induced into the nucleus which is mediated by E1A, E1B55kDa and E4orf6, and is co-localised with E1B55kDa in the nucleus in the viral inclusion bodies, which allows for an efficient replication of the virus in the cell nucleus both in vitro and in vivo. In connection therewith, it has already been found earlier that E4orf6 binds to E1B55kDa (Weigel, S. and Dobbelstein, M. J. Virology, 74, 764-772, 2000; Keith N. Leppard, Seminars in Virology, 8, 301-307, 1998) and thus mediates the transport and distribution, respectively, of E1B55kDa into the nucleus, which provides for an optimum virus production and adenoviral replication, respectively. An efficient replication of the virus in accordance with the present invention is possible due to the interaction of E1A, E1B55kDa and YB-1, and by the complex consisting of E1B55kDa/E4orf6 with YB-1, respectively, and the co-localisation of YB-1 and E1B55kDa in the nucleus in the so-called viral inclusion bodies and thus the use of the viruses described herein for replication in cells which are YB-1 nucleus-positive and for the manufacture of a medicament for the treatment of diseases, whereby YB-1 nucleus-positive cells are involved. The replication being thus possible with this cellular background, results in lysis of the cell, release of the virus and infection and lysis of adjacent cells, so that in case of an infection of a tumor cell and a tumor, respectively, finally lysis of the tumor, i. e. oncolysis, occurs.

YB-1 belongs to the group of highly conserved factors which bind to an inverted CAAT sequence, the so-called Y-box. They may be active in a regulatory manner both at the level of transcription as well as translation (Wolfe, A. P. *Trends in Cell Biology* 8, 318-323, 1998). A growing number of Y-box dependant regulatory pathways is found in the activation but also in the inhibition of growth and apoptosis associated genes (Swamynathan, S. K. et al., FASEB J. 12, 515-522, 1998). Accordingly, YB-1 directly interacts with p53 (Okanoto, T. et al., Oncogene 19, 6194-6202, 2000), plays an important role in the gene expression of Fas (Lasham, A. et al., Gene 252, 1-13, 2000), MDR and MRP gene expression (Stein, U. et al., JBC 276, 28562-69, 2001, Bargou, R. C. et al., Nature Medicine 3, 447-450, 1997) and in the activation of topoisomerases and metalloproteinases (Mertens, P. R. et al., JBC 272, 22905-22912, 1997; Shibao, K. et al., Int. J. Cancer 83, 732-737, 1999). Additionally, YB-1 is involved in the regulation of mRNA stability (Chen, C-Y. et al., Genes & Development 14, 1236-1248, 2000) and repair processes (Ohga, T. et al., Cancer Res 56, 4224-4228, 1996).

The nuclear localisation of YB-1 in tumor cells results in E1A independent viral replication whereby in particular neither a 12S E1A protein nor a 13S E1A protein is present in an expressed form and used, respectively (Holm, P. S. et al. JBC 277, 10427-10434, 2002) and in case of overexpression of the protein YB-1 in multidrug resistance (multiple resistance). Additionally it is known that the adenoviral proteins such as e. g. E4orf6 and E1B55kDa have a positive effect on viral replication (Goodrum, F. D. and Omelles, D. A, J. Virology 73, 7474-7488, 1999), whereby a functional E1A protein is responsible for switching on the other viral gene products (such as E4orf6, E3ADP and E1B55kDa) (Nevins J. R., Cell 26, 213-220, 1981). This, however, does not occur with the E1A-minus adenoviruses of the prior art in which the 13S E1A protein is not present. The nuclear localisation of YB-1 in multidrug resistant cells which have YB-1 in the nucleus, provides for replication and particle formation, respectively, of such E1A-minus viruses. In this case, however, the efficiency of viral replication and particle formation is reduced by several multiples compared to wildtype Ad5. A combination of YB-1 which is either already present in the nucleus of the tumor cell, or is induced into the tumor cell by external factors (e. g. application of cytostatics or irradiation or hyperthermia), i. e. is prompted to be present in the nucleus, particularly independent from the cell cycle, or is introduced as a transgene through a vector, with a system, preferably with an adenoviral system, which switches on adenoviral genes, but which does not allow for viral replication, has been surprisingly found to be a system which mediates a very efficient viral replication and particle formation through YB-1 and thus provides oncolysis. Suitable cytostatics are, among others, those which belong to the following groups: anthracyclines, such as daunomycin and adriamycin; alkylating agents, such as cyclophosphamide; alkaloids, such as etoposide; vin-alkaloids, such as vincristine and vinblastine; antimetabolites such as for example 5-fluorouracil and methrotrexate; platin derivatives, such as for example cis-platin; topoisomerase inhibitors, such as camphothecine; and taxanes, such as for example taxole. The adenoviruses disclosed herein, in particular the recombinant adenoviruses, which are only capable of replicating in YB-1 nucleus-positive cells, are limited in their capability to transactivate the viral genes E1B55kDa, E4orf6, E4orf3 and E3ADP, compared to the corresponding transactivating capabilities of wildtype adenoviruses, in particular wildtype Ad5. The present inventor has now surprisingly found that these limited transactivating capabilities may be compensated by the corresponding genes and in particular by E1B55kDa and E4orf6 being expressed in combination with the nuclear localisation of YB-1. As shown in the examples herein, viral replication and particle formation, respectively, is increased under such conditions to a level which is comparable to the replication and particle formation behaviour of wildtype adenoviruses.

It is intended that the medicament in connection with which or for the manufacture of which the adenoviruses described herein are used in accordance with the present invention, is usually applied systematically, although it is also within the present invention to apply or deliver such medicament locally. The application is done with the intention that particularly those cells are infected with the adenovirus and that particularly in these cells replication occurs, which are involved, preferably in a causal manner, in the formation of a condition, typically a disease, for the diagnosis and/or prevention and/or treatment of which the medicament according to the present invention is used.

Such a medicament is preferably for the treatment of tumor diseases. Among the tumor diseases, those are particularly preferred in which either YB-1 is already located in the nucleus due to the mechanism underlying the tumor disease, in particular the underlying pathological mechanism, or those where the presence of YB-1 in the nucleus is caused by exogenous measures, whereby the measures are suitable to transfer YB-1 into the nucleus, induce YB-1 there or to express YB-1 there. The term tumor or tumor disease as used herein shall comprise both malignant as well as benign tumors and respective diseases. It can be intended that the medicament comprises at least one further pharmaceutically active compound. The kind and the amount of such further pharmaceutically active compound will depend on the indication for which the medicament is to be used. In case the medicament is used for the treatment and/or prevention of tumor diseases, typically cytostatics, such as for example cis-platin and taxol, daunoblastin, daunorubicin, adriamycin and/or mitoxantron or others of the cytostatics or groups of cytostatics which are described herein, are used.

The medicament according to the present invention can be present in various formulations, preferably in a liquid form. Furthermore, the medicament will contain stabilisers, buffers, preservatives and such agents which are known to the one skilled in the art of pharmaceutical formulations.

The present inventor has surprisingly found that the use in accordance with the invention of the viruses described herein can be applied with a very high success rate to tumors which have YB-1 in the nucleus independent from the cell cycle. Normally. YB-1 is located in the cytoplasm, in particular also in the perinuclear plasma. During S-phase of the cell cycle. YB-1 can be found in the cell nucleus of both normal cells as well as tumor cells. This, however, is not sufficient to provide for viral oncolysis using thus modified adenoviruses. The comparatively little efficacy of such attenuated adenoviruses described in the prior art is ultimately based on their wrong application. In other words, such adenoviral systems can be used, particularly also with an increased efficacy, where the molecular biological prerequisites for viral oncolysis are given when the attenuated or modified viruses as described herein, are administered. In case of the described adenoviruses which are to be used in accordance with the invention as described herein, such as AdΔ24, d1922-947. E1Ad101/07, CB016, d1520 and the recombinant adenoviruses described in European patent EP 0 931 830, the prerequisites are given in case of tumor diseases the cells of which show a nuclear localisation of YB-1 independent of the cell cycle. This form of nuclear localisation may be either caused by the kind of tumor itself or may be caused by the measures or agents in accordance with the invention which are described herein. The present invention thus defines a new group of tumors and tumor diseases, respectively, and thus also of patients, which can still be treated successfully with the viruses in accordance with the invention, particularly also with the attenuated or modified adenoviruses already described in the prior art.

A further group of patients which can be treated in accordance with the present invention using the adenoviruses, some of which are known and which can be used in accordance with the present invention, or using the adenoviruses which are described herein for the first time, in particular using such adenoviruses which have mutations and deletions, respectively, in the E1A protein which do not interfere with the binding of Rb/E2f, but which do not replicate in YB-1 nucleus-negative cells or which have and show, respectively, a strongly reduced replication as defined herein, and/or a deleted oncoprotein, particularly E1A, such as, for example, the viruses AdΔ24, d1922-947, E1Ad101/07, CB106 and the adenoviruses described in European patent EP 0 931 830, are those patients for which it is ensured that by applying or realising distinct conditions YB-1 is migrating into the nucleus or is induced there or is transported therein. The use of such adenoviruses in connection with this group of patients is based on the finding that the induction of viral replication is based on the nuclear localisation of YB-1 with subsequent binding of YB-1 to the E2-late promoter. Due to the findings disclosed herein adenoviruses such as AdΔ24, d1922-947. E1Ad/01/07, CB106 and/or the adenoviruses described in European patent EP 0 931 830 may also replicate in cells which are YB-1 nucleus-positive and/or in cells in which YB-1 is deregulated as defined in the present invention. Insofar, these adenoviruses can, according to the present invention, be used for the treatment of diseases and groups of patients, respectively, which/who comprise cells having these characteristics, particularly when these cells are involved in the formation of the respective disease to be treated. This is the basis for the success of AdΔ24, d1922-947, E1Ad/01/07, CB016 and the adenoviruses described in patent EP 0 931 831) for the treatment of such tumors, in accordance with the present invention, which have YB-1 in the nucleus independent of the cell cycle or in which YB-1 is deregulated in the sense of the present disclosure. A further group of patients which can be treated in accordance with the invention using the adenoviruses which are described herein as being usable in accordance with the invention, and using those viruses, in particular adenoviruses, which are described herein for the first time, are those which are YB-1 nucleus-positive and/or which are YB-1 nucleus-positive as a result of the treatments described in the following, whereby such treatment is preferably a medical treatment, and/or those patients which have undergone such treatment concomitantly with the administration of respective viruses. It is within the present invention that YB-1 nucleus-positive patients are patients which have YB-1 in the nucleus independent from the cell cycle in a number of cells forming a tumor. Among these treatments is the administration of cytostatics as described herein altogether and/or as used in a tumor therapy. Additionally, radiation, preferably radiation as used in a tumor therapy, belongs to this group of treatments. Radiation means in particular radiation with high energy radiation, preferably radioactive radiation, preferably as used in tumor therapy. Hyperthermia and the application of hyperthermia, preferably hyperthermia as used in tumor therapy, are further treatments. In a particularly preferred embodiment hyperthermia is applied locally. Finally, hormone treatment, particularly hormone treatment as used in tumor therapy, is a further treatment. In connection with such hormone treatment anti-estrogens and/or anti-androgens are used Anti-estrogens such as tamoxifene, particularly in the therapy of breast cancer, and anti-androgens such as for example flutamide or cyproterone acetate, are used in the therapy of prostate cancer.

It is within the present invention that some of the cells forming the tumor comprise YB-1 either inherently or after induction and active introduction into the nucleus, respectively, or comprise deregulated YB-1 in the sense of the present disclosure. Preferably, about 5% or any percentage above, i. e. 6%, 7%, 8% etc. of the tumor forming cells are such YB-1 nucleus-positive cells or cells in which YB-1 is present in a deregulated manner. Nuclear localisation of YB-1 can be induced by stress applied from outside and by locally applied stress, respectively. This induction can, for example, occur by means of radiation, in particular UV radiation, application of cytostatics, as, among others, already disclosed herein, and hyperthermia. In connection with hyperthermia it is essential that it can be realised now in a very specific manner, more particularly in a locally very specific manner, and may thus also provide for a specific nuclear localisation of YB-1 in the cell nucleus and, because of this, provide the prerequisites for a replication of the adenovirus and thus for cell and tumor lysis, which is preferably locally limited (Stein U, Jurchott K, Walther W, Bergmann S, Schlag P M, Royer H D, J Biol Chem. 2001, 276(30):28562-9; Hu Z, Jin S, Scotto K W, J Biol Chem. 2000 Jan. 28; 275(4):2979-85; Ohga T. Uchiumi T, Makmo Y, Koike K, Wada M, Kuwano M, Kohno K. J Biol Chem. 1998, 273(10.5997-6000).

The medicament according to the present invention could thus also be administered to patients and groups of patients, or may be intended for them, where through appropriate pretreatment or concomitant treatment a transport of YB-1 is affected, preferably in the respective tumor cells.

Based on this technical teaching it is for the person of the art within his skills to perform suitable modifications particularly on E1A which, for example, may comprise deletions or point mutations in order to thus generate various embodiments of the adenoviruses, which may be used in connection with the use in accordance with the invention.

As has already been explained above, the adenoviruses which are used in accordance with the present invention, are capable of replicating in such cells and cellular systems, respectively, which have YB-1 in the nucleus. For answering the question whether the adenoviruses used in accordance with the present invention are able to replicate and are thus able to lyse the tumor, the status of the cells with regard to the presence or absence of Rb, i. e. the retinoblastome tumor suppressor product, is irrelevant. Additionally, it is in connection with the use in accordance with the invention of said adenoviruses, not essential to take into consideration the p53 status of the infected cells, the cells to be infected or the cells to be treated, as by using the adenoviral systems as disclosed herein in connection with YB-1 nucleus-positive cells, i. e. cells which have YB-1 in the nucleus irrespective of the cell cycle, this p53 status as well as the Rb status do not have an impact on the performance of the technical teaching disclosed herein.

The oncogene and oncogene protein, respectively, in particular E1A, can be either under the control of the proprietor natural adenoviral promoters and/or be controlled by means of a tumor or tissue specific promoter. Suitable non-adenoviral promoters can be selected from the group comprising cytomegalovirus promoter, RSV (Rous sarcoma virus) promoter, adenovirus-based promoter Va I and the non-viral YB-1 promoter (Makino Y. et al., Nucleic Acids Res. 1996, 15, 1873-1878). Further promoters which can be used in connection with each and any aspect of the invention disclosed herein, comprise the telomerase promoter, the alpha-fetoprotein (AFP) promoter, the caecinoembryonic antigen promoter (CEA) (Cao, G., Kuriyama, S., Gao, J., Mitoro, A., Cui, L., Nakatani, T., Zhang, X., Kikukawa, M., Pan. X., Fukui, H., Qi, Z. Int. J. Cancer, 78, 242-247, 1998), the L-plastin promoter (Chung, I., Schwartz, P E., Crystal, R C., Pizzorno, G, Leavitt, J., Deisseroth, A B. Cancer Gene Therapy, 6, 99-106, 1999), the arginine vasopressin promoter (Coulson, J M, Staley. J., Wall, P J. British J. Cancer, 80, 1935-1944, 1999), the E2f promoter (Tsukada et al. Cancer Res., 62, 3428-3477), the uroplakine II promoter (Zhang et al., Cancer Res., 62, 3743-3750, 2002) and the PSA promoter (Hallenbeck P L, Chang, Y N, Hay, C, Golightly, D., Stewart, D., Lin. J., Phipps, S., Chiang, Y L. Human Gene Therapy, 10, 1721-1733, 1999). Furthermore, the YB-1 dependent E2-late promoter of adenoviruses as described in German patent application DE 101 50 984.7, is a promoter which can be used in the present invention.

It is known that the telomerase promoter is of crucial importance in human cells. Accordingly, telomerase activity is regulated through transcriptional control of the telomerase reverse transcriptase gene (hTERT), which is the catalytic subunit of the enzyme. The expression of the telomerase is active in 85% of human tumor cells. In contrast thereto, it is not active in most of the normal cells. Exempt therefrom are germ cells and embryonic tissue (Braunstein, I. et al., Cancer Research, 61, 5529-5536, 2001. Majumdar, A. S. et al., Gene Therapy 8, 568-578, 2001). More detailed studies on the hTERT promoter have revealed that fragments of the promoters 283 bp and 82 bp, respectively, distant from the initiation codon are sufficient for specific expression in tumor cells (Braunstein I. et al.; Majumdar A S et al., supra). Therefore, this promoter and the specific fragments, respectively, are suitable to provide for a specific expression of a gene and particularly of a transgene, preferably one of the transgenes disclosed herein, in tumor cells only. The promoter shall allow the expression of the modified oncogene, preferably the E1A oncogene protein, in tumor cells only. Also, in a preferred embodiment, the expression of a transgene, particularly one which is selected from the group comprising E4orf6, E1B55kDa, ADP and YB-1, in such adenoviral vector is under the control of any of these promoters. It is also within the present invention that the open reading frame of the transactivating oncogene protein, in particular of the E1A protein, is in frame with one or several of the gene products of the adenoviral system. The open reading frame of the transactivating E1A protein, however, can also be independent therefrom.

It is intended that with regard to the characteristics of the cells for the lysis of which the adenoviruses described herein are used in accordance with the present invention, these are, in an embodiment, resistant, preferably have a multidrug or multiple resistance. Resistance as used herein, refers preferably to a resistance against the cytostatics described herein. This multidrug resistance preferably goes along with the expression, preferably an overexpression, of the membrane-bound transport protein P-glycoprotein which can be used as a marker for determining respective cells and can thus also be used for tumors and respective groups of patients having such multidrug resistance. The term resistance as used herein comprises both the P-glycoprotein mediated resistance which is also referred to as classical resistance, as well as atypical resistance which comprises resistance which is mediated through MRP, or other, non-P-glycoprotein mediated resistances. A further marker, which correlates with the expression of YB-1, is topoisomerase II alpha. Insofar, in a screening for determining whether a patient may be treated with an expectation of success using the adenoviruses in accordance with the present invention, expression of topoisomerase II alpha can be used instead of or in addition to the determination of YB-1 in the nucleus. A further marker which can basically be used in a manner similar as P-glycoprotein, is MRP. A further marker, at least to the extent that the colorectal carcinoma cells or patients with colorectal carcinoma are concerned, is PCNA (engl. proliferating cell nuclear antigen) (Hasan S. et al., Nature, 15, 387-391, 2001), as, for example, described by Shibao K. et al (Shibao K et al., Int. Cancer, 83, 732-737, 1999). Finally, the expression of MDR (multiple drug resistance) is a marker in the aforedescribed sense (Oda Y et al., Clin. Cancer Res., 4, 2273-2277, 1998), at least for breast cancer cells and osteosarcoma cells. A further possible marker, which can be used in accordance with the present invention, is p73 (Kamiya, M., Nakazatp, Y., J Neurooncology 59, 143-149 (2002); Stiewe et al., J. Biol. Chem., 278, 14230-14236, 2003).

It is thus a particular advantage of the present invention that also patients can be treated using the adenoviruses in accordance with the present invention, as described herein, which are otherwise deemed as being no longer treatable in the clinical sense and where a further treatment of the tumor disease according to the methods of the prior art is no longer possible with a reasonable expectation of success, in particular where the use of cytostatics is no longer reasonably possible and can no longer be successfully performed in the sense of influencing or reducing the tumor. The term tumor refers herein in general to each and any tumor or cancer disease which either contains YB-1 in the nucleus inherently or contains YB-1 in the nucleus, preferably independent from the cell cycle, as a consequence of realising exogenous measures as described herein.

Additionally, the viruses described herein can be used for the treatment of tumors in general. Preferably, these tumors are selected from the group comprising breast cancer, ovary carcinoma, prostate carcinoma, osteosarcoma, glioblastoma, melanoma, small cell lung carcinoma and colorectal carcinoma. Further tumors are those which are resistant as described herein, preferably those which are multiple resistant and particularly also those tumors of the above described group.

The invention is related in a further aspect to a method for the screening of patients which can be treated using one of the modified adenoviruses, i. e. an adenovirus as used in accordance with the present invention such as, for example, AdΔ24, d1922-947, E1Ad/01/07, CB016 or the viruses described in European patent EP 0 931 830), whereby such method comprises the following steps:

examining a sample of a tumor tissue and determining whether YB-1 is located in the nucleus independent from the cell cycle.

The presence of the afore-described markers can be detected instead of or in addition to YB-1.

In case that the tumor tissue or a part thereof comprise YB-1 in the nucleus, in particular independent from cell cycle, the adenoviruses disclosed therein, can be used in accordance with the practice of the present invention.

In an embodiment of the method according to the present invention the examination of the tumor tissue is done by using an agent which is selected from the group comprising antibodies against YB-1, aptamers against YB-1 and spiegelmers against YB-1 as well as anticalines against YB-1 Basically, the same means can be produced for the corresponding markers and used accordingly. The manufacture of antibodies, in particular monoclonal antibodies, is known to the ones skilled in the art. A further means for specific detection of YB-1 or the markers, are peptides which bind with a high affinity to the target structures, in the present case YB-1 or said markers. In the prior art methods are known such as phage-display in order to generate such peptides. Typically, a peptide library is taken as a starting point, whereby individual peptides have a length of from 8 to 20 amino acids and the size of the library is about $10^2$ to $10^{18}$, preferably $10^8$ to $10^{15}$ different peptides. A special form of target molecule binding polypeptides are the so-called anticalines which are, for example, described in German patent application DE 197 42 706.

A further means for specific binding of YB-1 or the corresponding markers disclosed herein and thus for the detection of cell cyclus independent localisation of YB-1 in the cellular nucleus, are the so-called aptamers, i.e. D-nucleic acids which are present either as RNA or DNA either as a single strand or a double strand and specifically bind to the target molecule. The generation of aptamers is, for example, described in European patent EP 0 533 838. A special form of aptamers are the so-called aptazymes, which, for example, are described by Piganeau, N. et al (2000), Angew. Chem. Int Ed., 39, no. 29, pages 4369-4373. These are special embodiments of aptamers insofar as they comprise apart from the aptamer part a ribozyme part and get catalytically active upon binding or release of the target molecule binding to the aptamer part and cleave a nucleic acid substrate which goes along with the generation of a signal.

A further form of aptamers are the so-called spiegelmers, i. e. target molecule binding nucleic acids which are made of L-nucleic acids. The method for the manufacture of such spiegelmers is, for example, described in WO 98/08856.

The sample of the tumor tissue can be obtained by puncture or through surgery. The assessment whether YB-1 is localised in the nucleus independent from the cell cycle, is frequently done by using microscopic techniques and/or immuno histoanalysis, preferably using the antibody or any of the other aforementioned means. Further means for detecting YB-1 in the nucleus and in particular for detecting that YB-1 is located there independent from the cell cycle, are known to the one skilled in the art. For example, the localisation of YB-1 can be easily detected in stained tissue sections when screening them. The frequency of the presence of YB-1 in the nucleus already indicates that the localisation is independent from the cell cycle. A further option for cell cycle independent detection of YB-1 in the nucleus resides in the staining against YB-1 and detection whether YB-1 is localised in the nucleus and determination of the phase of the cells. This as well as the detection of YB-1 may also be performed by using the aforementioned means directed against YB-1. The detection of the means is done by methods known to the one skilled in the art. By said agents specifically binding to YB-1 and not to any other structures within the sample to be analysed, particularly the cells, their localisation and because of their specific binding to YB-1 also the localisation of YB-1 can be detected and established by a suitable labelling of the means. Methods for the labelling of said means are known to the ones skilled in the art.

In the following, the present invention shall be further illustrated by reference to the figures and samples from which new features, embodiments and advantages may be taken.

FIG. 7 shows the structural design of the E1A protein of wildtype adenovirus, of adenovirus dl520 and adenovirus dl1119/1131.

FIG. 18A/B shows wells grown with 181RDB cells (FIG. 18A) and 272RDB cells (FIG. 18B) after crystal violet staining and infection with Ad312 (20 pfu/cell). Xvir03 (5 pfu/cell) and control (non-infected), whereby crystal violet staining was performed five days past infection.

EXAMPLE 1: TYPES OF E1A MODIFICATIONS AS MAY BE COMPRISED BY THE ADENOVIRUSES WHICH ARE USED IN ACCORDANCE WITH THE INVENTION

Figure 1:
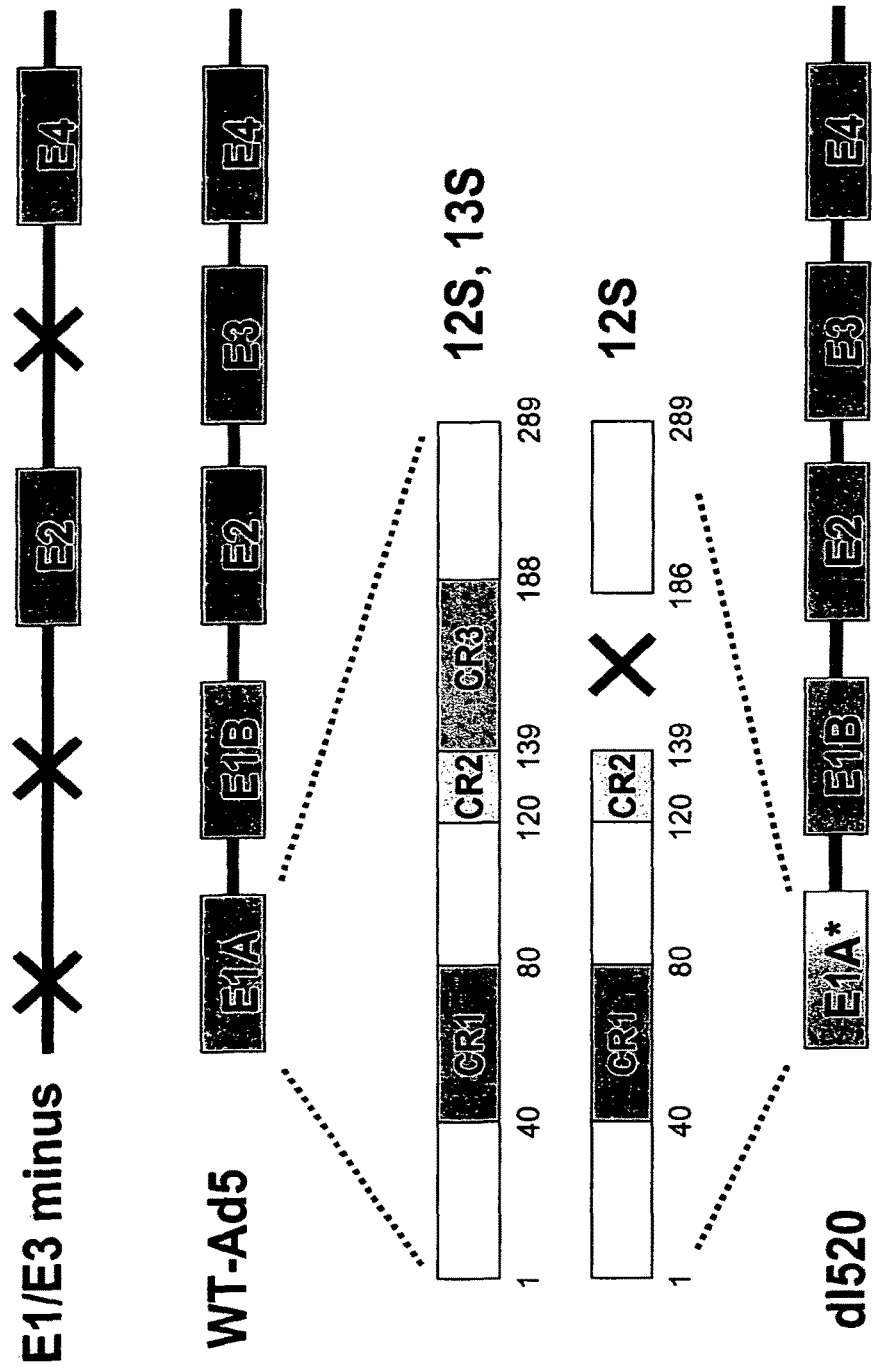
FIG. 1 shows the structural design of the adenoviral vectors referred to as AdE1/E3-minus herein which are E1/E3-deleted adenoviruses, of wildtype adenovirus and adenovirus dl520.

FIG. 1 shows the structural design of adenoviral vectors AdE1/E3-minus, i. e. E1/E3-deleted adenoviruses, wildtype adenovirus and adenovirus dl520.

Adenovirus AdE1/E3-minus does not have a region coding for a functional E1A or a functional E1B or E3 and is used in the present experiments as a control for toxicity.

Wildtype E1A gene codes for a total of 5 proteins which are generated through alternative splicing of the E1A RNA. Among others, two different proteins are generated, namely a 289 amino acid protein and a 243 amino acid protein, dl520 does not code for the 289 amino acid protein as it has a deletion in the CR3 stretch of the E1A gene which results in the lack of the 13S gene product. The adenovirus dl520 which may be used in accordance with the invention is referred to as 12S-E1A virus by those skilled in the art. Adenovirus dl347 (Wong and Ziff. J. Virol., 68, 4910-4920, 1994) known in the prior art is also a 12S-E1A virus which can be used in accordance with the present invention.

Within the 289 amino acid protein which is encoded by the 13S-E1A mRNA, there are 3 regions which are conserved among various adenoviral subtypes. These are referred to as CR1, CR2 and CR3. While CR1 and CR2 are present in both E1A proteins (E1A 12S and E1A 13S), i. e. in both the 289 amino acid and the 243 amino acid protein, the CR3 region is only present in the bigger one of the two aforementioned proteins.

The CR3 region is required for the activation of viral genes, in particular of E1B, E2, E3 and E4. Viruses which only comprise the smaller, i. e. 243 amino acid protein are only very weakly transactivating the viral genes and do not promote adenoviral replication in those cells which do not have YB-1 in the nucleus. As YB-1 is present in the nucleus only in tumor cells and can be detected only there, this vector is suitable to induce tumor-specific replication.

Due to the deletion of CR3 in dl520 this adenovirus cannot translocate cellular YB-1 into the cell's nucleus which is also referred to herein as translocation, and is thus not in a position to replicate in cells which are YB-1 nucleus-negative and is thus a virus which can be used in accordance with the present invention, whereby this virus comprises the transactivation required in accordance with the present invention.

EXAMPLE 2: MODE OF ACTION OF ADENOVIRUSES IN DEPENDING ON THE RB STATUS OF CELLS

Figure 2:
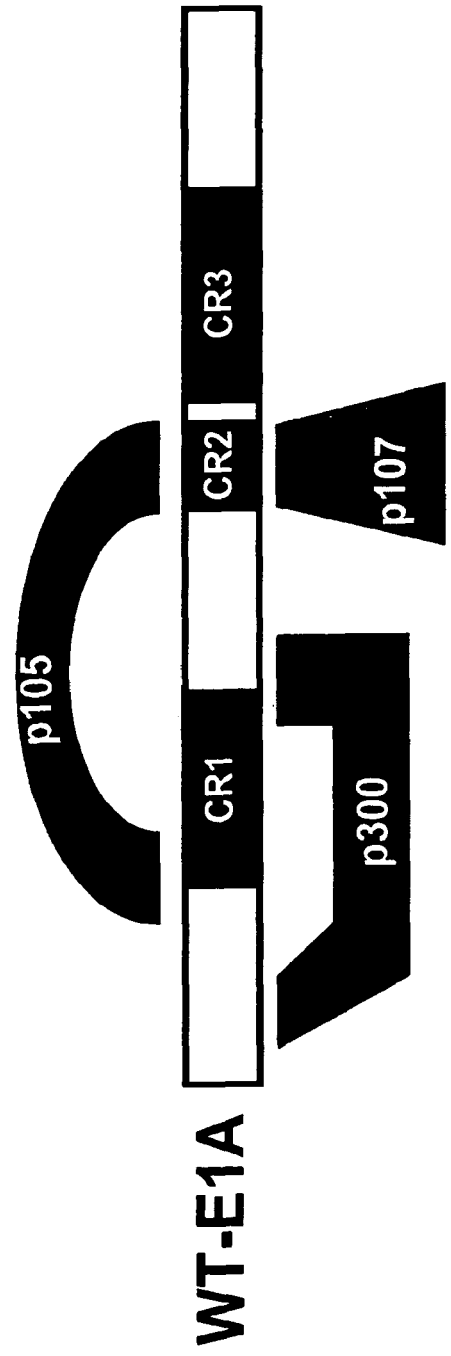
FIG. 2 shows the binding domains of the E1A protein with regard to the binding of p300, p107 and p105.

FIG. 2 shows the binding domains of the E1A protein with regard to the binding of p300, p107 and p105. P300, as well as p107, is a cellular binding protein. The binding of the retinoblastoma protein (pRb), a tumor suppressor protein, is mediated through CR1 and CR2. Studies have shown that pRb and p107/p300 are in combination with the cellular transcription factor E2F effective in regulating transcription. The wildtype E1A protein interferes with the binding of E2F to Rb. The thus released E2F binds to the E2 early promoter and induces adenoviral replication thereby.

It is known from the prior art that certain deletions in the E1A oncoprotein may result in recombinant adenoviral vectors such as those mentioned in the following, which are capable of replicating predominantly in Rb-negative cells and can be used in accordance with the present invention. For example, the adenoviral vector d1922-947 comprises a deletion in the CR2 region (amino acid positions 122-129) and the vector CB016 has deletions in the CR1 region (amino acid positions 27-80) and CR2 region (amino acid positions 122-129). The vector E1Ad/01/07 comprises a deletion in the CR2 region (amino acid positions 111-123). Additionally, because of an additional deletion at the N-terminus (amino acid positions 4-25), additionally, there is no binding to protein p300. The adenoviral vector AdΔ24 comprises a deletion in the CR2 region (amino acid positions 120-127). The adenoviral vector described in patent EP 0 931 830 comprises deletions in the CR1 region and CR2 region.

The binding mechanism of E2F/RB and the release of E2F mediated through E1A is fundamentally different from the mechanism underlying the present invention. Unlike assumed in the prior art it is not the release of E2F from the Rb protein which is essential, not to say critical for viral replication, but it is the nuclear localisation of the human transcription factor YB-1. This transcription factor is, in normal cells, only present in the cytoplasm over most of the cell cycle. After infection with an adenovirus it is induced into the nucleus under certain circumstances or is already present in the nucleus in distinct cellular systems, such as distinct tumor diseases including, for example, but not limited thereto, breast cancer, ovary carcinoma, prostate carcinoma, osteosarcoma, glioblastoma, melanoma, small cell lung carcinoma and colorectal carcinoma.

Figure 3:
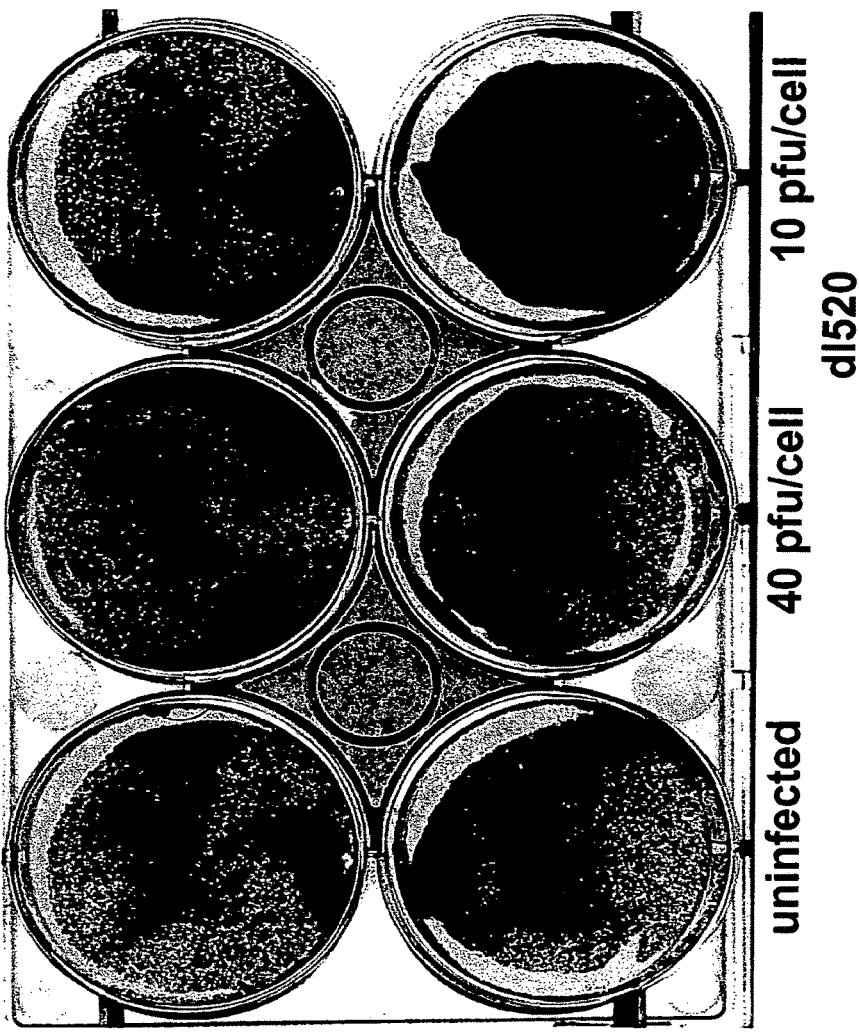
FIG. 3 shows U2OS cells which do not have YB-1 in the nucleus, after infection with the E1/E3-deleted adenoviruses Ad5, referred to as E1/E3-minus Ad5, and dl520.

EXAMPLE 3: INFECTION OF U2OS CELLS 100,000 U2OS cells were plated per well. On the next day the cells were infected with the various adenoviruses as depicted in FIG. 3. The infection was performed in 500 µl serum free DMEM medium at 37° C. for 1 h. Subsequently, the infection medium was removed and replaced by 2 ml complete medium (10% FCS/DMEM). The analysis was performed after 3 days using crystal violet staining.

As may be taken from FIG. 3, the U2OS cells which do not have YB-1 in the nucleus, show no lysis as illustrated by crystal violet staining after infection with two different adenoviruses, namely the E1/E3-deleted adenovirus referred to as E1/E3-minus, and adenovirus d1520, which can be used in accordance with the present invention. In connection therewith, first, the medium is removed. Subsequently, the cells are overlaid with crystal violet (50% ETOH, 3% formaldehyde, 5% acetic acid, 1% crystal violet) and incubated at room temperature for 5-10 min. Subsequently, the plates having 6 wells are thoroughly rinsed with water and dried at room temperature.

This confirms the finding underlying the present invention that the presence of YB-1 is required in order to induce the viruses used in accordance with the present invention, to lyse the infected cells.

Figure 4:
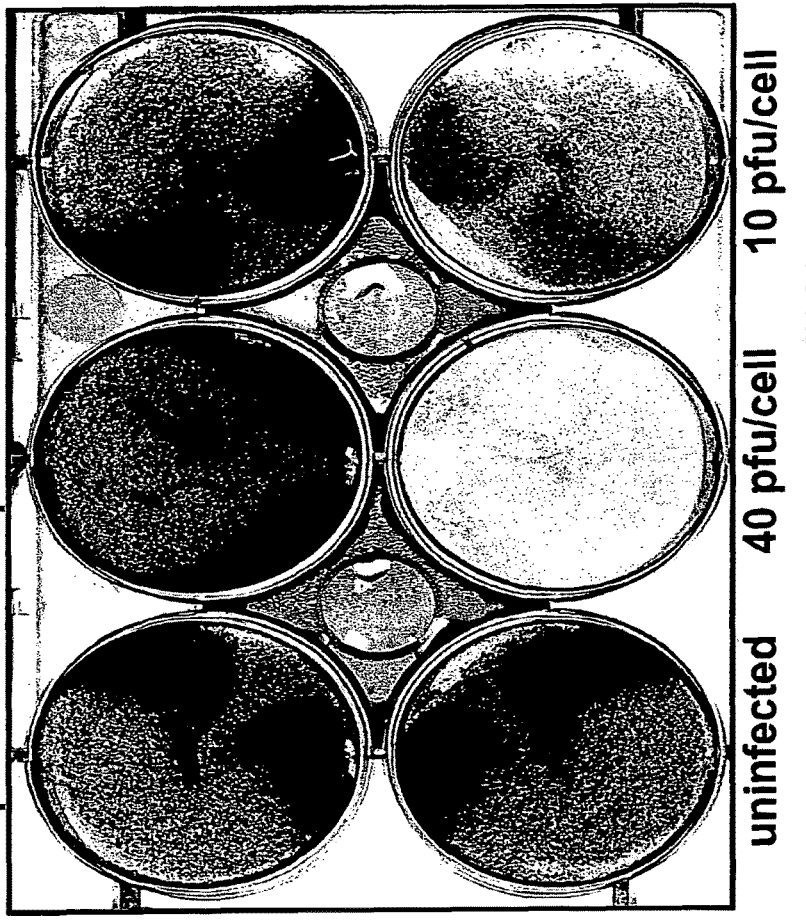
FIG. 4 shows 257RDB cells which have YB-1 in the nucleus, after infection with the E1/E3-deleted adenoviruses Ad5, referred to as E1/E3-minus Ad5, and adenovirus dl520.

EXAMPLE 4: INFECTION OF 257RDB CELLS 100,000 257RDB cells were plated per well. On the next day the cells were infected with the various adenoviruses as depicted in FIG. 4. The infection was performed in 500 µl serum free DMEM medium for 1 h at 37° C. Subsequently, the infection medium was removed and replaced by 2 ml complete medium (10% FCS/DMEM). The analysis was performed after three days using crystal violet staining.

The result of this experiment is depicted in FIG. 4. The adenovirus referred to as E1/E3-minus Ad5 which is E1/E3-deleted, did not show any lysis at low MOIs (pfu/cell) upon infection of 257RDB cells which have YB-1 in the nucleus. In contrast thereto, d1520 Much, as shown in example 3, does not replicate in YB-1 nucleus-negative cells and at the same time codes with E1A for a transactivating oncogene protein in accordance with the present invention, results in a factually complete lysis at an MOI (multiplicity of infection) of 40 pfu per cell and a still predominant lysis at an MOI of 10 pfu per cell. It can be concluded therefrom that d1520 and similar viruses such as described herein by d11119/1131 or AdXvir 03, require an MOI which is reduced by about 1 magnitude (factor of ten) compared to E1-deleted or an E1/E3-deleted adenovirus which justifies their clinical use.

As depicted in FIG. 7, the protein E1A of d1520 is characterised in that the CR3 region thereof is deleted which results in the transactivation required for the use in accordance with the present invention and replication in YB-1 nucleus-positive cells.

EXAMPLE 5: INFECTION OF 257RDB AND U2OS CELLS WITH D11119/1131

Figure 5:
FIG. 5 shows 257RDB cells and U2OS cells after infection with adenovirus dl1119/1131.

As depicted in FIG. 5, there is no lysis at an MOI of 20 pfu per cell upon infection of YB-1 nucleus-negative U2OS cells with adenovirus d11119/1131 which exhibits a deletion of amino acids 4-138 of the E1A protein and the nucleic acid coding therefor, and further comprises a stop codon after amino acid 218, whereby the expressed truncated E1A protein comprises the CR3 region of the complete E1A protein. As a negative control a non-infected cell layer was used.

In contrast thereto, there was factually a complete lysis of the cell layer at an MOI of 20 pfu per cell under the influence of adenovirus d11119/1131 in a cellular system such as 257RDB which contains YB-1 in the nucleus, i. e. is YB-1 nucleus-positive. Insofar this example is another proof that a modified E1A oncogene protein which, as depicted in FIG. 7, comprises, for example, only the CR3 region and which is lacking the CR1 region and CR2 region, provides for the required transactivation in YB-1 nucleus-positive cells which is required for the replication of adenoviruses in accordance with the present invention, which results in viral replication. The adenovirus d11119/1131 is thus a further adenovirus which can be used in accordance with the present invention. It is within the present invention that also viruses can be used which are designed similar to d11119/1131 with regard to the CR3 region, but, in contrast thereto, have the CR1 region and/or CR2 region.

EXAMPLE 6: DETECTION OF NUCLEAR YB-1 IN MULTIDRUG RESISTANT CELLS

The example is based on the consideration that nuclear YB-1 should bind as a transcription factor to the Y-box (CAAT sequence) within the mdr1 promoter (engl. multiple drug resistance promoter). In order to detect this, a so-called EMSA analysis (electrophoretic mobility shift assay) was performed. In connection therewith, nuclear protein is isolated and subsequently 1-10 g protein is incubated together with a short DNA fragment (oligo) at 37° C. In order to determine nuclear YB-1, the following oligonucleotide was used: mdr1 promoter in contrast to U2O3 (Position −86 to −67): TGAGGCTGATTGGCTGGGCA (SEQ ID NO: 1) (the X-box is underlined).

This DNA fragment is radioactively labelled at the 5' end with $^{32}$P prior to that. Subsequently, separation is performed in a native polyacryl amide-gel. In case the protein YB-1 is binding to a sequence in the oligonucleotide, this can be detected as any non-bound oligonucleotide is migrating faster in the gel than bound oligonucleotide (Holm, P. S. et al., JBC 277, 10427-10434, 2002; Bargou, R. C. et al., Nature Medicine 3, 447-450, 1997).

Figure 6:
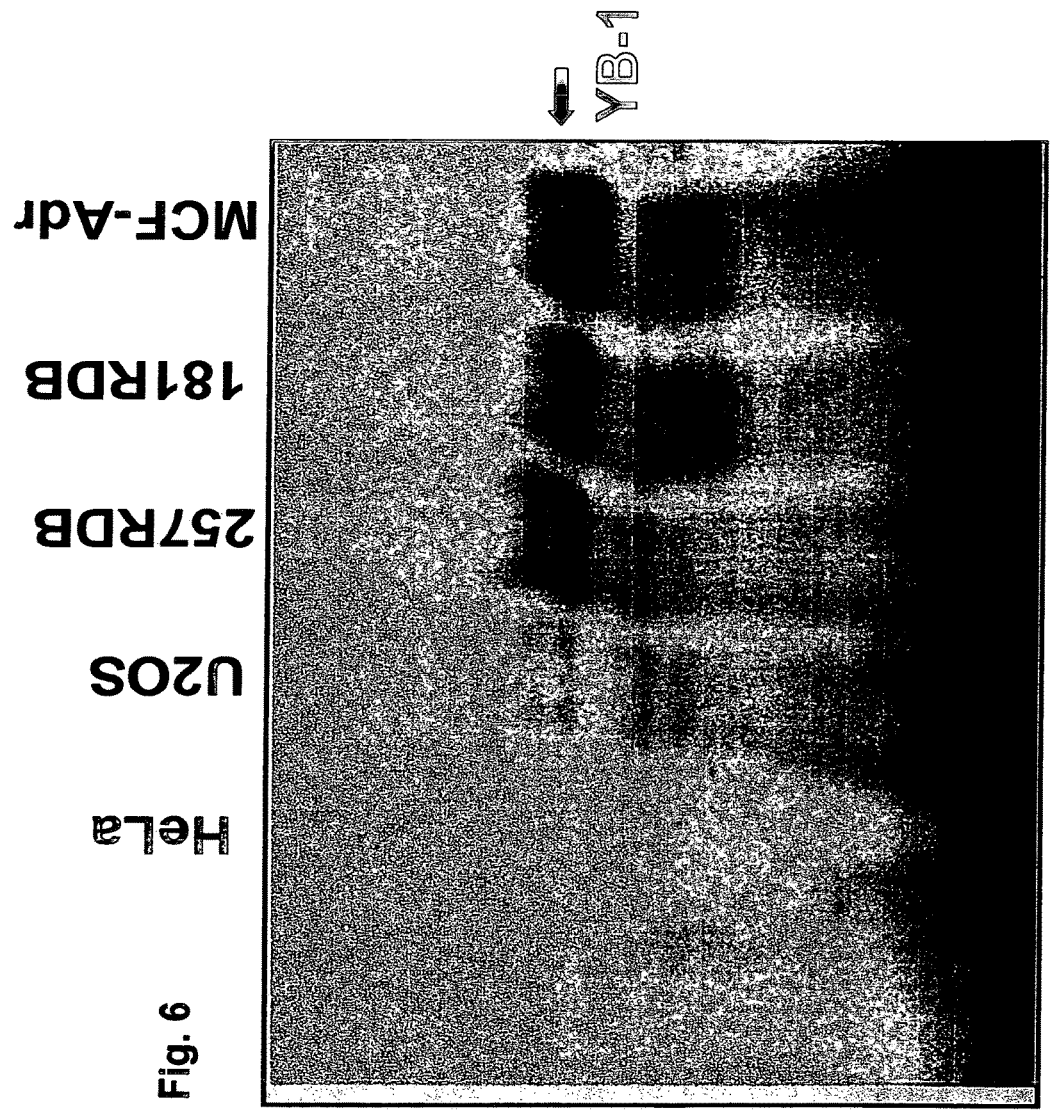
FIG. 6 shows the result of an EMSA analysis which confirms that YB-1 is present in multidrug resistant cells and cell lines 257RDB, 181 RDB, MCF-7Ad, respectively, whereas YB-1 is not present in the nucleus of U2OS and HeLa cells.

As depicted in FIG. 6, it could be shown with the EMSA analysis that YB-1 is present in the nucleus of multidrug resistant cells 257RDB, 181RDB and MCF-7Ad cells in contrast to cell lines U2OS and HeLa cells.

The results shown in example 4 and 5 confirm that the adenoviruses d1521) and d11119/1131 replicate in YB-1 nucleus-positive cells such as, e.g., 257RDB in contrast to U2O5, and induce lysis thereof. This confirms the finding about the use of the adenoviruses in accordance with the present invention. Additionally, the results confirm that already a, compared to wildtype adenovirus, weak transactivation of viral genes in YB-1 nucleus-positive cells through modified or deleted E1A gene products results in successful replication and lysis of such cells in the presence of YB-1 in the nucleus, including, for example, multidrug resistant cells and that the adenoviruses as described herein, can thus be used in the lysis of such tumors.

EXAMPLE 7: INCREASE OF REPLICATION EFFICIENCY OF E1-MINUS ADENOVIRUSES

This example shows that the early viral genes E1B55kDa and E4orf6 can be substituted through transfection with the plasmid pE4orf6 and infection with the E1/E3-deleted adenovirus Ad-55K. Ad-55K is an E1/E3 deleted virus, whereby E1B55kDa is cloned into E1 and is under the control of CMV. This substitution is necessary with regard to the fact that AdYB-1, i. e. an adenovirus which expresses YB-1, does not express these early genes and that the present inventor has recognised that a substitution of these early genes in a replication system which contains YB-1 in the nucleus, is capable of increasing replication efficiency and particle formation efficiency, respectively, to an extent comparable to the one of wildtype adenoviruses of type Ad5.

The following was done:
Transfection of each $10^5$ U2OS cells with the plasmid pE4orf6 using lipofectamine. The plasmid pE4orf6 carries the DNA sequence coding for the early viral gene E4orf6 under the control of CMV.

24 h after transfection with the plasmid pE4orf6 the cells were infected with the YB-1 expressing E1/E3-deleted adenovirus AdYB-1 (50 pfu/cell) and the E1/E3-deleted E1B55kDa adenovirus Ad-55K (50 pfu/cell). Ad-55K is an E1/E3-deleted virus which carries as transgene the viral gene E1B55kDa under CMV control.

Figure 8:
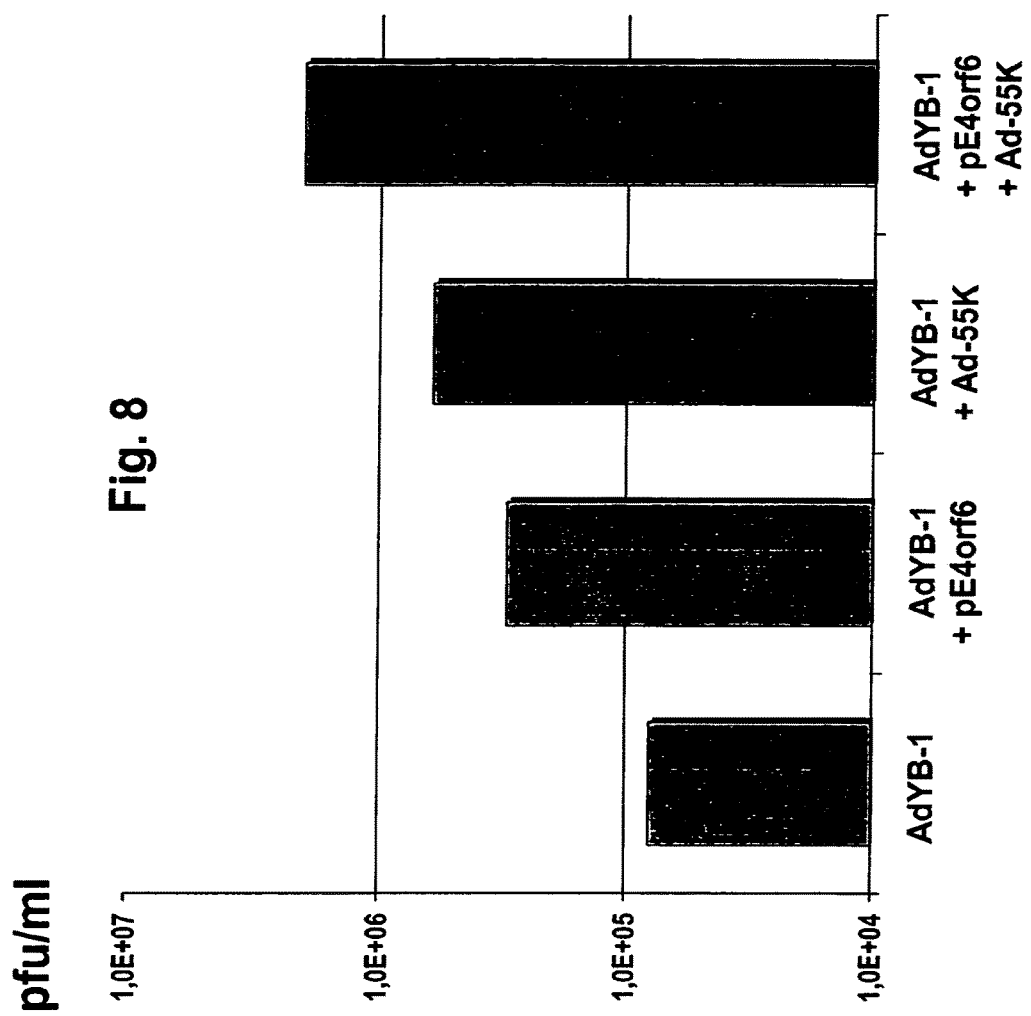
FIG. 8 is a column diagram showing the replication efficiency of adenoviruses in the presence of additionally expressed viral proteins in absolute figures.
Figure 9:
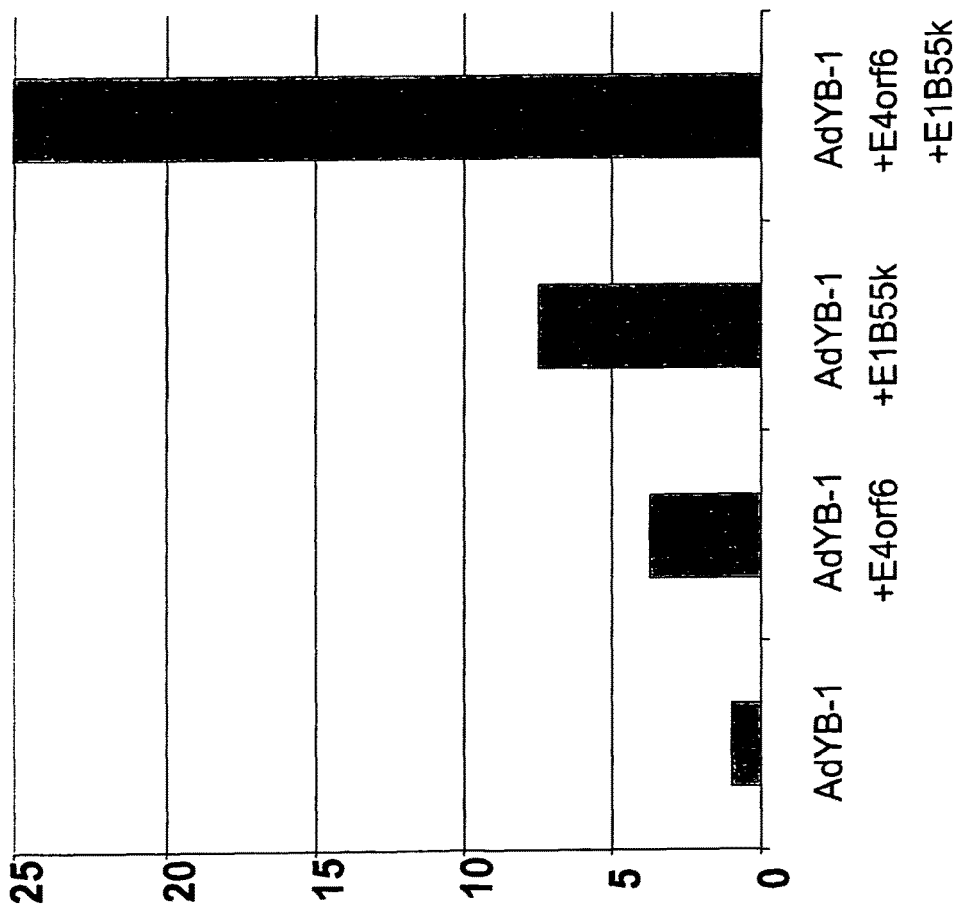
FIG. 9 is a column diagram showing the increase of replication efficiency of adenoviruses in the presence of additionally expressed viral proteins.

Subsequently, the cells were removed from the medium (2 ml) 5 days after infection (=post infectionem). The release of the viral particles from the isolated cells was done by alternating freezing and thawing for three times (thaw/freeze). Subsequently, a plaque assay was performed on 293 cells for determining the generated infectious particles (plaque forming units per ml (pfu/ml)). The result is depicted in FIGS. 8 and 9. FIG. 8 shows the result of the plaque assay, represented in absolute figures. The most significant difference compared to infection with AdYB-1 alone is shown by transfection with the plasmid pE4orf6 and co-infection with the two viruses AdYB-1 and Ad-55K. FIG. 9 shows the result of FIG. 8, whereby the increase of the replication efficiency is represented as multifold of the replication determined for AdYB-1. The cells infected with plasmid pE4orf6 and subsequently with AdYB-1 and E1B55kDa (Ad-55K) produced up to 25 times more pfu/ml.

Based on these results it can be concluded that the substitution of E1B55kDa and E4orf6 increases the number of viruses formed (pfu/ml) after infection with the E1/E3-deleted adenovirus AdYB-1 by a factor of up to 25. The additive effects of E1B55kDa and E4orf6 on the production of plaque forming units (pfu) is significantly higher compared to the effects of each of the two gene products.

Control experiments with one plasmid which expresses EGFP, clearly showed that in the experimental approach chosen only 10% of the cells were successfully transfected with plasmid pE4orf6. The number of the particles formed in the cells which express both E1B55kDa and E4orf6 is comparable to the one of human adenovirus type 5 (wildtype). This confirms the finding underlying the present invention that the expression of E4orf6 and E1B55kDa is, in combination with the nuclear localisation of YB-1, able to provide for adenoviral replication and particle formation, in particular of E1A-deleted adenoviruses, which is comparable to the one of wildtype Ad5.

EXAMPLE 8: INCREASED REPLICATION OF ADENOVIRUSES WHICH ARE NOT REPLICATING IN YB-1 NUCLEUS-NEGATIVE CELLS, IN YB-1 NUCLEUS-POSITIVE CELLS UPON ADMINISTRATION OF CYTOSTATICS

It is known in the prior art that the addition of different cytostatics induces nuclear localisation of the human transcription factor YB-1. As has been found by the present inventor, YB-1 localised in the nucleus controls adenoviral replication by means of activation of the adenoviral E2-late promoter. The combination of both effects can be used in order to provide for specific tumor lysis.

In the practicing of the oncolytic assays the following procedure was followed: 200.000 cells (HeLa and U2OS, respectively) were plated into each well of a 6 well plate. On the next day 40 ng/ml (final concentration) of daunorubicine were added. After 3 hours of incubation the cells were infected with 10 and 30 pfu d1520/cell, respectively. Subsequently, the cells were incubated in cytostatic free medium. After 3-5 days the cells were stained using crystal violet.

Figure 10:
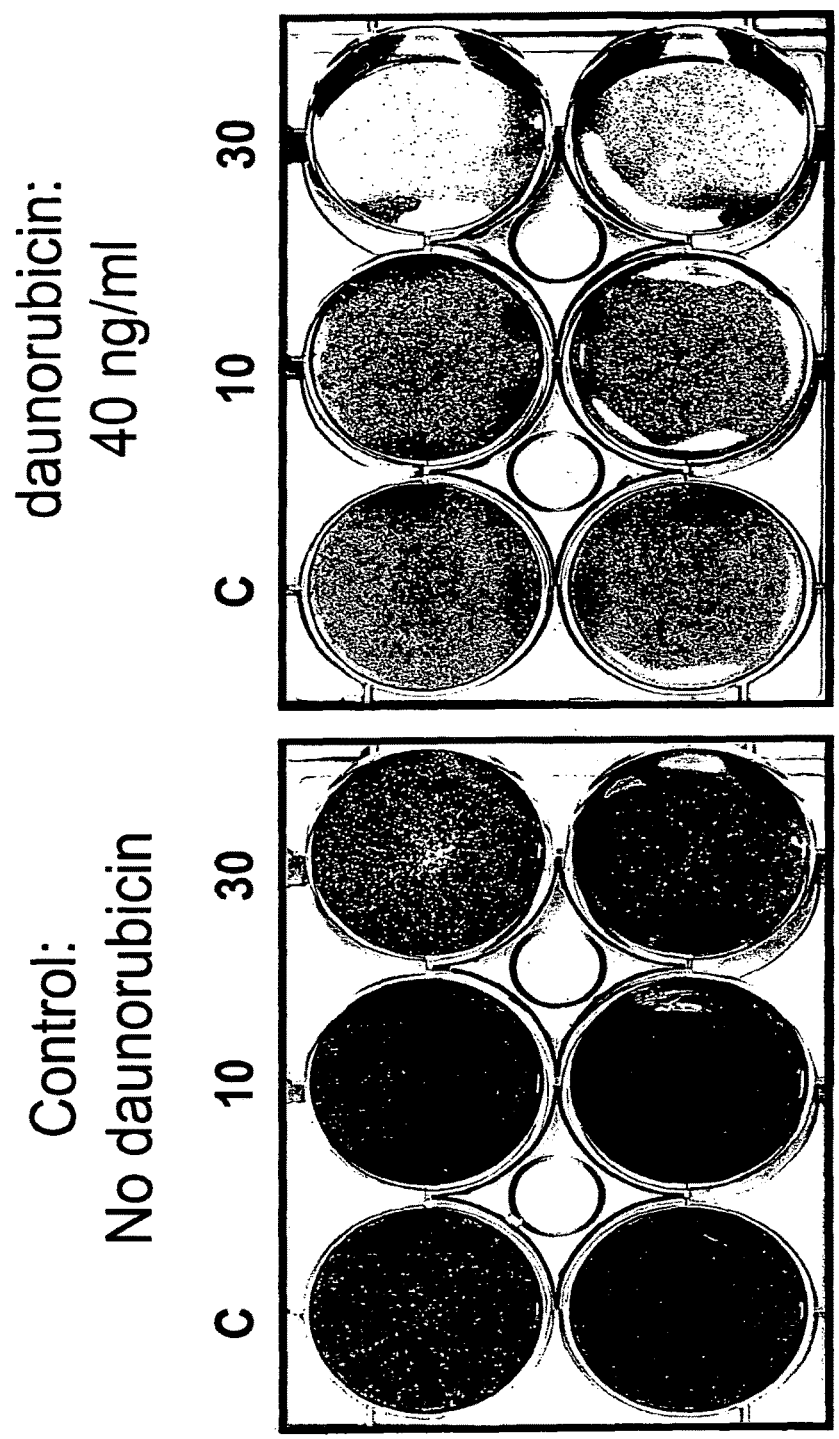
FIG. 10 shows wells grown with U2OS cells after crystal violet staining and infection with dl520 with 10 and 30 pfu/cell, respectively, and control (K) without administration of daunorubicine and with the administration of 40 ng daunorubicin per ml, respectively.
Figure 11:
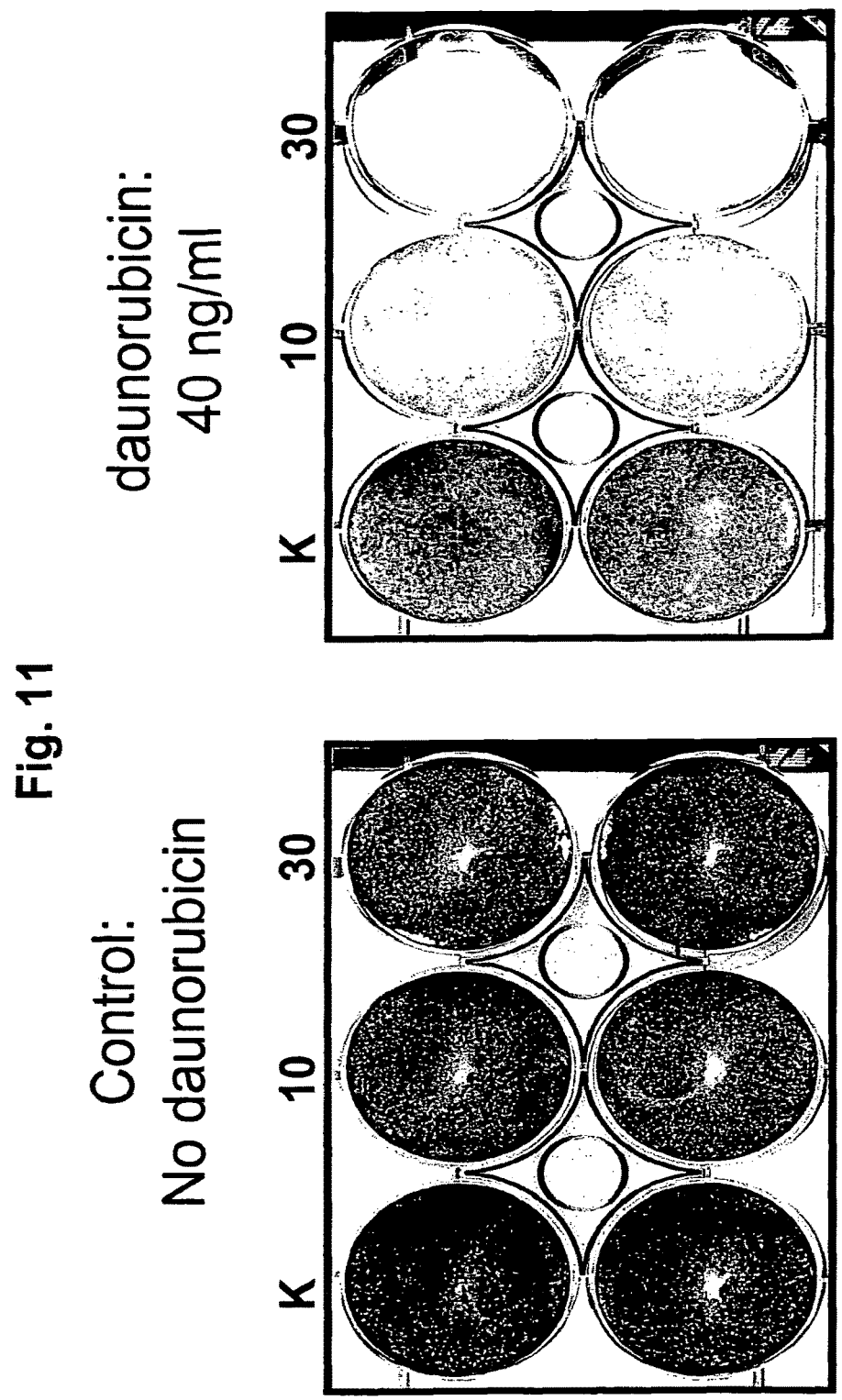
FIG. 11 shows wells grown with HeLa cells, after crystal violet staining and infection with dl520 and 10 and 30 pfu/cell and control (K), respectively, without administration of daunorubicine and administration of 40 ng daunorubicine per ml, respectively.

As may be taken from FIGS. 10 and 11, the addition of daunorubicine induces the replication of d1520 through nuclear localisation of YB-1. Thus, d1520 creates a bigger tumorlytic effect in combination with the cytostatic daunorubicine compared to daunorubicine alone.

EXAMPLE 9: IN VIVO TUMOR LYSIS BY D1520

The HeLa (YB-1 nucleus-negative) and 257RDB (YB-1 nucleus-positive) cells used in this in vivo study, were expanded under sterile cell culture conditions. Prior to the injection of the cells into mice (strain CD1NuNu) in order to generate a subcutaneous tumor, the cells are harvested by trypsinisation, taken up in DMEM medium (10% FCS), counted and washed with PBS one time. Subsequently, the cells are centrifuged, the PBS aspired and the cells are portioned in fresh PBS with the desired cell number. The cell number which was subcutaneously injected in this study, was each $5 \times 10^6$ cells of both cell lines. The injection was performed subcutaneously into one flank of the animals, whereby HeLa cells were injected into the right side and 257RDB cells were injected into the left side for better distinction. The growth of the tumors was controlled twice a week and thereby the length and the width of the tumors was measured using vernier calipers. Based thereon, the tumor volume was calculated based on the following mathematical formula:

$$\tfrac{3}{4}\pi * a/2 * (b/2)^2 \quad a=\text{length},\ b=\text{width}$$

Once the tumor has reached a volume of 200 to 520 mm$^3$, the virus and PBS as negative control, respectively, were intratumorally applied. The volumes to be injected were identical and were 50 µl each time. This was repeated on 3 consecutive days. The overall dosage of applied viruses was $5 \times 10^8$ pfu. Subsequently, the tumor growth was continued to be documented twice a week and the volume was calculated. At the end of the study the mice were sacrificed and the tumors removed for further analysis.

Figure 12:
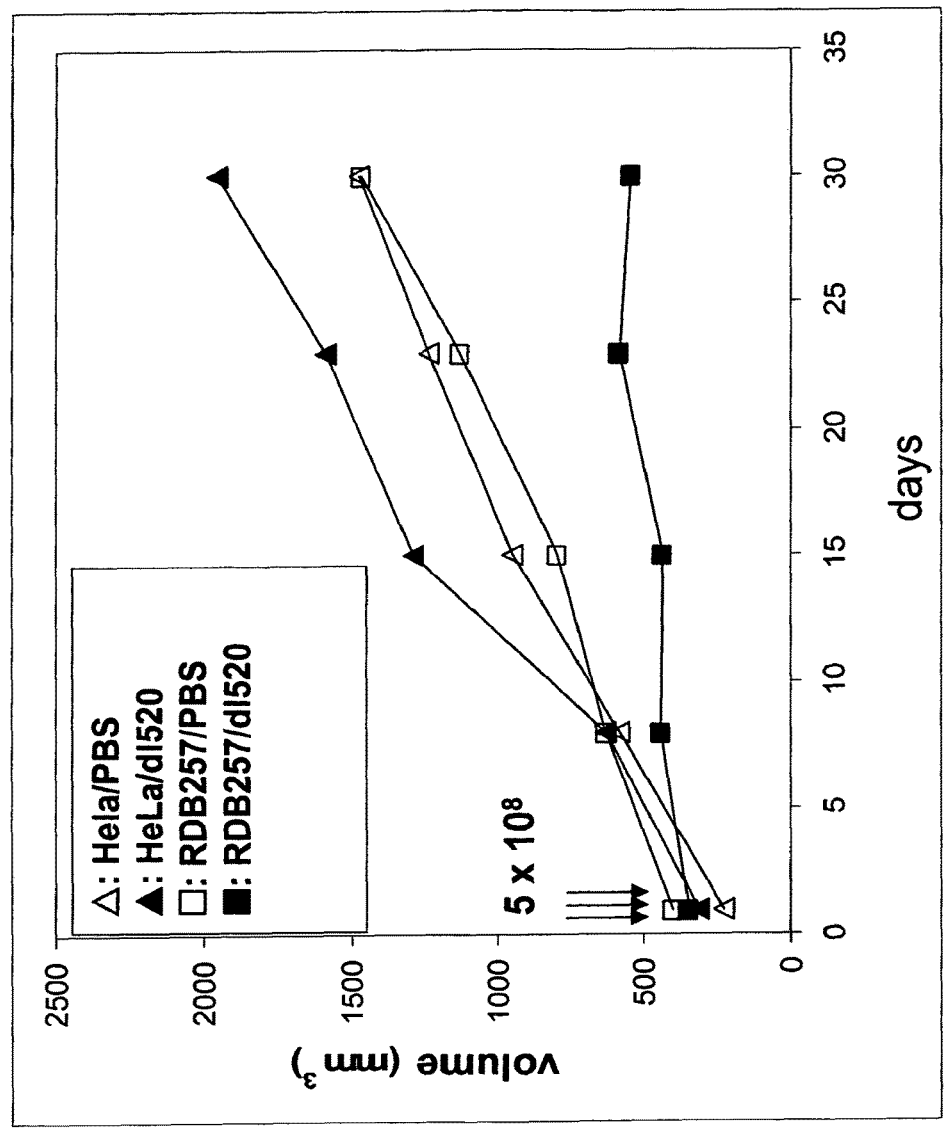
FIG. 12 is a diagram of the tumor volume of tumors having different origins (RDB257 and HeLa) as a function of time after treatment with PBS and dl520, respectively.
Figure 13:
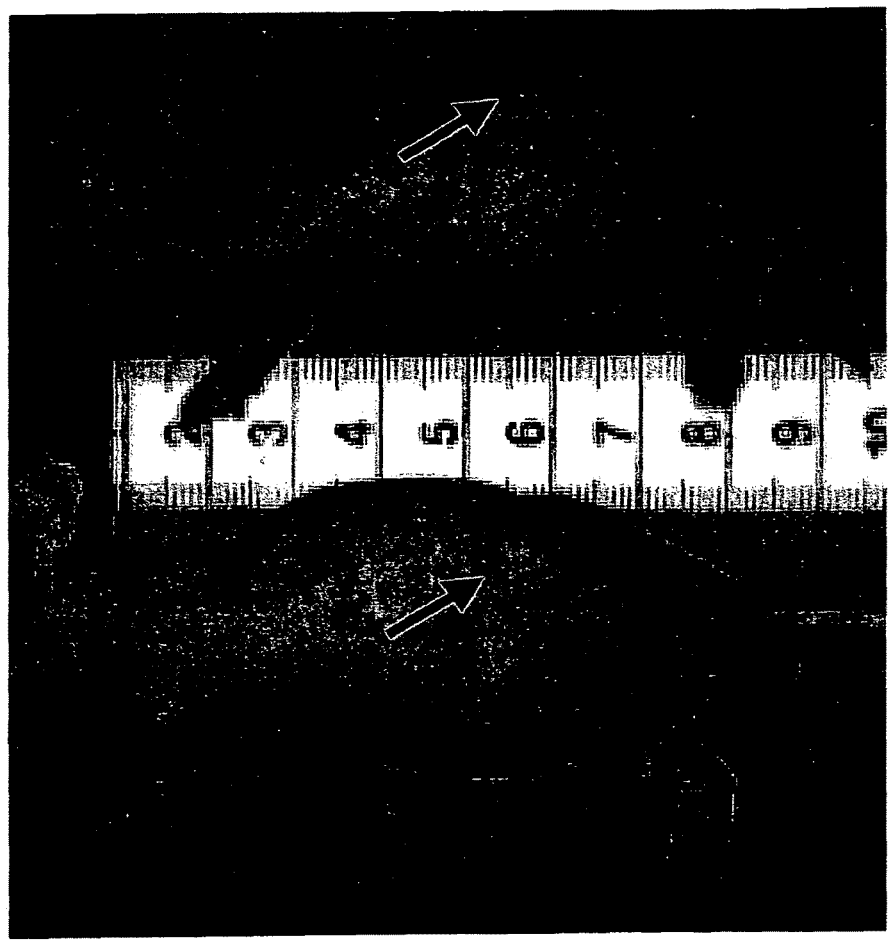
FIG. 13 show pictures of sacrificed mice which developed a tumor based on RDB257 cells after treatment with PBS and 5×10⁸ pfu dl520, respectively.

The results are depicted in FIGS. 12 and 13.

FIG. 12 shows a diagram representing the tumor volume as a function of time and the various treatment schemes. In case the tumor was formed by RDB257, there was a significant growth of the tumor to about 438 mm$^3$ to 1466 mm$^3$ upon injection of PBS. Under the influence of the vector d1520 which was used in accordance with the invention, tumor growth could be reduced significantly. Starting from a mean tumor size of 344 mm$^3$, the tumor size increased only by 21% to a total of 543 mm$^3$.

In the present example the tumor consisting of HeLa cells was used as a control which upon administration of PBS behaved similarly to the RDB257 based tumor upon administration of PBS. Tumors based on HeLa cells and treated with d1520, however, still showed a significant increase in tumor growth starting from 311 mm$^3$ and increasing to 1954 mm.

FIG. 13 shows a picture of the sacrificed nude mice which had a tumor grown using RDB257. It can be clearly seen that after the application of adenovirus d1520 in accordance with the present invention a significant reduction of the tumor occurred. In the present case there was even a reduction in the tumor volume (day 1 after administration of virus d1520; 515 mm$^3$; day 30 after administration of virus d1520: 350 mm$^3$).

EXAMPLE 10: SOUTHERN BLOT OF TUMOR DNA

DNA was extracted from a tumor sample which has been taken from the middle of the tumor developed in example 9. For isolation the Dneasy Tissue Kit of Qiagen is used. The DNA isolation is done in accordance with manufacturer's instructions. In accordance therewith, the DNA was released from the cells through alkaline lysis. Subsequently, the isolated DNA is purified over a column. Subsequently, the concentration of the isolated DNA is determined by photometry at 260 nm. The analysis was performed using 2 µg of the DNA samples which were digested with 10 units of restriction enzyme Kpn I. Subsequently, an electrophoretic separation of the samples was performed in a 0.8% agarose gel. Subsequently, the DNA was blotted onto a nylon membrane (performed according to the system of Schleicher & Schuell). The DNA blotted onto the membrane is hybridised against a specific 1501 bp DNA probe. The 1501 bp DNA probe specifically binds to the 3369 bp Kpn I fragment within the E2A coding Ad5 sequence. The probe was prepared by PCR (primer: 5'-GTC GGA GAT CAG ATC CGC GT (SEQ ID NO: 2), 5'-GAT CCT CGT CGT CTT CGC TT (SEQ ID NO: 3)) and radioactively labelled using $^{32}$P. Subsequently, the membrane is washed and exposed to a film.

Figure 14:
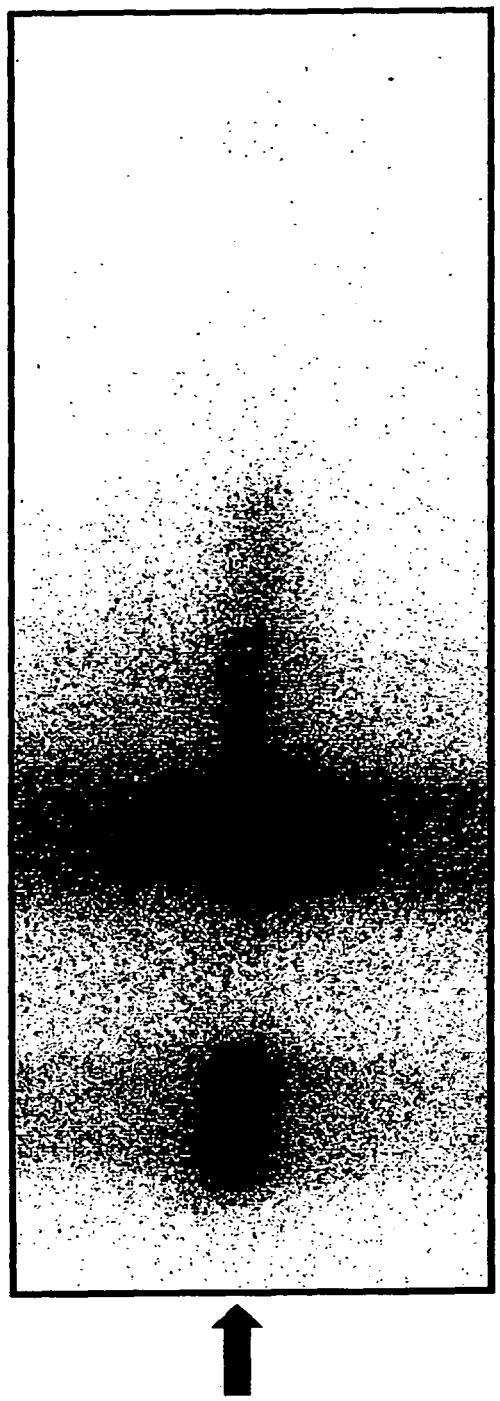
FIG. 14 is the result of a Southern Blot analysis of a cell extract (of the tumors grown subcutaneously) of RDB257 cells and HeLa cells after infection with dl520.

The result of the Southern Blot of tumor DNA is depicted in FIG. 14. The analysis confirms that only d1520 replicates in vitro in resistant cells RDB257, as depicted in lanes 3, 4 and 5. Lane 1 shows as positive control Ad-5d, lane 6, 7 and 8 show DNA from HeLa cells which were infected with d1520. As HeLa cells are not YB-1 nucleus positive the virus d1520 did not replicate so that, in accordance therewith, the E2A sequence could not be detected.

Figure 15:
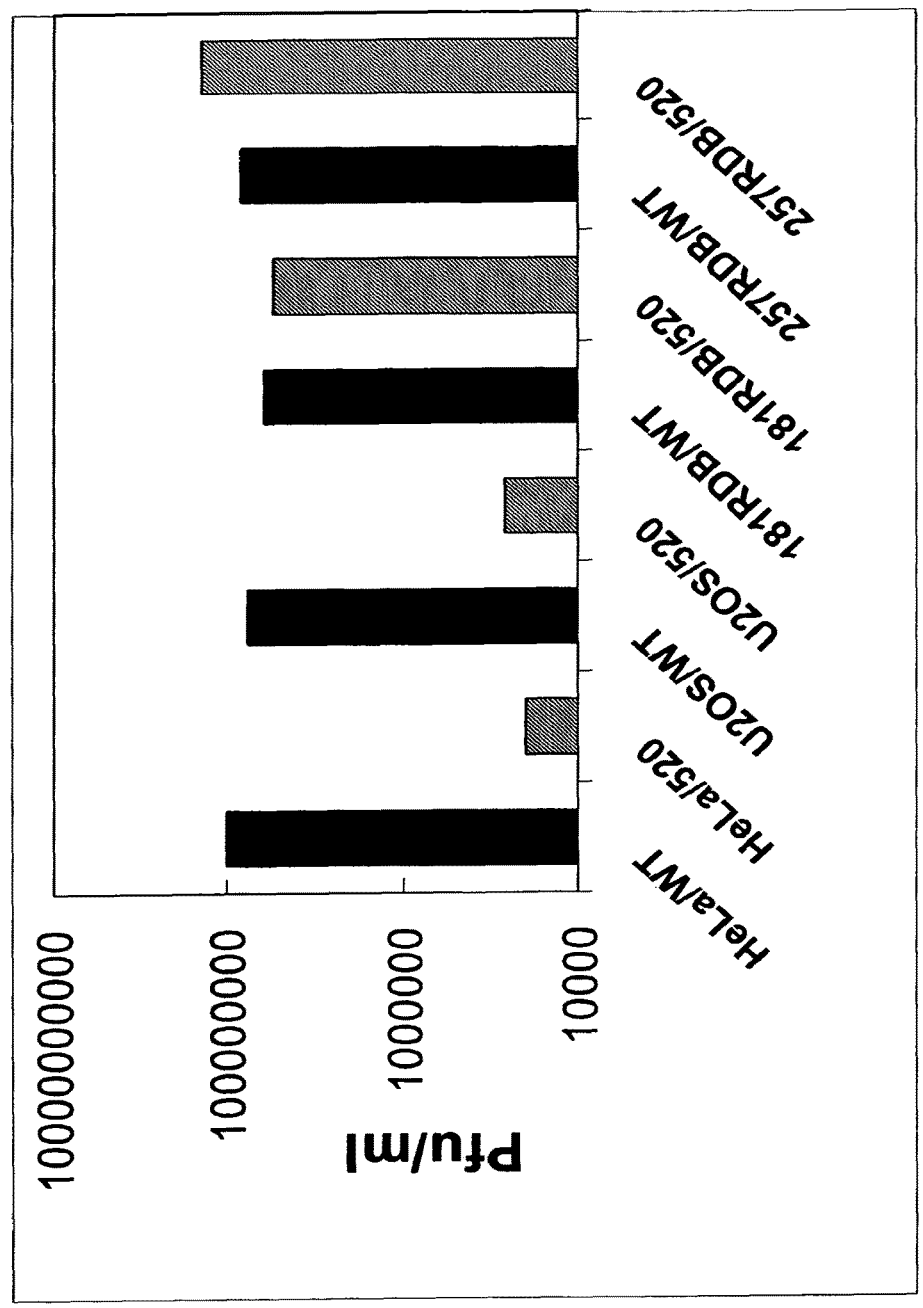
FIG. 15 is a column diagram showing the replication efficiency and particle formation, respectively, of dl520 and wildtype adenoviruses in YB-1 nucleus-positive tumor cells (257RDB and 181RDB) and YB-1 nucleus-negative tumor cells (HeLa, U2OS).

A further result with d1520 is depicted in FIG. 15. Based on a plaque assay the particle formation (pfu/ml) was investigated after infection with d1520 and wildtype adenovirus. Various YB-1 nucleus-positive (257RDB and 181RDB) tumor cells and YB-1 nucleus-negative tumor cells were infected with d1520 and wildtype adenovirus.

The following procedure was practiced:

100,000-200,000 cells each were plated in so-called plates having 6 wells (engl. 6 well plates) in L 15 medium (resistant cells) and DMEM (non-resistant cells) having 10% FCS. After 24 h infection with d1520 and wildtype adenoviruses (10 pfu/cell) was performed 3 days after infection (post infectionem) the viral particles were released from the cell suspension (3 ml) by alternating freezing and thawing for three times. Subsequently, a plaque assay was performed on 293 cells for determining the formed infectious particles (plaque forming units per ml (pfu/ml)). The result is depicted in FIG. 15. The result of the plaque assay shows that d1520 is replicating in YB-1 nucleus-positive cells (257RDB and 181RDB) similar to wildtype adenovirus. Insofar a replication efficiency can be observed similar to the one of wildtype adenoviruses when using, in accordance with the present invention, the adenoviruses described herein.

EXAMPLE 11: STRUCTURAL DESIGN OF THE ADENOVIRAL VECTOR XVIR03

Figure 16:
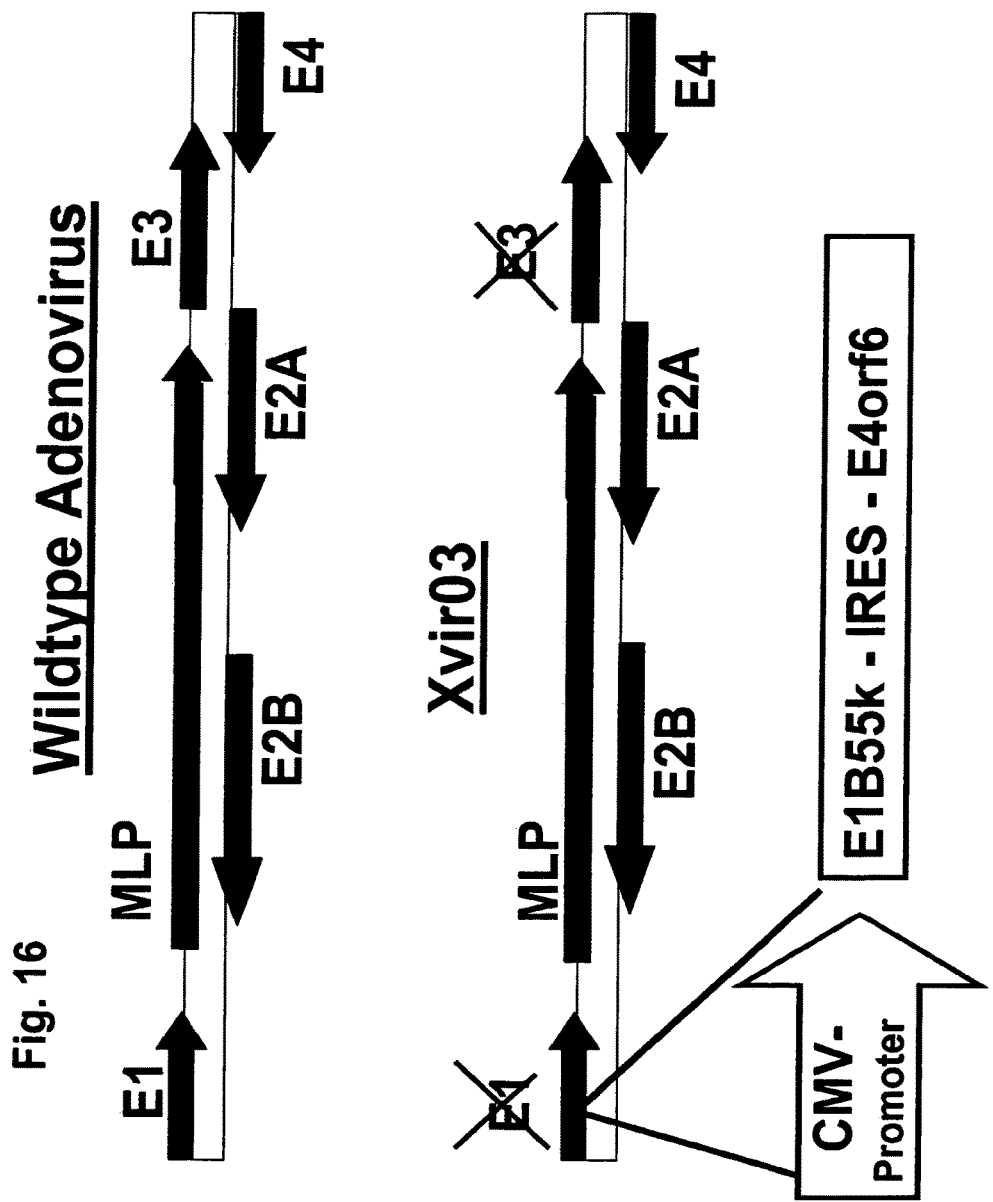
FIG. 16 shows the structural design of wildtype adenovirus and adenoviral vector AdXvir03.

FIG. 16 shows the structural design of the adenoviral vector Xvir03. The adenovirus Xvir03 is a so-called E1/E3-deleted adenovirus. This means that no E1A, E1B and E3 proteins are manufactured which are functional in adenoviral replication. The deletion of the E1 region extends from 342-3528; the deletion of the E3 region of the amino acid position 27865-30995. As used herein, the term "E1-deleted virus" means a virus in which E1 is no longer functionally active. This can be achieved by inactivation with an otherwise mostly intact nucleic acid and amino acid sequence, however, can also mean a deletion of the E1 region coding proteins having various sizes. Because of the lack of the E1A and E1B protein and the nucleic acids coding therefor, the E4 region, such as E4orf6, is only weakly expressed (about 1-5% compared to wildtype adenoviruses) or expressed not at all. The viral genes E1B55kDa and E4orf6 are expressed in the E1 region by means of the heterologous CMV promoter (Clontech: Plasmid pShuttle) introduced into Xvir03. Instead of the CMV promoter each and any of the promoters as disclosed herein in connection with the expression of E1A can be used. The open reading frame of both genes is linked with each other by means of a so-called IRES sequence (engl, internal ribosomal entry site) (Pelletier, J. and Sonenberg, N. Nature, 1988, 334, 320-325). This element (Novagen: pCITE) provides for the expression of 2 proteins from one mRNA.

The vector was manufactured as follows:

The plasmid E1B55kDa-pShuttle was created by cloning the open reading frame of E1B55kDa from pCGNE1B from M. Dobelstein (University of Marburg) with XbaI and BfrI into the pShuttle vector from Clontech. Subsequently, E1B55kDa in pShuttle was linearised with ApaI, the ends blunt ended and cut with NheI.

In a second vector, pcDNA3.1(+) (Invitrogen), subsequent to each other the IRES element as a PCR product was cloned with pCITE-4a(+) of the company Novagen as template by means of TA cloning into the EcoRV cleaving site, and the E4orf6 from the plasmid pCMV-E4orf6 (M. Dobelstein, University of Marburg) was cloned by means of BamHI=IRES-E4orf6-pcDNA3.1 (+). IRES-E4orf6 in pcDNA3.1(+) was linearised with NotI, the ends blunt ended and subsequently the fragment IRES-E4orf6 was cut out with NheI. The fragment IRES-E4orf6 was linked with the open vector E1B55kDa-pShuttle (blunt, NheI). The cassette was subsequently cloned from the E1B55kDa-IRES-E4orf6-pShuttle together with the CMV promoter and the bovine growth hormone (BGH)-PolyA into the ΔE1, ΔE3 Adeno-X-Plasmid (Clontech) with I-Ceu I and PI-SceI, and referred to as AdcmvE1B/IRES/E4orf6. Subsequently, the adenovirus was made in accordance with manufacturer's instructions (Clontech). The adeno plasmid which was linearised with PacI having the expression element CMV-E1B55kDa-IRES-E4orf6-BGH polyA was transfected into HEK293 cells and 11 days post transfectionem the ablating cells were removed together with the medium in order to release the adenoviruses through repeated freeze-thaw cycles.

The vector described above is in principle suitable as are the other viruses described herein for use in accordance with the present invention. In particular the afore-described vector is suitable to replicate and trigger lysis insofar, in cells which are YB-1 nucleus-positive cells as well as in cells where YB-1 is deregulated, i. e. is overexpressed compared to normal cells and non-tumor cells, respectively. The use of this vector particularly applies to those diseases and groups of patients or collectives of patients which are disclosed in connection with the other adenoviruses which are described herein to be used in accordance with the present invention and the other adenoviruses of the present invention disclosed herein.

EXAMPLE 12: STRUCTURAL DESIGN OF THE ADENOVIRAL VECTOR XVIR03/01

Figure 17:
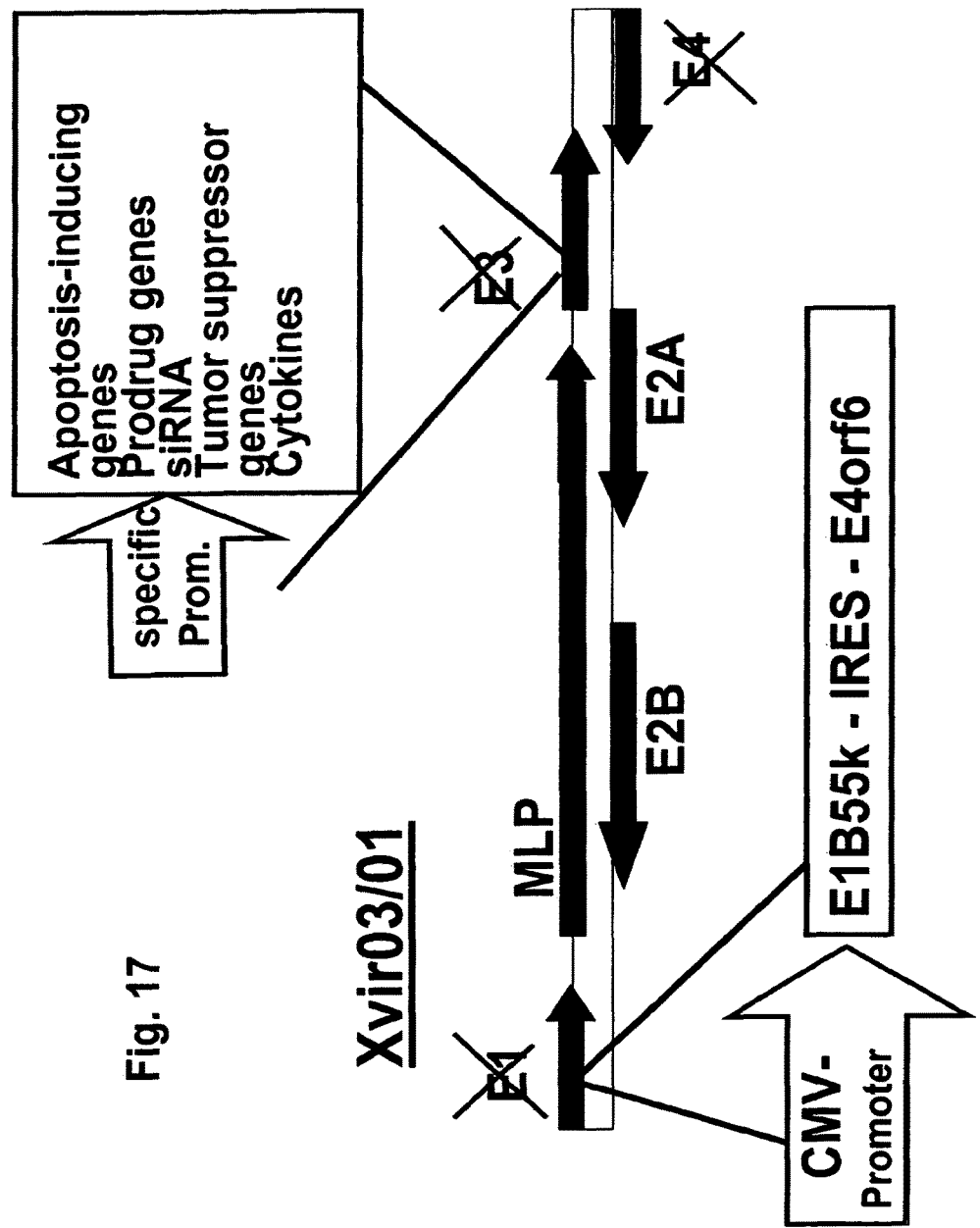
FIG. 17 shows the structural design of adenoviral vector AdXvir03/01.

As may be taken from FIG. 17, Xvir03/01 is a further development of Xvir03. Therapeutic genes such as, for example, the genes described herein and the transgene can be cloned into the E3 region. Additionally, a deletion was introduced into the E4 region so as to avoid homologous recombination with the E4orf6 from the expression cassette of Xvir03. This allows that larger transgenes can be cloned in this construct. The deleted E3 region contains SacI, NdeI and NheI restriction sites for introducing a cassette, into which, for example, the therapeutic transgenes can be cloned.

Preparation of a Plasmid for Cloning Therapeutic Genes into the E3 Region as Well as for Making Deletions in the E4 Region:

The pAdenoX-Plasmid of Clontech has a restriction site for SfuI behind the 3' ITR region which is absent in wildtype adenovirus. The E3-E4 region was taken from pAdenoX (Clontech) with the SpeI (position 23644) and SfuI and transferred into pcDNA3.1(+) (Invitrogen)=pcDNA3.1-E3Δ27865-30995-E4. The majority of E4ORF6, namely 33241-33875 was removed by means of PstI=pcDNA3.1-E3Δ27865-30995,E4Δ33241-33875. For the further development of Xvir03 the deleted E3/E4 region from pcDNA3.1-E3Δ27865-30995,E4Δ33241-33875 was cloned by means of SfuI and SpeI into plasmid pAdenoX=pAdenoX E3Δ27865-30995,E4Δ33241-33875.

The expression cassette was subsequently, as described for Xvir03, cloned with I-Ceu I and PI-SceI from the E1B55kDa-IRES-E4orf6-pShuttle together with the CMV promoter and the bovine growth hormone (BGH)-PolyA into pAdenoX E3Δ27865-30995,E4Δ33241-33875 and referred to as AdcmvE1B/IRES/E4orf6-ΔE4. Subsequently, the adenovirus was made in accordance with manufacturer's instructions (Clontech).

The afore-described vector is in principle useful as are the other viruses described herein to be used in accordance with the present invention. In particular the afore-described vector is suitable to replicate in YB-1 nucleus-positive cells as well as cells in which YB-1 is deregulated, i. e. is overexpressed compared to normal cells and non-tumor cells, and to cause lysis insofar. This vector can also be used for those diseases and groups of patients and collectives of patients which are disclosed herein for the other adenoviruses to be used in accordance with the present invention and the adenoviruses in accordance with the present invention.

EXAMPLE 13: ONCOLYTIC EFFECT OF XVIR03 IN 257 RDB AND 181 RDB CELLS 100,000 cells (257RDB and 181RDB) were plated per well of a plate having six wells (engl.: 6 well plate). On the next day the cells were, as depicted in FIG. 18, infected with Ad312 (20 pfu-cell) and Xvir03 (5 pfu/cell). The infection was performed in 500 µl serum free DMEM medium at 37° C. for 1 h. Subsequently, the infection medium was removed and replaced by 2 ml complete medium (10% FCS/DMEM). The analysis was done by means of crystal violet staining after 5 days. The result is depicted in FIGS. 18A and 18B.

As may be taken from FIGS. 18A and 18B, the multidrug resistant cells which have YB-1 in the nucleus, show lysis after infection with Ad312 and Xvir03 only in case of Xvir03 as represented by the crystal violet staining of the cells. In connection therewith, first the medium is removed. Subsequently the cells are covered with crystal violet (50% ETOH, 3% formaldehyde, 5% acetic acid, 1% crystal violet) and incubated at room temperature for 5-10 min. Subsequently, the six well plates are thoroughly rinsed with water and dried at room temperature.

It is known to the present inventor that E1A-deleted viruses (e. g. Ad312) which, however, are not transactivating adenoviruses in the sense of the present invention, may very efficiently replicate at higher MOIs (Nevins J. R., Cell 26, 213-220, 1981), which, however, cannot be realised in clinical application. This phenomenon is referred to in the literature as "E1A-like activity". The adenovirus Ad312 as used herein, is an E1A-deleted virus. At the titer used (20 pfu/cell), which is still above the clinically desirable titer, the early adenoviral genes such as E1B55kDa and E4orf6 are not expressed or expressed only to a very small extent (Nevins J. R., Cell 26, 213-220, 1981). As already described herein, these genes and proteins play an important role in viral replication. In contrast thereto, these genes and proteins, respectively, are expressed by adenovirus Xvir03

(FIG. 16). As may be taken from FIGS. 18A and 18B, the expression of the genes E1B55kDa and E4orf6 will result in an efficient viral replication and cell lysis at a concomitantly lower infection titer required (expressed as pfu/cell). This confirms the finding underlying the present invention, namely that the expression of E4orf6 and E1B55kDa (and the absence of E1A) in combination with nuclear localisation of YB-1 is capable of inducing a very efficient adenoviral replication. The titer required therefor of only 1 to 5 pfu/cell now allows for clinical application.

This confirms the finding underlying the present invention, namely that the presence of YB-1 in the nucleus, particularly the presence independent from the cell cycle, is required in order to make the viruses which are to be used in accordance with the present invention, lyse infected cells.

The features of the invention disclosed in the preceding specification, the claims as well as the figures can both individually as well as in any combination be important to the realisation of the invention in its various embodiments.

administering to the subject in need thereof an AdΔ24 adenovirus that is replication deficient in cells that lack YB-1 in the nucleus, wherein the adenovirus comprises an E1A protein lacking a functional CR2 domain; and wherein the cancerous tumor, or a portion thereof, is resistant to at least one pharmacological agent.

2. The method of claim 1, wherein the virus encodes for YB-1.

3. The method of claim 1, wherein the cells that form the cancerous tumor, or part thereof, overexpress membrane-bound transport protein P glycoprotein.

4. The method of claim 1, wherein the E1A protein does not induce nuclear localization of YB-1.

5. The method of claim 4, wherein the E1A protein is encoded by a gene that is under the control of a tissue and/or tumor specific promoter.

6. The method of claim 2, wherein the YB-1 is under the control of a tissue and/or tumor specific promoter.

The invention claimed is:

1. A method for the treatment of a subject identified to have a cancerous tumor that expresses Y box binding protein 1 (YB-1), the method comprising:

7. The method of claim 1, wherein the E1A protein transactivates at least one of E1B55 kDa, 4orf3, E4orf6, and E3ADP.

* * * * *

UNITED STATES PATENT AND TRADEMARK OFFICE
CERTIFICATE OF CORRECTION

PATENT NO. : 10,538,744 B2
APPLICATION NO. : 15/452470
DATED : January 21, 2020
INVENTOR(S) : Per Sonne Holm Page 1 of 1

It is certified that error appears in the above-identified patent and that said Letters Patent is hereby corrected as shown below:

In the Claims

Claim 7, Column 38, Line 64 delete:
"transactivates at least one of E1B55 kDa, 4orf3, E4orf6, and"
Insert:
--transactivates at least one of E1B55kDa, 4orf3, E4orf6, and--

Signed and Sealed this
Second Day of June, 2020

Andrei Iancu
*Director of the United States Patent and Trademark Office*

```
                        SEQUENCE LISTING

<160> NUMBER OF SEQ ID NOS: 3

<210> SEQ ID NO 1
<211> LENGTH: 20
<212> TYPE: DNA
<213> ORGANISM: Artificial
<220> FEATURE:
<223> OTHER INFORMATION: Chemically synthesized
<220> FEATURE:
<221> NAME/KEY: misc_feature
<223> OTHER INFORMATION: Oligonucleotide probe

<400> SEQUENCE: 1
tgaggctgat tggctgggca                                                  20

<210> SEQ ID NO 2
<211> LENGTH: 20
<212> TYPE: DNA
<213> ORGANISM: Artificial
<220> FEATURE:
<223> OTHER INFORMATION: Chemically synthesized
<220> FEATURE:
<221> NAME/KEY: misc_feature
<223> OTHER INFORMATION: Oligonucleotide probe

<400> SEQUENCE: 2
gtcggagatc agatccgcgt                                                  20

<210> SEQ ID NO 3
<211> LENGTH: 20
<212> TYPE: DNA
<213> ORGANISM: Artificial
<220> FEATURE:
<223> OTHER INFORMATION: Chemically synthesized
<220> FEATURE:
<221> NAME/KEY: misc_feature
<223> OTHER INFORMATION: Oligonucleotide probe

<400> SEQUENCE: 3
gatcctcgtc gtcttcgctt                                                  20
```